(12) United States Patent
Lee et al.

(10) Patent No.: US 9,199,944 B2
(45) Date of Patent: Dec. 1, 2015

(54) N2,N4-BIS(4-(PIPERAZINE-1-YL)PHENYL) PIRIMIDINE-2,4-DIAMINE DERIVATIVE OR PHARMACEUTICALLY ACCEPTABLE SALT THEREOF, AND COMPOSITION CONTAINING SAME AS ACTIVE INGREDIENT FOR PREVENTING OR TREATING CANCER

(71) Applicant: KOREA RESEARCH INSTITUTE OF CHEMICAL TECHNOLOGY, Daejeon (KR)

(72) Inventors: Kwangho Lee, Daejeon (KR); Hyoung Rae Kim, Daejeon (KR); Chi Hoon Park, Daejeon (KR); Chong Ock Lee, Seoul (KR); Jong Kook Lee, Chuncheon-si (KR); Hee Jung Jung, Daejeon (KR); Sung Yun Cho, Daejeon (KR); Chong Hak Chae, Daejeon (KR); Sang Un Choi, Daejeon (KR); Jae Du Ha, Daejeon (KR)

(73) Assignee: KOREA RESEARCH INSTITUTE OF CHEMICAL TECHNOLOGY, Daejeon-si (KR)

( * ) Notice: Subject to any disclaimer, the term of this patent is extended or adjusted under 35 U.S.C. 154(b) by 0 days.

(21) Appl. No.: 14/617,079

(22) Filed: Feb. 9, 2015

(65) Prior Publication Data
US 2015/0152069 A1 Jun. 4, 2015

Related U.S. Application Data

(63) Continuation of application No. PCT/KR2013/004767, filed on May 30, 2013.

(30) Foreign Application Priority Data

Aug. 10, 2012 (KR) .......................... 10-2012-0087716

(51) Int. Cl.
| | |
|---|---|
| A61K 31/506 | (2006.01) |
| C07D 239/48 | (2006.01) |
| C07D 403/12 | (2006.01) |
| C07D 403/14 | (2006.01) |

(52) U.S. Cl.
CPC ............ *C07D 239/48* (2013.01); *A61K 31/506* (2013.01); *C07D 403/12* (2013.01); *C07D 403/14* (2013.01)

(58) Field of Classification Search
USPC ........................................................ 544/295
See application file for complete search history.

(56) References Cited

U.S. PATENT DOCUMENTS

| | | | |
|---|---|---|---|
| 7,517,886 B2 | 4/2009 | Singh et al. | |
| 7,589,200 B2 | 9/2009 | Singh et al. | |
| 2009/0221555 A1 | 9/2009 | Ahmed et al. | |
| 2013/0317029 A1 | 11/2013 | Pandey et al. | |

FOREIGN PATENT DOCUMENTS

| | | |
|---|---|---|
| JP | 2007-501793 A | 2/2007 |
| JP | 2007-538092 A | 12/2007 |
| KR | 1020060056353 A | 5/2006 |
| KR | 10-0904570 B1 | 6/2009 |
| KR | 1020100126863 A | 12/2010 |
| KR | 1020110010801 A | 2/2011 |
| KR | 10-1148261 B1 | 5/2012 |
| KR | 10-1411695 B1 | 6/2014 |
| WO | 2004/080980 A1 | 9/2004 |
| WO | 2005/016893 A2 | 2/2005 |
| WO | 2008/051547 A1 | 5/2008 |
| WO | 2009/143389 A1 | 11/2009 |
| WO | 2009/145856 A1 | 12/2009 |
| WO | 2012/061415 A1 | 5/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Andrzej K. Bednarek, et al; "WWOX, the FRA16D Gene, Behaves as a Suppressor of Tumor Growth", Cancer Research 61, pp. 8068-8073; Nov. 15, 2001.
Nupam P. Mahajan, et al; "Activated Tyrosine Kinase Ack1 Promotes Prostate Tumorigenesis: Role of Ack1 in Polyubiquitination of Tumor Suppressor Wwox", Cancer Research 2005; 65: (22). Nov. 15, 2005, pp. 10514-10522.
Nupam P. Mahajan, et al; "Activated Cdc42-associated kinase Ack1 promotes prostate cancer progression via androgen receptor tyrosine phosphorylation", Proc Natl Acad Sci USA May 15, 2007; 104(20); pp. 8438-8443; Epub May 9, 2007.
Edward Htun Van Der Horst, et al; "Metastatic properties and genomic amplification of the tyrosine kinase gene ACK1", PNAS; Nov. 1, 2005; vol. 102, No. 44; pp. 15901-15906.
International Search Report datqed Sep. 27, 2013; PCT/KR2013/004767.

* cited by examiner

*Primary Examiner* — Kristin Vajda
(74) *Attorney, Agent, or Firm* — Ladas & Parry LLP

(57) ABSTRACT

Disclosed herein are a new N2,N4-bis(4-(piperazin-1-yl)phenyl)pyrimidin-2,4-diamine derivative or a pharmaceutically acceptable salt thereof and a pharmaceutical composition for the prevention or treatment of cancers containing the same as an active ingredient. The compound of the present invention has excellent inhibitory effects against the activities of anaplastic lymphoma kinase (ALK) and activated cdc42-associated kinase (ACK1) and thus can improve the therapeutic effects on the treatment of cancer cells having anaplastic lymphoma kinase fusion proteins such as EML4-ALK and NPM-ALK, and also effectively prevent the recurrence of cancers thus being useful as a pharmaceutical composition for the prevention and treatment of cancers.

11 Claims, 3 Drawing Sheets

N2,N4-BIS(4-(PIPERAZINE-1-YL)PHENYL) PIRIMIDINE-2,4-DIAMINE DERIVATIVE OR PHARMACEUTICALLY ACCEPTABLE SALT THEREOF, AND COMPOSITION CONTAINING SAME AS ACTIVE INGREDIENT FOR PREVENTING OR TREATING CANCER

CROSS-REFERENCES TO RELATED APPLICATION

This patent application claims the benefit of priority from Korean Patent Application No. 10-2012-0087716, filed on Aug. 10, 2012, the contents of which are incorporated herein by reference.

BACKGROUND OF THE INVENTION

1. Field of the Invention

The present disclosure relates to a novel N2,N4-bis(4-(piperazin-1-yl)phenyl)pyrimidin-2,4-diamine derivative or a pharmaceutically acceptable salt thereof and a pharmaceutical composition for the prevention or treatment of cancers, containing the same as an active ingredient.

2. Description of the Related Art

Unlike the normal cells which can perform regular and controlled growth and inhibition as necessary, cancer is a cell mass consisting of undifferentiated cells which ignore the states required inside tissues and unlimitedly proliferate and is also called tumor. The unlimitedly proliferating cancer cells invade into the neighboring tissues and, in serious cases, cause metastasis of cancer to other organs in the body thereby accompanying severe pains resulting in death.

According to the report of the American Cancer Society, more than 12 million people in the world were newly diagnosed of cancer in 2007 and 7.6 million people died of cancer, that is, about 20,000 people died of cancer every day. In Korea, according to the 2006 report of the Statistic Korea, the number one cause of death was cancer. Accordingly, there is an urgent need for the development of a tumor therapeutic agent with excellent therapeutic effect to ensure reduction in mental and physical pains due to occurrence of cancer and struggles with the cancer and improve the quality of life. Even with the numerous efforts, the exact mechanisms of how normal cells are transformed into cancer cells have not been clearly identified yet, but various factors such as extrinsic factors (for example, environmental factors, chemicals, radiations, and viruses), and intrinsic factors (for example, genetic factors and immunological factors) are complexly involved in the occurrence of cancer. The genes associated with the occurrence of cancer are oncogenes and tumor suppressor genes, and cancers occur when the balance therebetween is not maintained due to the extrinsic or intrinsic factors.

Cancers can be largely classified into a blood cancer and a solid cancer. Cancer can develop in almost all regions of the body including lung cancer, stomach cancer, breast cancer, liver cancer, uterine cancer, esophageal cancer, skin cancer, etc. For cancer treatments, a few target therapeutic agents such as Gleevec® or Herceptin® have been used for the treatment of certain cancers but most cancer treatments have been resorting to surgeries, radiation therapies, and chemical therapies which inhibit cancer cell proliferation. However, because the existing chemical therapies are not target-specific therapies, they had the side effects due to toxicities and the drug resistance, and their treatments often led to failure regardless of their initial success in treatments. Accordingly, in order to overcome the limits of the chemical therapies, there is a continued need for the development of a target-specific therapeutic agent with an exact anticancer mechanism.

As such, numerous studies have been focused on specific molecular biological factors associated with tumorigenesis for the development of the target-specific therapeutic agents. In particular, the molecular biological factors are widely used in cancer prognosis and determination of whether chemical therapies and radiation therapies should be used.

The most representative drug to inhibit the tyrosin kinase receptor of a specific molecular biological factor may be Gleevec®. Gleevec® which acts as an anticancer agent by inhibiting the activity of Bcr-Abl fusion gene formed by chromosomal translocation in Philadelphia chromosome observed in chronic myeloid leukemia patients and is a tyrosine kinase inhibitor, has been showing a satisfactory therapeutic effect when administered to the chronic myeloid leukemia patients. Examples of the drugs showing an anticancer effect as tyrosine kinase inhibitors include epidermal growth factor receptor (EGFR) used as a therapeutic agent for non-small cell lung cancer, gefitinib and erlotinib as tyrosine kinase inhibitors, and sorafenib and sunitinib as a therapeutic agent of renal cell carcinoma, but they are known to have side effects such as bleeding, heart attack, heart failure, and liver failure.

Recently, anaplastic lymphoma kinase (ALK) has been discovered in various tumors in human bodies and is thus being studied as a target product for target-specific treatments.

The tumorigenesis of ALK has been identified mostly by the study on the fusion gene of anaplastic lymphoma kinase-nucleophosmin (ALK-NPM) observed in anaplastic large cell lymphoma. Once ALK is activated by the gene fusion, the tyrosine kinase possessed by ALK starts to behave abnormally and induces cancer. That is, the abnormally activated ALK induces proliferation of cells, inhibits apoptosis to prevent programmed cell death and rearranges cell frames and changes the shape of cells. The oncogenic conversion of ALK occurs by the interaction with a downstream molecule which is a target material of ALK, wherein the downstream molecule is a material to mediate the intracellular signal transduction. ALK can be connected to other tyrosine kinases, either normal or oncogenically converted ones, and interact therewith, or activate other various kinds of pathways.

In particular, the ALK gene in lung cancer cells fuses with echinoderm microtubule-associated protein-like 4 (EML4) gene and produces EML4-ALK, which is an active form of tyrosine kinase. Here, the oncogenic capability of the EML4-ALK is known to be dependent on enzyme activity, and Mosse et al. have reported amplification of about 26% of the ALK gene in 491 neuroblastoma subjects. Additionally, the ALK gene is known to be expressed in many nonhematopoietic cell tumors such as large B-cell lymphoma, systemic histiocytosis, inflammatory myofibroblastic tumor, esophageal squamous cell carcinoma, non-small cell lung cancer, rhabdomyosarcoma, myofibroblastoma, breast cancer, and melanoma cell line. In the case of the rare disease called inflammatory myelofibroblast tumor, various kinds of ALK fusion proteins are frequently discovered and thus these fusion proteins are believed to be closely associated with the tumorigenesis.

Accordingly, therapeutic agents regarding the ALK-NPM for cancer treatment by blocking the activation pathway of ALK are being developed. Recently, Crizotinib® (PF-02341066), which is a drug developed by Pfizer as a selective inhibitor for tumorigenic mutation and is one of small molecule tyrosine kinase inhibitors, is known to be effective in the treatment of non-small cell lung cancer, and was approved as a new drug by the FDA in 2011.

Additionally, NVP-TAE684 and LDK-378 of Novartis and CH5424802 of Chugai are also known to be effective in reducing tumor size in neuroblastoma cell lines in addition to anaplastic large cell lymphoma.

WO 2009143389, WO 2008051547, WO 2004080980, WO 2012061415, WO 2009145856, US 2009/7589200, US 2009/7517886, and WO 2005016893 indicates that candidate therapeutic materials with various frames for use to inhibit the ALK activity are being developed, and that pyrimidine derivatives selectively inhibit ALK and thus can be developed as an anticancer agent. These compounds, although having both in vitro and in vivo activities, reportedly have problems such as deterioration in selectivity on different kinases such as insulin receptor and side effects in heart.

Meanwhile, activated Cdc42-associated kinase (ACK1), being a non-receptor tyrosine kinase, is a kind of growth-promoting tyrosine kinase gene. ACK1 can activate Cdc42, Rac, and FAK via various signal pathways, and is also known as a device for regulating endocytosis via clathrin.

Recently, active studies have been performed on the correlation between ACK1 and tumorigenesis and metastasis.

First, Mahajan, N. P. discovered that the activity of androgen receptor (AR) generates a castration-resistant prostate cancer, wherein ACK1 performs a phosphorylation with the androgen receptor to increase its activity thereby contributing to the occurrence of cancer (Cancer Res. Vol. 65, (2005) p. 10514; Proc. Natl. Acad. Sci. U.S.A. Vol. 104, (2007) p. 8438). Additionally, van der Horst, E. H. revealed that the overexpression of ACK1 improves the motility of cancer cell lines and invasion capabilities thereby promoting metastasis of cancer (Proc. natl. Acad. Sci. U.S.A. Vol. 1032, (2005) p. 15901). Above all, ACK1 performs a phosphorylation with WW domain containing oxidoreductase (Wwox), which is known to inhibit cancer cells, and the accompanying ubiquitination induces its progress to induce the decomposition of Wwox thereby promoting metastasis of cancer cells while preventing cancer treatment (Cancer Res. Vol. 65, (2005) p. 10514; Cancer res. Vol. 61, (2001) p. 8068).

Therefore, it is apparent that ACK1 is most highly associated with the occurrence and metastasis of cancer, and thus there is an urgent need for the study and development of ACK1 necessary for the prevention and treatment of cancer.

Accordingly, the present inventors, while endeavoring to develop a compound having the inhibitory effect against the ALK, discovered that a N2,N4-bis(4-(piperazin-1-yl)phenyl)pyrimidin-2,4-diamine derivative with a certain structure can act as an inhibitor of the activities of ALK and ACK1, and thereby completed the present invention.

SUMMARY OF THE INVENTION

One object of the present invention is to provide an N2,N4-bis(4-(piperazin-1-yl)phenyl)pyrimidin-2,4-diamine derivative or a pharmaceutically acceptable salt thereof.

Another object of the present invention is to provide a method of preparing an N2,N4-bis(4-(piperazin-1-yl)phenyl)pyrimidin-2,4-diamine derivative or a pharmaceutically acceptable salt thereof.

Still another object of the present invention is to provide a pharmaceutical composition for the prevention or treatment of cancers containing an N2,N4-bis(4-(piperazin-1-yl)phenyl)pyrimidin-2,4-diamine derivative or a pharmaceutically acceptable salt thereof as an active ingredient.

Even another object of the present invention is to provide an ALK inhibitor containing an N2,N4-bis(4-(piperazin-1-yl)phenyl)pyrimidin-2,4-diamine derivative or a pharmaceutically acceptable salt thereof as an active ingredient.

Yet another object of the present invention is to provide an ACK1 inhibitor containing an N2,N4-bis(4-(piperazin-1-yl)phenyl)pyrimidin-2,4-diamine derivative or a pharmaceutically acceptable salt thereof as an active ingredient.

In order to achieve the objects, the present invention provides an N2,N4-bis(4-(piperazin-1-yl)phenyl)pyrimidin-2,4-diamine derivative of Chemical Formula 1 below or a pharmaceutically acceptable salt thereof:

[Chemical Formula 1]

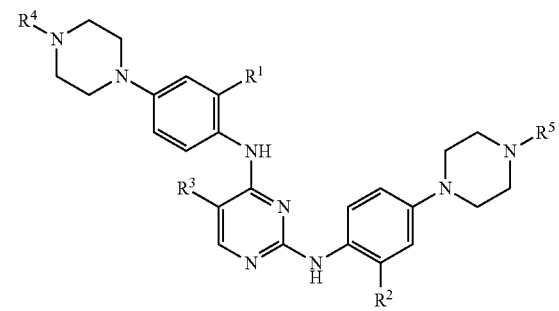

(in Chemical Formula 1, $R^1$ to $R^5$ are the same as defined herein).

Additionally, the present invention provides a method of preparing a compound of Chemical Formula 1 above.

Furthermore, the present invention provides a pharmaceutical composition for the prevention or treatment of cancers containing an N2,N4-bis(4-(piperazin-1-yl)phenyl)pyrimidin-2,4-diamine derivative represented by Chemical Formula 1 above or a pharmaceutically acceptable salt thereof as an active ingredient.

Additionally, the present invention provides an ALK inhibitor containing an N2,N4-bis(4-(piperazin-1-yl)phenyl)pyrimidin-2,4-diamine derivative represented by Chemical Formula 1 above or a pharmaceutically acceptable salt thereof as an active ingredient.

Furthermore, the present invention provides an ACK1 inhibitor containing an N2,N4-bis(4-(piperazin-1-yl)phenyl)pyrimidin-2,4-diamine derivative represented by Chemical Formula 1 above or a pharmaceutically acceptable salt thereof as an active ingredient.

Advantageous Effects

The compound of the present invention has excellent inhibitory effects against the activities of ALK and ACK1 and thus can improve the therapeutic effects on the treatment of cancer cells having ALK fusion proteins such as EML4-ALK and NPM-ALK, and also effectively prevent the recurrence of cancers thus being useful as a pharmaceutical composition for the prevention and treatment of cancers.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
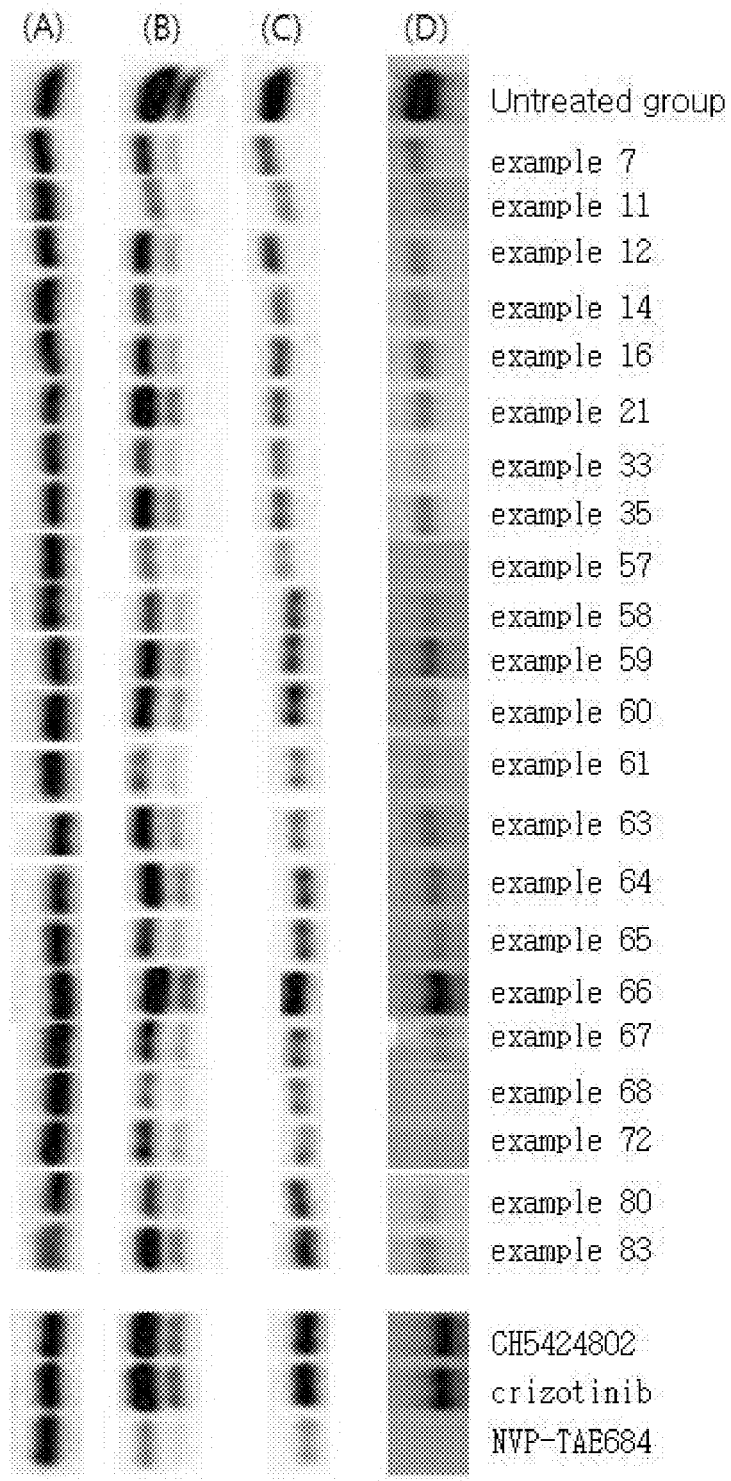
FIG. 1 is a picture showing the phosphorylation inhibitory effect by anaplastic lymphoma kinase (ALK) (A; tubulin protein, B: p-Erk kinase, C: p-Akt kinase, D: p-ALK kinase)

Hereinafter, the present invention will be described in detail.

The present invention provides an N2,N4-bis(4-(piperazin-1-yl)phenyl)pyrimidin-2,4-diamine derivative represented by Chemical Formula 1 below or a pharmaceutically acceptable salt thereof.

[Chemical Formula 1]

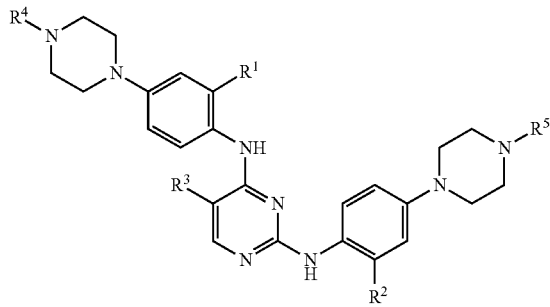

In Chemical Formula 1 above, $R^1$ and $R^2$ are independently H, halogen, —$OR^6$ or —$NR^7R^8$, where $R^6$ is $C_1$-$C_4$ linear or branched alkyl unsubstituted, Or substituted with at least one selected from the group consisting of halogen and $C_5$-$C_6$ aryl, $R^7$ and $R^8$ are independently H, $C_1$-$C_4$ linear or branched alkyl, $C_1$-$C_4$ linear or branched alkylcarbonyl or $C_5$-$C_6$ aryl;

$R^4$ and $R^5$ are independently H; $C_1$-$C_4$ linear or branched alkyl unsubstituted or substituted with hydroxy group; —C(=O)$R^9$ or —$SO_2$—$R^{10}$, where $R^9$ is $C_1$-$C_4$ linear or branched alkyl unsubstituted or substituted with hydroxy group; $C_1$-$C_4$ linear or branched alkyloxy; amino unsubstituted or substituted with $C_1$-$C_4$ linear or branched alkyl, and $R^{10}$ is $C_1$-$C_4$ linear or branched alkyl; amino unsubstituted or substituted with $C_1$-$C_4$ linear or branched alkyl, and $R^3$ is halogen; or $C_1$-$C_4$ linear or branched alkyl substituted with at least one halogen).

Preferably, $R^1$ and $R^2$ are independently H, chloro, bromo, fluoro, —$OR^6$ or —$NR^7R^8$, where $R^6$ is methyl, ethyl, propyl, isopropyl, butyl, isobutyl or t-butyl unsubstituted or substituted with at least one selected from the group consisting of chloro, bromo, fluoro, iodine, and phenyl, $R^7$ and $R^8$ are independently H; methyl; ethyl; propyl; isopropyl; butyl; isobutyl; t-butyl; methylcarbonyl; ethylcarbonyl; propylcarbonyl; isopropylcarbonyl; butylcarbonyl; isobutylcarbonyl or phenyl;

$R^4$ and $R^5$ are independently H; methyl, ethyl, propyl, isopropyl, butyl, isobutyl, t-butyl, —C(=O)$R^9$ or —$SO_2$—$R^{10}$ unsubstituted or substituted with hydroxyl, wherein $R^9$ is methyl, ethyl, propyl, isopropyl, butyl, isobutyl, t-butyl, methyloxy, ethyloxy, propyloxy, isopropyloxy, butyloxy, isobutyloxy, t-butyloxy, hydroxymethyl, hydroxyethyl, hydroxypropyl, hydroxyisopropyl, hydroxybutyl, hydroxyisobutyl, amino, methylamino, ethylamino, propylamino, isopropylamino, butylamino or isobutylamino, $R^{10}$ is methyl, ethyl, propyl, isopropyl, butyl, isobutyl, t-butyl, or amino; and $R^3$ is chloro; bromo; fluoro; iodine; or methyl, ethyl, propyl, isopropyl, butyl, isobutyl or t-butyl substituted from at least one selected from the group consisting of chloro, bromo, fluoro, and iodine.

More preferably, $R^1$ is H, chloro, bromo, fluoro, methoxy, ethoxy, propoxy, isopropoxy, benzyloxy, difluoromethyloxy, dimethylamino, t-butylamino, phenylamino, ethylcarbonylmethylamino or propylcarbonylmethylamino;

$R^2$ is H or methoxy or difluoromethyloxy;

$R^3$ is chloro, fluoro, bromo or trifluoromethyl; and $R^4$ and $R^5$ are independently H, methyl, hydroxyethyl, methylcarbonyl, ethylcarbonyl, t-butylcarbonyl, hydroxymethylcarbonyl, ethylaminocarbonyl, methyloxycarbonyl, t-butyloxycarbonyl, methylsulfonyl or aminosulfonyl.

Additionally, more specific examples of the compound represented by Chemical Formula 1 may be as follows:

(1) 1-(4-(4-(4-(4-(4-acetylpiperazin-1-yl)-2-ethoxyphenylamino)-5-chloropyrimidin-2-ylamino)-3-methoxyphenyl)piperazin-1-yl)ethanone;

(2) 1-(4-(4-(2-(4-(4-acetylpiperazin-1-yl)-2-methoxyphenylamino)-5-chloropyrimidin-4-ylamino)-3-propoxyphenyl)piperazin-1-yl)ethanone;

(3) 1-(4-(4-(4-(4-(4-acetylpiperazin-1-yl)-2-isopropoxyphenylamino)-5-chloropyrimidin-2-ylamino)-3-methoxyphenyl)piperazin-1-yl)ethanone;

(4) 1-(4-(4-(4-(4-(4-acetylpiperazin-1-yl)-2-propoxyphenylamino)-5-chloropyrimidin-2-ylamino)phenyl)piperazin-1-yl)ethanone;

(5) 1,1'-(4,4'-(4,4'-(5-fluoropyrimidin-2,4-diyl)bis(azanediyl)bis(3-methoxy-4,1-phenylene))bis(piperazin-4,1-diyl))diethanone;

(6) 1-(4-(4-(4-(4-(4-acetylpiperazin-1-yl)-2-ethoxyphenylamino)-5-chloropyrimidin-2-ylamino)phenyl)piperazin-1-yl)ethanone;

(7) 1,1'-(4,4'-(4,4'-(5-chloropyrimidin-2,4-diyl)bis(azanediyl)bis(3-methoxy-4,1-phenylene))bis(piperazin-4,1-diyl))diethanone;

(8) 1-(4-(4-(2-(4-(4-acetylpiperazin-1-yl)-2-methoxyphenylamino)-5-chloropyrimidin-4-ylamino)phenyl)piperazin-1-yl)ethanone;

(9) 1,1'-(4,4'-(4,4'-(5-chloropyrimidin-2,4-diyl)bis(azanediyl)bis(4,1-phenylene))bis(piperazin-4,1-diyl))diethanone;

(10) 1-(4-(4-(4-(4-(4-acetylpiperazin-1-yl)-2-methoxyphenylamino)-5-chloropyrimidin-2-ylamino)phenyl)piperazin-1-yl)ethanone;

(11) 1,1'-(4,4'-(4,4'-(5-(trifluoromethyl)pyrimidin-2,4-diyl)bis(azanediyl)bis(3-methoxy-4,1-phenylene))bis(piperazin-4,1-diyl))diethanone;

(12) 1-(4-(4-(5-chloro-4-(2-methoxy-4-(piperazin-1-yl)phenylamino)pyrimidin-2-ylamino)-3-methoxyphenyl)piperazin-1-yl)ethanone;

(13) 1-(4-(4-(5-chloro-4-(2-methoxy-4-(4-(methylsulfonyl)piperazin-1-yl)phenylamino)pyrimidin-2-ylamino)-3-methoxyphenyl)piperazin-1-yl)ethanone;

(14) 1-(4-(4-(2-(4-(4-acetylpiperazin-1-yl)-2-methoxyphenylamino)-5-chloropyrimidin-4-ylamino)-3-methoxyphenyl)piperazin-1-yl)-2-hydroxyethanone;

(15) tert-butyl 4-(4-(2-(4-(4-acetylpiperazin-1-yl)-2-methoxyphenylamino)-5-chloropyrimidin-4-ylamino)-3-methoxyphenyl)piperazin-1-carboxylate;
(16) 1-(4-(4-(5-chloro-4-(4-(4-(2-hydroxyethyl)piperazin-1-yl)-2-methoxyphenylamino)pyrimidin-2-ylamino)-3-methoxyphenyl)piperazin-1-yl)ethanone;
(17) 1-(4-(4-(4-(4-acetylpiperazin-1-yl)-2-(benzyloxy)phenylamino)-5-chloropyrimidin-2-ylamino)-3-methoxyphenyl)piperazin-1-yl)ethanone;
(18) 1,1'-(4,4'-(4,4'-(5-bromopyrimidin-2,4-diyl)bis(azanediyl)bis(3-methoxy-4,1-phenylene))bis(piperazin-4,1-diyl))diethanone;
(19) 1,1'-(4,4'-(4,4'-(pyrimidin-2,4-diylbis(azanediyl))bis(3-methoxy-4,1-phenylene))bis(piperazin-4,1-diyl))diethanone;
(20) methyl 4-(4-(2-(4-(4-acetylpiperazin-1-yl)-2-methoxyphenylamino)-5-chloropyrimidin-4-ylamino)-3-methoxyphenyl)piperazin-1-carboxylate;
(21) 4-(4-(2-(4-(4-acetylpiperazin-1-yl)-2-methoxyphenylamino)-5-chloropyrimidin-4-ylamino)-3-methoxyphenyl)piperazin-1-sulfonamide;
(22) 1-(4-(4-(2-(4-(4-acetylpiperazin-1-yl)-2-methoxyphenylamino)-5-chloropyrimidin-4-ylamino)-3-methoxyphenyl)piperazin-1-yl)propan-1-one;
(23) 1-(4-(4-(2-(4-(4-acetylpiperazin-1-yl)-2-methoxyphenylamino)-5-chloropyrimidin-4-ylamino)-3-methoxyphenyl)piperazin-1-yl)-2,2-dimethylpropan-1-one;
(24) 1-(4-(4-(4-(4-acetylpiperazin-1-yl)-2-methoxyphenylamino)-5-fluoropyrimidin-2-ylamino)phenyl)piperazin-1-yl)ethanone;
(25) tert-butyl 4-(4-(2-(4-(4-acetylpiperazin-1-yl)-2-methoxyphenylamino)-5-fluoropyrimidin-4-ylamino)-3-methoxyphenyl)piperazin-1-carboxylate;
(26) 1-(4-(4-(5-fluoro-4-(2-methoxy-4-(4-(methylsulfonyl)piperazin-1-yl)phenylamino)pyrimidin-2-ylamino)-3-methoxyphenyl)piperazin-1-yl)ethanone;
(27) methyl 4-(4-(2-(4-(4-acetylpiperazin-1-yl)-2-methoxyphenylamino)-5-fluoropyrimidin-4-ylamino)-3-methoxyphenyl)piperazin-1-carboxylate;
(28) 1-(4-(4-(5-fluoro-4-(4-(4-(2-hydroxyethyl)piperazin-1-yl)-2-methoxyphenylamino)pyrimidin-2-ylamino)-3-methoxyphenyl)piperazin-1-yl)ethanone;
(29) 1-(4-(4-(4-(4-acetylpiperazin-1-yl)-2-ethoxyphenylamino)-5-fluoropyrimidin-2-ylamino)-3-methoxyphenyl)piperazin-1-yl)ethanone;
(30) 1-(4-(4-(5-fluoro-4-(2-methoxy-4-(4-methylpiperazin-1-yl)phenylamino)pyrimidin-2-ylamino)-3-methoxyphenyl)piperazin-1-yl)ethanone;
(31) 4-(4-(2-(4-(4-acetylpiperazin-1-yl)-2-methoxyphenylamino)-5-fluoropyrimidin-4-ylamino)-3-methoxyphenyl)-N-ethylpiperazin-1-carboxyamide;
(32) 1-(4-(4-(5-fluoro-4-(2-methoxy-4-(piperazin-1-yl)phenylamino)pyrimidin-2-ylamino)-3-methoxyphenyl)piperazin-1-yl)ethanone;
(33) tert-butyl 4-(4-(2-(4-(4-acetylpiperazin-1-yl)-2-methoxyphenylamino)-5-chloropyrimidin-4-ylamino)-3-(difluoromethoxy)phenyl)piperazin-1-carboxylate;
(34) 1-(4-(4-(5-chloro-4-(2-(difluoromethoxy)-4-(piperazin-1-yl)phenylamino)pyrimidin-2-ylamino)-3-methoxyphenyl)piperazin-1-yl)ethanone;
(35) 1-(4-(4-(4-(4-acetylpiperazin-1-yl)-2-(difluoramethoxy)phenylamino)-5-chloropyrimidin-2-ylamino)-3-methoxyphenyl)piperazin-1-yl)ethanone;
(36) 1-(4-(4-(2-(4-(4-acetylpiperazin-1-yl)-2-methoxyphenylamino)-5-fluoropyrimidin-4-ylamino)-3-methoxyphenyl)piperazin-1-yl)-2-hydroxyethanone;
(37) 1-(4-(4-(4-(2-(difluoromethoxy)-4-(piperazin-1-yl)phenylamino)-5-fluoropyrimidin-2-ylamino)-3-methoxyphenyl)piperazin-1-yl)ethanone;
(38) 1-(4-(4-(4-(2-(difluoromethoxy)-4-(4-methylpiperazin-1-yl)phenylamino)-5-fluoropyrimidin-2-ylamino)-3-methoxyphenyl)piperazin-1-yl)ethanone;
(39) tert-butyl 4-(4-(2-(4-(4-acetylpiperazin-1-yl)-2-methoxyphenylamino)-5-(fluoropyrimidin-4-ylamino)-3-(difluoromethoxy)phenyl)piperazin-1-carboxylate;
(40) 1-(4-(4-(4-(2-(difluoramethoxy)-4-(methylsulfonyl)piperazin-1-yl)phenylamino)-5-fluoropyrimidin-2-ylamino)-3-methoxyphenyl)piperazin-1-yl)ethanone;
(41) methyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate;
(42) 1-(4-(4-(4-(2-(difluoromethoxy)-4-(2-hydroxyethyl)piperazin-1-yl)phenylamino)-5-fluoropyrimidin-2-ylamino)-3-methoxyphenyl)piperazin-1-yl)ethanone;
(43) 4-(4-(2-(4-(4-acetylpiperazin-1-yl)-2-methoxyphenylamino)-5-fluoropyrimidin-4-ylamino)-3-(difluoromethoxy)phenyl)-N-ethylpiperazin-1-carboxyamide;
(44) 1-(4-(4-(2-(4-(4-acetylpiperazin-1-yl)-2-methoxyphenylamino)-5-fluoropyrimidin-4-ylamino)-3-(difluoromethoxy)phenyl)piperazin-1-yl)-2-hydroxyethanone;
(45) 1-(4-(4-(2-(4-(4-acetylpiperazin-1-yl)-2-methoxyphenylamino)-5-fluoropyrimidin-4-ylamino)-3-(difluoromethoxy)phenyl)piperazin-1-yl)ethanone;
(46) 1-(4-(4-(4-(4-acetylpiperazin-1-yl)-2-(tert-butylamino)phenylamino)-5-chloropyrimidin-2-ylamino)-3-methoxyphenyl)piperazin-1-yl)ethanone;
(47) 1-(4-(4-(4-(4-acetylpiperazin-1-yl)-2-(phenylamino)phenylamino)-5-chloropyrimidin-2-ylamino)-3-methoxyphenyl)piperazin-1-yl)ethanone;
(48) tert-butyl 4-(4-(2-(4-(4-acetylpiperazin-1-yl)-2-methoxyphenylamino)-5-chloropyrimidin-4-ylamino)-3-(N-methylpropionamido)phenyl)piperazin-1-carboxylate;
(49) tert-butyl 4-(4-(2-(4-(4-acetylpiperazin-1-yl)-2-methoxyphenylamino)-5-chloropyrimidin-4-ylamino)-3-(N-methylbutylamido)phenyl)piperazin-1-carboxylate;
(50) N-(2-(2-(4-(4-acetylpiperazin-1-yl)-2-methoxyphenylamino)-5-chloropyrimidin-4-ylamino)-5-(piperazin-1-yl)phenyl)-N-methylpropionamide;
(51) N-(2-(2-(4-(4-acetylpiperazin-1-yl)-2-methoxyphenylamino)-5-chloropyrimidin-4-ylamino)-5-(piperazin-1-yl)phenyl)-N-methylbutylamide;
(52) tert-butyl 4-(4-(2-(4-(4-acetylpiperazin-1-yl)-2-methoxyphenylamino)-5-chloropyrimidin-2-ylamino)-3-methoxyphenyl)piperazin-1-carboxylate;
(53) N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylpropionamide;
(54) N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylbutylamide;
(55) tert-butyl-4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-carboxylate;
(56) 1-(4-(3-methoxy-4-((4-((2-methoxy-4-(piperazin-1-yl)phenyl)amino)-5-(trifluoromethyl)pyrimidin-2-yl)amino)phenyl)piperazin-1-yl)ethanone;
(57) 4-(4-((2-((4-(4-acetylpiperazin-1-yl)-2-methoxyphenyl)amino)-5-(trifluoromethyl)pyrimidin-4-yl)amino)-3-methoxyphenyl)-N-ethylpiperazin-1-carboxyamide;
(58) 1-(4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-yl)-2-hydroxyethanone;

(59) 1-(4-(3-methoxy-4-((4-((2-methoxy-4-(4-methoxypiperazin-1-yl)phenyl)amino)-5-(trifluoromethyl)pyrimidin-2-yl)amino)phenyl)piperazin-1-yl)ethanone;
(60) N-(4-(3-methoxy-4-((4-((2-methoxy-4-(4-(methylsulfonyl)piperazin-1-yl)phenyl)amino)-5-(trifluoromethyl) pyrimidin-2-yl)amino)phenyl)piperazin-1-yl)ethanone;
(61) 1-(4-(4-((4-((4-(4-(2-hydroxyethyl)piperazin-1-yl)-2-methoxyphenyl)amino)-5-(trifluoromethyl)pyrimidin-2-yl)amino)-3-methoxyphenyl)piperazin-1-yl)ethanone;
(62) tert-butyl-4-(4-((4-((4-(4-acetylpiperazin-1-yl)-2-methoxyphenyl)amino)-5-(trifluoramethyl)pyrimidin-2-yl) amino)-3-methoxyphenyl)piperazin-1-carboxylate;
(63) 1-(4-(3-methoxy-4-((2-((2-methoxy-4-(piperazin-1-yl) phenyl)amino)-5-(trifluoromethyl)pyrimidin-4-yl)amino) phenyl)piperazin-1-yl)ethanone;
(64) 4-(4-((4-((4-(4-acetylpiperazin-1-yl)-2-methoxyphenyl)amino)-5-(trifluoromethyl)pyrimidin-2-yl)amino)-3-methoxyphenyl)-N-ethylpiperazin-1-carboxylate;
(65) 1-(4-(4-((4-((4-(4-acetylpiperazin-1-yl)-2-methoxyphenyl)amino)-5-(trifluoromethyl)pyrimidin-2-yl)amino)-3-methoxyphenyl)piperazin-1-yl)-2-hydroxyethanone;
(66) 1-(4-(3-methyl-4-((2-((-methoxy-4-(4-methylpiperazin-1-yl)phenyl)amino)-5-(trifluoromethyl)pyrimidin-4-yl)amino)phenyl)piperazin-1-yl)ethanone;
(67) 1-(4-(3-methoxy-4-((2-((2-methoxy-4 (4-(methylsulfonyl)piperazin-1-yl-phenyl)amino)-5-(trifluoromethyl)pyrimidin-4-yl)amino)phenyl)piperazin-1-yl)ethanone;
(68) 1-(4-(4-((2-((4-(4-(2-hydroxyethyl)piperazin-1-yl)-2-methoxyphenyl)amino)-5-(trifluoromethyl)pyrimidin-4-yl)amino)-3-methoxyphenyl)piperazin-1-yl)ethanone;
(69) N2,N4-bis(2-methoxy-4-(piperazin-1-yl)phenyl)-5-(trifluoromethyl)pyrimidin-2,4-diamine;
(70) 4,4'-(((5-trifluoromethyl)pyrimidin-2,4-diyl)bis (azanediyl))bis(3-methoxy-4,1-phenylene))bis(piperazin-1-carboxylate);
(71) 4,4'-(((5-trifluoromethyl)pyrimidin-2,4-diyl)bis (azanediyl))bis(3-methoxy-4,1-phenylene))bis(N-ethylpiperazin-1-carboxyamide);
(72) 4,4'-(((5-(trifluoromethyl)pyrimidin-2,4-diyl)bis (azanediyl))bis(3-methoxy-4,1-phenylene))bis(N-ethylpiperazin-1-carboxyamide);
(73) 1,1'-(4,4'-(((5-(trifluoromethyl)pyrimidin-2,4-diyl)bis (azanediyl))bis(3-difluoromethoxy)-4,1-phenylene))bis (piperazin-4,1-diyl))diethanone;
(74) 1-(4-(4-((4-((4-(4-acetylpiperazin-1-yl)-2-chlorophenyl)amino)-5-chloropyrimidin-2-yl)amino)-3-methoxyphenyl)piperazin-1-yl)ethanone;
(75) 1,1'-(4,4'-(((5-chloropyrimidin-2,4-diyl)bis(azanediyl)) bis(3-chloro-4,1-phenylene))bis(piperazin-4,1-diyl)diethanone;
(76) 1-(4-(4-((2-((4-(4-acetylpiperazin-1-yl)-2-methoxyphenyl)amino)-5-chloropyrimidin-4-yl)amino)-3-phenoxyphenyl)piperazin-1-yl)ethanone;
(77) 5-chloro-N2-N4-bis(2-methoxy-4-(piperazin-1-yl)phenyl)pyrimidin-2,4-diamine;
(78) 4,4'-(((5-chloropyrimidin-2,4-diyl)bis(azanediyl))bis (3-methoxy-4,1-phenylene))bis(N-ethylpiperazin-1-carboxyamide);
(79) 5-chloro-N2,N4-bis(2-methoxy-4-(4-(methylsulfonyl) piperazin-1-yl)phenyl)pyrimidin-2,4-diamine;
(80) 1,1'-(4,4'-(((5-chloropyrimidin-2,4-diyl)bis(azanediyl)) bis(3-methoxy-4,1-phenylene)bis(piperazin-4,1-diyl))bis (2-hydroxyethanone);
(81) 1-(4-(4-((5-chloro-4-((2-fluoro-4-(piperazin-1-yl)phenyl)amino)pyrimidin-2-yl)amino)-3-methoxyphenyl)piperazin-1-yl)ethanone;
(82) 1-(4-(4-((4-((4-acetylpiperazin-1-yl)-2-fluorophenyl) amino)-5-chloropyrimidin-2-yl)amino)-3-methoxyphenyl)piperazin-1-yl)ethanone;
(83) 1-(4-(4-((4-((4-acetylpiperazin-1-yl)-2-methoxyphenyl)amino)-5-chloropyrimidin-2-yl)amino)-3-methoxyphenyl)piperazin-1-yl)-2-hydroxyethanone;
(84) methyl-4-(4-((4-((4-(4-acetylpiperazin-1-yl)-2-methoxyphenyl)amino)-5-chloropyrimidin-2-yl)amino)-3-methoxyphenyl)piperazin-1-carboxylate;
(85) 1-(4-(4-((5-chloro-2-((4-(4-(2-hydroxyethyl)piperazin-1-yl)-2-methoxyphenyl)amino)pyrimidin-4-yl)amino)-3-methoxyphenyl)piperazin-1-yl)ethanone;
(86) 4-(4-((4-((4-(4-acetylpiperazin-1-yl)-2-methoxyphenyl)amino)-5-chloropyrimidin-2-yl)amino)-3-methoxyphenyl)piperazin-1-sulfonamide;
(87) 1-(4-(4-((5-chloro-2-((2-methoxy-4-(4-(methylsulfonyl)piperazin-1-yl)phenyl)amino)pyrimidin-4-yl)amino)-3-methoxyphenyl)piperazin-1-yl)ethanone;
(88) 1-(4-(4-((2-((4-(4-acetylpiperazin-1-yl)-2-methoxyphenyl)amino)-5-chloropyrimidin-4-yl)amino)-3-(difluoromethoxy)phenyl)piperazin-1-yl)-2-hydroxyethanone; and
(89) 1-(4-(3-(difluoromethoxy)-4-(5-fluoro-2-(2-methoxy-4-(piperazin-1-yl)phenylamino)pyrimidin-4-ylamino) phenyl)piperazin-1-yl)ethanone.

The N2,N4-bis(4-(piperazin-1-yl)phenyl)pyrimidin-2,4-diamine derivative represented by Chemical Formula 1 above of the present invention may be used in the form of a pharmaceutically acceptable salt, and as a salt, an acid addition salt formed by a pharmaceutically acceptable free acid is useful. The acid addition salt was obtained from inorganic acids such as hydrochloric acid, nitric acid, phosphoric acid, sulfuric acid, hydrobromic acid, hydriodic acid, nitrous acid, or phosphorous acid, aliphatic mono and dicarboylate, phenyl-substituted alkanoate, hydroxy alkanoate and alkanedioate, aromatic acids, non-toxic organic acids such as aliphatic and aromatic sulfonic acids, and organic acid such as acetic acid, benzoic acid, citric acid, lactic acid, maleic acid, gluconic acid, methane sulfonic acids, 4-toluenesulfonic acid, tartaric acid, and fumaric acid. Examples of such pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butin-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate or mandelate.

The acid addition salt of the present invention may be prepared by a conventional method, for example, by dissolving N2,N4-bis(4-(piperazin-1-yl)phenyl)pyrimidin-2,4-diamine derivative represented by Chemical Formula 1 in an organic solvent such as methanol, ethanol, acetone, methylene chloride, and acetonitrile, adding with an organic acid or inorganic acid, filtering the resulting precipitate followed by drying, or may be prepared by distillation of the solvent and excess acid under reduced pressure followed by drying or by crystallization under an organic solvent.

Additionally, the present invention not only includes the N2,N4-bis(4-(piperazin-1-yl)phenyl)pyrimidin-2,4-diamine derivative represented by Chemical Formula 1 or a pharmaceutically acceptable salt thereof but also a solvate, a hydrate, etc., that can be manufactured therefrom.

Additionally, the present invention provides a method of preparing the N2,N4-bis(4-(piperazin-1-yl)phenyl)pyrimidin-2,4-diamine derivative represented by Chemical Formula 1 above.

Preparation Method 1

A method of preparing the derivative of Chemical Formula according to the present invention is, is as shown in Reaction Scheme 1 below, wherein the method of preparing N2,N4-bis(4-(piperazin-1-yl)phenyl)pyrimidin-2,4-diamine derivative of Chemical Formula 1 or a pharmaceutically acceptable salt thereof, includes:

preparing a compound of Chemical Formula 4 by reacting the chloro group at position 4 of the compound represented by Chemical Formula 2 with the amino group of the compound represented by Chemical Formula 3 (Step 1); and preparing a compound of Chemical Formula 1 by reacting the chloro group at position 2 of pyrimidine of the compound represented by Chemical Formula 4 obtained in Step 1 with the compound represented by Chemical Formula 5 (Step 2), Preparation Method 2

Another method of preparing the derivative of Chemical Formula 1 according to the present invention is, as shown in Reaction Scheme 2 below, a method of preparing N2,N4-bis (4-(piperazin-1-yl)phenyl)pyrimidin-2,4-diamine derivative or a pharmaceutically acceptable salt thereof, by reacting the chloro group of the compound represented by Chemical Formula 2 with at least 2 equivalents of the amino group of the compound represented by Chemical Formula 3 thereby preparing a compound of Chemical Formula 1a:

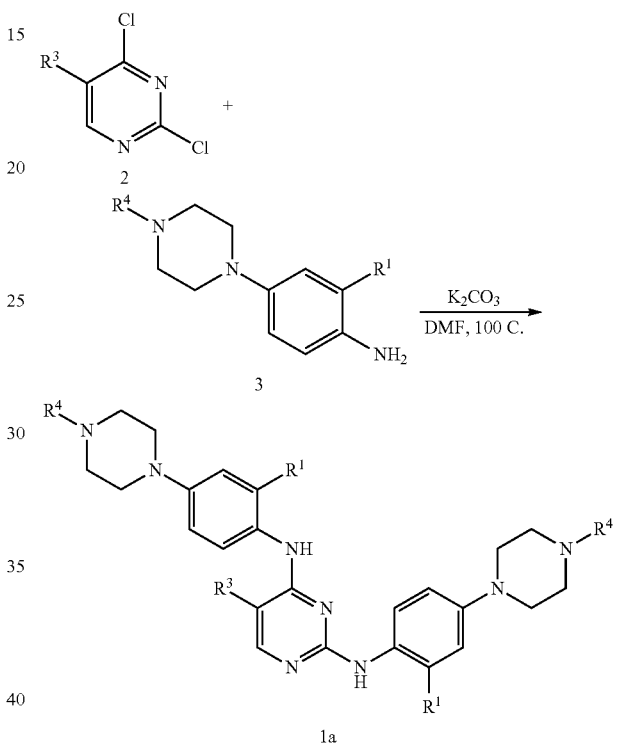

(in Reaction Scheme 2, $R^1$, $R^3$ and $R^4$ are the same as defined in Chemical Formula 1 of claim 1; and the compound of Chemical Formula 1a is the compound of Chemical Formula 1).

Furthermore, the present invention provides a pharmaceutical composition for the prevention or treatment of cancers containing an N2,N4-bis(4-(piperazin-1-yl)phenyl)pyrimidin-2,4-diamine derivative of Chemical Formula 1 above or a pharmaceutically acceptable salt thereof as an active ingredient.

When the composition of the present invention is used as a medicinal drug, the pharmaceutical composition containing an N2,N4-bis(4-(piperazin-1-yl)phenyl)pyrimidin-2,4-diamine derivative represented by Chemical Formula 1 or a pharmaceutically acceptable salt thereof as an active ingredient may be prepared into various oral or parenteral formulations for clinical administration, but is not limited thereto.

Examples of the formulations for oral administration include tablets, pills, hard/soft capsules, liquids, suspensions, emulsions, syrups, granules, elixirs, troches, etc., and they contain, in addition to the active ingredient, a diluent (e.g., lactose, dextrose, sucrose, mannitol, sorbitol, cellulose and/or glycine), a glidant (e.g., silica, talc, stearic acid and its magnesium or calcium salt and/or polyethylene glycol). Tab-

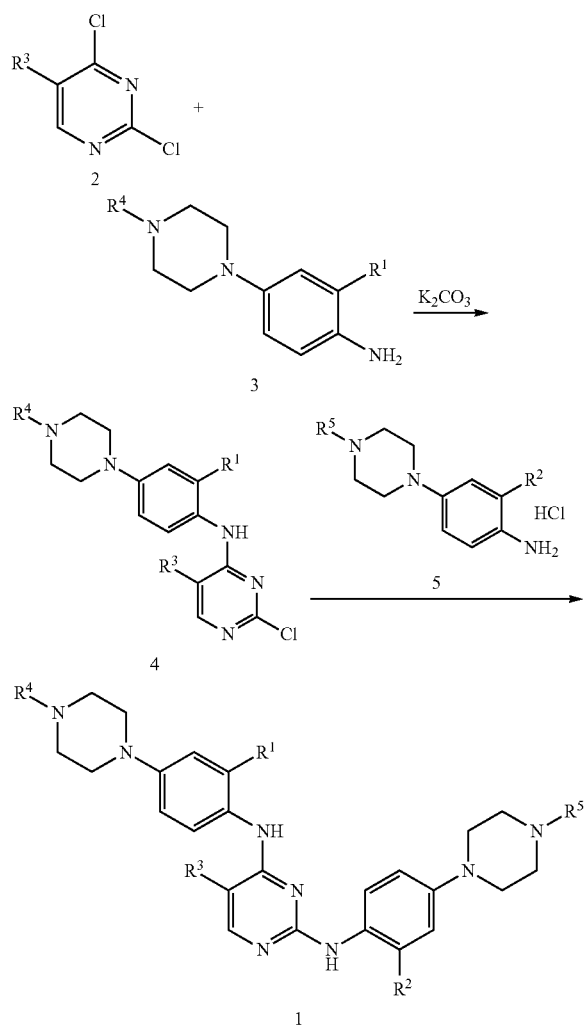

(in Reaction Scheme 1, $R^1$ to $R^5$ are the same as defined in Chemical Formula 1 in claim 1).

lets may further contain a binder such as aluminum silicate, starch paste, gelatin, methyl cellulose, sodium carboxymethylcellulose and/or polyvinylpyrrolidine, and as necessary, may contain a disintegrant such as starch, agar, alginic acid or its sodium salt or an azeotropic mixture and/or an absorbent, a coloring agent, a flavoring agent and a sweetener.

The pharmaceutical composition containing the N2,N4-bis(4-(piperazin-1-yl)phenyl)pyrimidin-2,4-diamine derivative represented by Chemical Formula 1 above as an active ingredient may be administered parenterally, and the parenteral administration will be performed via subcutaneous injection, intravenous injection, intramuscular injection or intrathoracic injection.

In particular, for the preparation of parenteral formulations, the N2,N4-bis(4-(piperazin-1-yl)phenyl)pyrimidin-2,4-diamine derivative of Chemical Formula 1 above or a pharmaceutically acceptable salt thereof may be mixed with a stabilizer or a buffer to prepare it as a solution or suspension, and prepare it in a unit formulation for administration in the form of an ampoule or vial.

The composition may contain a preservative, a stabilizer, wettable powder, or emulsion promoter, a salt for controlling osmosis and/or an adjuvant such as a buffer, and other therapeutically useful materials, and may be formulated according to the conventional method of mixing, granulation or coating method.

The dose of the pharmaceutical composition containing the N2,N4-bis(4-(piperazin-1-yl)phenyl)pyrimidin-2,4-diamine derivative represented by Chemical Formula 1 as an active ingredient to humans may vary depending on the age, body weight, sex, administration type, health status and severity of the disease of a patient, and preferably in the amount from 0.01 to 1000 mg/kg/day, and according to the decision of a doctor or pharmacist, it may be administered a few times daily at regular intervals, preferably once or three times daily via an oral or parenteral route.

The pharmaceutical composition according to the present invention is a pharmaceutical composition for the prevention or treatment of cancer by inhibiting the expression and growth of cancer cells via inhibition of the activity of anaplastic lymphoma kinase (ALK).

ALK is a gene present in cancer cells which induces proliferation of cancer cells, and activated by a process of gene fusion, in which the tyrosine kinase possessed by the ALK behaves abnormally, prevents apoptosis to prevent programmed cell death and rearranges cell frames and changes the shape of cells. Additionally, ALK can be connected to other tyrosine kinases, either normal or oncogenically converted ones, and interact therewith, or activate other various kinds of pathways.

Accordingly, in order to examine the inhibitory activity of the N2,N4-bis(4-(piperazin-1-yl)phenyl)pyrimidin-2,4-diamine derivative represented by Chemical Formula 1 above against ALK activity, the compounds of the present invention were treated with ALK enzyme, and their $IC_{50}$ were measured. The result revealed that about 70% of the compounds among the N2,N4-bis(4-(piperazin-1-yl)phenyl)pyrimidin-2,4-diamine derivatives represented by Chemical Formula 1 exhibited inhibitory activities even at a low concentration of from 0.008 µM to 0.036 µM (see Experimental Example 1).

The result indicates that ALK activity can be effectively inhibited. Additionally, it has a superior inhibitory activity to that of Crizotinib® (0.036 µM, positive control group), which is used as a therapeutic agent for non-small cell lung cancer.

Accordingly, the compounds of the present invention can be used as a pharmaceutical composition for the prevention and treatment of cancer by inhibiting the activity of ALK.

Additionally, the pharmaceutical composition of the present invention is a pharmaceutical composition for the prevention or treatment of cancer by inhibiting the expression and growth of cancer cells via inhibition of the activity of activated Cdc42-assdociated kinase (ACK1).

ACK1 not only removes WW domain containing oxidoreductase (WWwox), which is known as a cancer inhibitory enzyme but also promotes cancer metastasis, and activates androgen receptors which cause prostate cancer.

Accordingly, in order to examine the inhibitory activity of the N2,N4-bis(4-(piperazin-1-yl)phenyl)pyrimidin-2,4-diamine derivative represented by Chemical Formula 1 above against the ACK1 activity, the compounds of the present invention were treated with ACK1, and their inhibitory activities were measured. The result revealed that when most of the compounds were at 0.1 µM the activity of ACK1 was reduced to 10% or below. In particular, in the case of the compounds prepared in Examples 13, 21, 26, 66, 74, 77, 79, and 80, the ACK1 activity was significantly reduced to 0% (see Experimental Example 2).

The above results indicate that the N2,N4-bis(4-(piperazin-1-yl)phenyl)pyrimidin-2,4-diamine derivative of the present invention has an excellent inhibitory activity even at a low concentration against the ACK1 activity. Accordingly, the compounds of the present invention can be used as a useful pharmaceutical composition for the prevention and treatment of cancer by inhibiting the activity of ACK1.

The N2,N4-bis(4-(piperazin-1-yl)phenyl)pyrimidin-2,4-diamine derivatives of Chemical Formula 1 according to the present invention can be used for the prevention and treatment of cancer by inhibiting the activities of ALK and ACK1. Preferably, the cancer may include, for example, non-small cell lung cancer, neuroblastoma, inflammatory myofibroblast tumor, rhabdomyosarcoma, myofibroblastoma, breast cancer, stomach cancer, lung cancer, melanoma, large B-cell lymphoma, systemic histiocytosis, inflammatory myofibroblastic tumor, esophageal squamous cell carcinoma, uterine cancer, prostate cancer, etc.

Furthermore, the N2,N4-bis(4-(piperazin-1-yl)phenyl)pyrimidin-2,4-diamine derivative of Chemical Formula or a pharmaceutically acceptably salt thereof has an excellent inhibitory activity against the ALK activity, and thus it can be used as a useful inhibitor of ALK.

Additionally, the N2,N4-bis(4-(piperazin-1-yl)phenyl)pyrimidin-2,4-diamine derivative of Chemical Formula or a pharmaceutically acceptably salt thereof has an excellent inhibitory activity against the ACK1 activity, and thus it can be used as a useful inhibitor of ACK1.

DETAILS OF THE INVENTION

The method of preparing N2,N4-bis(4-(piperazin-1-yl)phenyl)pyrimidin-2,4-diamine derivatives of Chemical Formula 1 above of the present invention will be explained in detail with reference to Preparation Examples or Examples herein below.

The Preparation Examples or Examples provided below are for illustrative purposes only as embodiments for preparing the N2,N4-bis(4-(piperazin-1-yl)phenyl)pyrimidin-2,4-diamine derivatives of Chemical Formula 1 above and should not be construed as limiting the scope of the present invention.

Additionally, the preparation method explained in the Preparation Examples or Examples may employ synthesis conditions, suitable reagents, etc., well known in the art of organic synthesis.

Preparation Example 1

Preparation of 1-(4-(4-amino-3-methoxyphenyl)piperazin-1-yl)ethanone

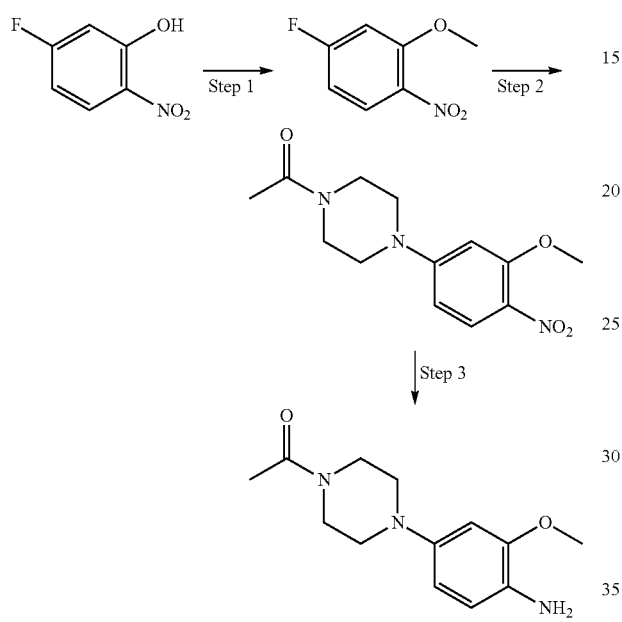

Step 1: Preparation of 4-fluoro-2-methoxy-1-nitrobenzene 5-fluoro-2-nitrophenol (300 mg), methyliodide (0.50 mL) and potassium carbonate (500 mg) were dissolved in dimethylformamide (DMF, 3 mL), and reacted at 50° C. overnight. The dimethylformamide of the reaction mixture was concentrated under reduced pressure, added with water and the organic layer was extracted with ethyl acetate. The organic layer was washed with brine, and the water was removed with sodium sulfate, and the solvent was removed under reduced pressure. The thus obtained compound was used in the subsequent reaction without further purification.

Step 2: Preparation of 1-(4-(3-methoxy-4-nitrophenyl)piperazin-1-yl)ethanone The compound obtained in Step 1 above (300 mg), N-acetylpiperazine (300 mg), and potassium carbonate (500 mg) were dissolved in dimethylformamide (3 mL) and reacted at 80° C. overnight. The dimethylformamide of the reaction mixture was removed under reduced pressure, and added with water to form a solid. The solid was filtered to obtain a target compound as a yellow solid.

$^1$H-NMR (300 MHz, CDCl$_3$) δ 8.00 (d, J=9.1 Hz, 1H), 6.42 (d, J=9.1 Hz, 1H), 6.32 (s, 1H), 3.96 (s, 3H), 3.80-3.79 (m, 2H), 3.67-3.65 (m, 2H), 3.47-3.40 (m, 4H), 2.15 (s, 3H);

Mass (M+H$^+$) calcd for C$_{13}$H$_{17}$N$_3$O$_4$ 279.12. found 279.20

Step 3: Preparation of 1-(4-(4-amino-3-methoxyphenyl)piperazin-1-yl)ethanone The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

$^1$H-NMR (300 MHz, CDCl$_3$) δ 6.65 (d, J=8.6 Hz, 1H), 6.51 (s, 1H), 6.41 (d, J=8.4 Hz, 1H), 3.88 (s, 3H), 3.76 (s, 4H), 3.59 (s, 4H), 2.13 (s, 3H).

Preparation Example 2

Preparation of 1-(4-(4-amino-3-ethoxyphenyl)piperazin-1-yl)ethanone

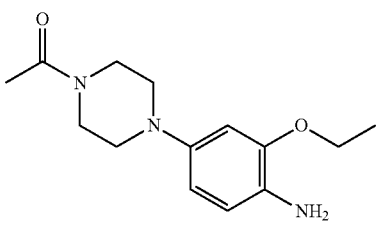 [SMILES: CCOc1cc(N2CCN(C(C)=O)CC2)ccc1N]

Step 1: Preparation of 4-fluoro-2-ethoxy-1-nitrobenzene 5-fluoro-2-nitrophenol (300 mg), ethyliodide (0.50 mL) and potassium carbonate (500 mg) were dissolved in dimethylformamide (DMF, 3 mL), and reacted at 50° C. overnight. The dimethylformamide of the reaction mixture was concentrated under reduced pressure, added with water and the organic layer was extracted with ethyl acetate. The organic layer was washed with brine, and the water was removed with sodium sulfate, and the solvent was removed under reduced pressure. The thus obtained compound was used in the subsequent reaction without further purification.

Step 2: Preparation of 1-(4-(3-ethoxy-4-nitrophenyl)piperazin-1-yl)ethanone

The compound obtained in Step 1 above (300 mg), N-acetylpiperazine (300 mg), and potassium carbonate (500 mg) were dissolved in dimethylformamide (3 mL) and reacted at 80° C. overnight. The dimethylformamide of the reaction mixture was removed under reduced pressure, and added with water to form a solid. The solid was filtered to obtain a target compound as a yellow solid.

$^1$H-NMR (300 MHz, CDCl$_3$) δ 7.97 (d, J=9.3 Hz, 1H), 6.40 (dd, J=2.5, 9.3 Hz, 1H), 6.32 (d, J=2.5 Hz, 1H), 4.15 (q, J=7.0 Hz, 2H), 3.79 (m, 2H), 3.66 (m, 2H), 3.40 (m, 4H), 2.15 (s, 3H), 1.50 (t, J=7.0 Hz, 3H).

Step 3: Preparation of 1-(4-(4-amino-3-ethoxyphenyl)piperazin-1-yl)ethanone

The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

Preparation Example 3

Preparation of 1-(4-(4-amino-3-propoxyphenyl)piperazin-1-yl)ethanone

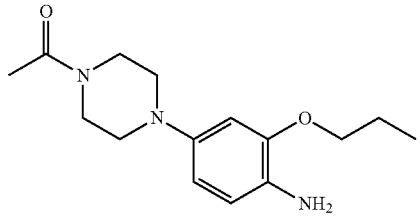 [SMILES: CCCOc1cc(N2CCN(C(C)=O)CC2)ccc1N]

Step 1: Preparation of 4-fluoro-2-propoxy-1-nitrobenzene 5-fluoro-2-nitrophenol (300 mg), n-propyl iodide (0.50 ml) and potassium carbonate (500 mg) were dissolved in dimethylformamide (DMF, 3 mL) and reacted at 50° C. overnight. The dimethylformamide of the reaction mixture was concentrated under reduced pressure, added with water and the organic layer was extracted with ethyl acetate. The organic layer was washed with brine, and the water was removed with sodium sulfate, and the solvent was removed under reduced pressure. The thus obtained compound was used in the subsequent reaction without further purification.

Step 2: Preparation of 1-(4-(3-propoxy-4-nitrophenyl)piperazin-1-yl)ethanone The compound obtained in Step 1 above (300 mg), N-acetylpiperazine (300 mg), and potassium carbonate (500 mg) were dissolved in dimethylformamide (3 mL) and reacted at 80° C. overnight. The dimethylformamide of the reaction mixture was removed under reduced pressure, and added with water to form a solid. The solid was filtered to obtain a target compound as a yellow solid.

$^1$H-NMR (300 MHz, CDCl$_3$) δ 7.98 (d, J=9.3 Hz, 1H), 6.40 (dd, J=2.5, 9.3 Hz, 1H), 6.32 (d, J=2.5 Hz, 1H), 4.03 (t, J=6.4 Hz, 2H), 3.79 (m, 2H), 3.66 (m, 2H), 3.40 (m, 4H), 2.15 (s, 3H), 1.89 (m, 2H), 1.09 (t, J=7.4 Hz, 3H).

Step 3: Preparation of 1-(4-(4-amino-3-propoxyphenyl)piperazin-1-yl)ethanone The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

Preparation Example 4

Preparation of 1-(4-(4-amino-3-isopropoxyphenyl)piperazin-1-yl)ethanone

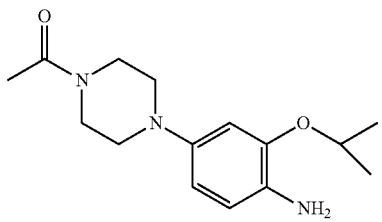 [SMILES: CC(=O)N1CCN(c2ccc(N)c(OC(C)C)c2)CC1]

Step 1: Preparation of 4-fluoro-2-isopropoxy-1-nitrobenzene 5-fluoro-2-nitrophenol (300 mg), isopropyl iodide (0.50 mL) and potassium carbonate (500 mg) were dissolved in dimethylformamide (DMF, 3 mL) and reacted at 50° C. overnight. The dimethylformamide of the reaction mixture was concentrated under reduced pressure, added with water and the organic layer was extracted with ethyl acetate. The organic layer was washed with brine, and the water was removed with sodium sulfate, and the solvent was removed under reduced pressure. The thus obtained compound was used in the subsequent reaction without further purification.

Step 2: Preparation of 1-(4-(3-isopropoxy-4-nitrophenyl)piperazin-1-yl)ethanone The compound obtained in Step 1 above (300 mg), N-acetylpiperazine (300 mg), and potassium carbonate (500 mg) were dissolved in dimethylformamide (3 mL) and reacted at 80° C. overnight. The dimethylformamide of the reaction mixture was removed under reduced pressure, and added with water to form a solid. The solid was filtered to obtain a target compound as a yellow solid.

$^1$H-NMR (300 MHz, CDCl$_3$) δ 7.95 (d, J=9.3 Hz, 1H), 6.42 (dd, J=2.5, 9.3 Hz, 1H), 6.36 (d, J=2.5 Hz, 1H), 4.61 (d, J=6.1 Hz, 1H), 3.79 (m, 2H), 3.65 (m, 2H), 3.42 (m, 4H), 2.15 (s, 3H), 1.41 (d, J=6.1 Hz, 6H).

Step 3: Preparation of 1-(4-(4-amino-3-isopropoxyphenyl)piperazin-1-yl)ethanone The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

Preparation Example 5

Preparation of 1-(4-(4-amino-3-benzyloxyphenyl)piperazin-1-yl)ethanone

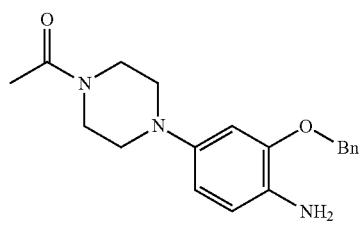 [SMILES: CC(=O)N1CCN(c2ccc(N)c(OCc3ccccc3)c2)CC1]

Step 1: Preparation of 4-fluoro-2-benzyloxy-1-nitrobenzene 5-fluoro-2-nitrophenol (300 mg), benzyl iodide (0.50 mL) and potassium carbonate (500 mg) were dissolved in dimethylformamide (DMF, 3 mL) and reacted at 50° C. overnight. The dimethylformamide of the reaction mixture was concentrated under reduced pressure, added with water and the organic layer was extracted with ethyl acetate. The organic layer was washed with brine, and the water was removed with sodium sulfate, and the solvent was removed under reduced pressure. The thus obtained compound was used in the subsequent reaction without further purification.

Step 2: Preparation of 1-(4-(3-benzyloxy-4-nitrophenyl)piperazin-1-yl)ethanone The compound obtained in Step 1 above (300 mg), N-acetylpiperazine (300 mg), and potassium carbonate (500 mg) were dissolved in dimethylformamide (3 mL) and reacted at 80° C. overnight. The dimethylformamide of the reaction mixture was removed under reduced pressure, and added with water to form a solid. The solid was filtered to obtain a target compound as a yellow solid.

$^1$H-NMR (300 MHz, CDCl$_3$) δ 8.02 (d, J=9.3 Hz, 1H), 7.4 (m, 5H), 6.42 (dd, J=2.5, 9.3 Hz, 1H), 6.35 (d, J=2.5 Hz, 1H), 5.23 (s, 2 h), 3.77 (m, 2H), 3.77 (m, 2H), 3.63 (m, 2H), 3.36 (m, 4H), 2.15 (s, 3H).

Step 3: Preparation of 1-(4-(4-amino-3-benzyloxyphenyl)piperazin-1-yl)ethanone The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

Preparation Example 6

Preparation of 1-(4-(4-amino-3-chlorophenyl)piperazin-1-yl)ethanone

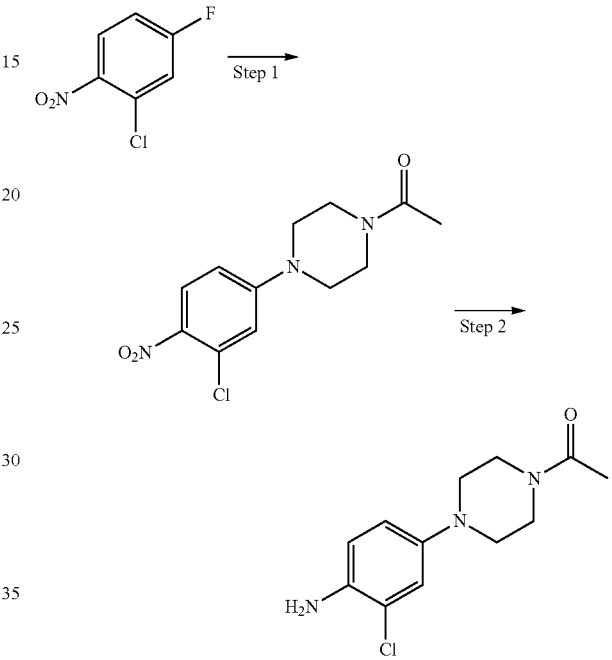

Step 1: Preparation of 1-(4-(3-chloro-4-nitrophenyl)piperazin-1-yl)ethanone 2-chloro-4-fluoronitrobenzene (350 mg), N-acetylpiperazine (0.5 ml) and potassium carbonate (500 mg) were dissolved in dimethylformamide (3 ml) and stirred at 50° C. overnight. The reaction mixture was distilled under reduced pressure to remove dimethylformamide and added with distilled water. Then, the recrystallized yellow solid was filtered and the subsequent reaction was proceeded without further purification.

$^1$H NMR (300 MHz, CDCl$_3$) δ 8.04 (d, J=9.3 Hz, 1H), 6.86 (d, J=2.0 Hz, 1H), 6.74 (dd, J=2.0, 9.3 Hz, 1H), 3.80 (m, 2H), 3.66 (m, 2H), 3.42 (m, 4H), 2.16 (s, 3H).

Step 2: Preparation of 1-(4-(4-amino-3-chlorophenyl)piperazin-1-yl)ethanone

The compound prepared in Step 1 was dissolved in ethanol (10 ml) and distilled water (1.0 ml), added with iron (powder, 2.0 g) and ammonium chloride (1.0 g), and stirred at 90° C. for 2 hours. Then, the resultant was filtered using celite and the filtrate was distilled under reduced pressure to remove the solvent. The resulting white solid was used in the subsequent reaction without further purification.

¹H NMR (300 MHz, CDCl₃) δ 6.88 (m, 1H), 6.73 (m, 2H), 3.75 (m, 1H), 3.59 (m, 1H), 2.99 (m, 4H), 2.13 (s, 3H).

Preparation Example 7

Preparation of tert-butyl 4-(4-amino-3-phenoxyphenyl)piperazin-1-carboxylate

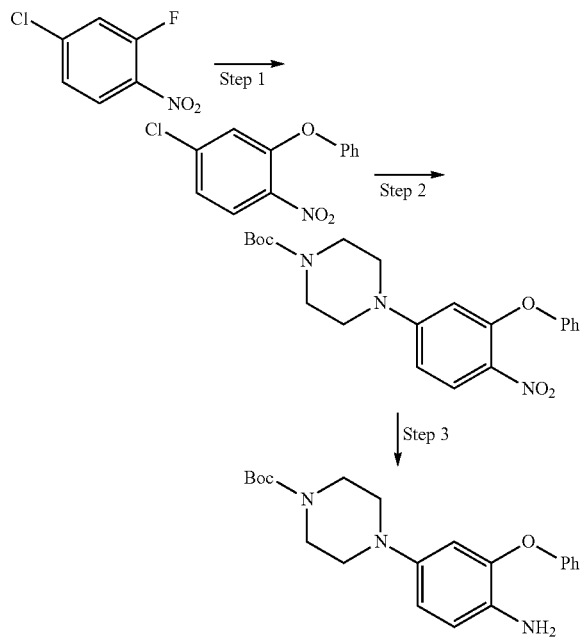

Step 1: Preparation of 4-chloro-1-nitro-2-phenoxybenzene 4-chloro-2-fluoro-nitrobenzene (500 mg), phenol (270 mg), and potassium carbonate (400 mg) were dissolved in dimethyl sulfoxide (10 ml), and stirred at room temperature for 2 hours. The mixture was added with water and ethyl ether to extract an organic layer. The resulting organic layer was washed with saturated brine, and water was removed with sodium sulfate, and the solvent was removed by distillation under reduced pressure. The yellow target compound obtained by removing the solvent was used in the subsequent reaction without further purification (500 mg).

¹H NMR (300 MHz, CDCl₃) δ 7.94 (d, J=8.8 HZ, 1H), 7.44 (m, 2H), 7.25 (m, 1H), 7.14 (dd, J=2.1, 8.8 Hz, 1H), 7.09 (m, 2H), 6.94 (d, J=2.1 Hz, 1H)

Step 2: Preparation of tert-butyl 4-(4-nitro-3-phenoxyphenyl)piperazin-1-carboxylate The compound (500 mg) prepared in Step 1, N-Boc-piperazine (500 mg) and tassium carbonate (2.0 g) were dissolved in dimethylformamide (3 ml), and stirred at 90° C. for 2 hours. The dimethylformamide of the mixed solution was removed by distillation under reduced pressure, and extracted with ethyl acetate. The extracted organic layer was washed with saturated brine, and water was removed with sodium sulfate, and the solvent was removed by distillation under reduced pressure. The solvent-removed mixture was purified by column chromatography to obtain a yellow target compound.

¹H NMR (300 MHz, CDCl₃) δ 8.08 (d, J=9.4 HZ, 1H), 7.36 (m, 2H), 7.14 (m, 1H), 7.01 (m, 2H), 6.58 (dd, J=2.7, 9.4 Hz, 1H), 6.31 (d, J=2.7 Hz, 1H), 3.54 (m, 4H), 3.28 (m, 4H), 1.46 (s, 9H).

Step 3: Preparation of tert-butyl 4-(4-amino-3-phenoxyphenyl)piperazin-1-carboxylate The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

¹H NMR (300 MHz, CDCl₃) δ 7.30 (m, 2H), 7.05 (m, 1H), 6.97 (m, 1H), 6.94 (m, 1H), 6.78 (d, J=8.6 Hz, 1H), 6.65 (dd, J=2.6, 8.6 Hz, 1H), 6.56 (d, J=2.6 Hz, 1H), 3.53 (t, J=5.1 Hz, 1H), 2.93 (d, J=5.1 Hz, 1H), 1.46 (s, 9H).

Preparation Example 8

Preparation of tert-butyl-4-(4-amino-3-(difluoromethoxy)phenyl)piperazin-1-carboxylate

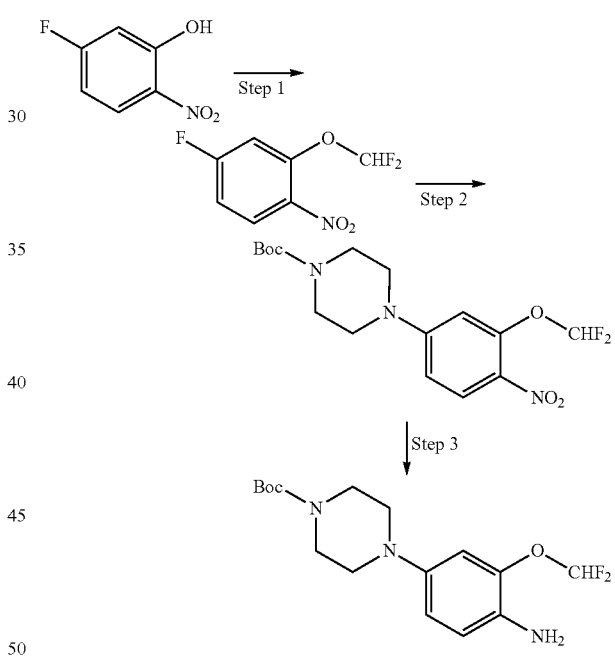

Step 1: Preparation of 2-(difluoromethoxy)-4-fluoro-1-nitrobenzene 5-fluoro-2-nitrophenol (3.1 g) was dissolved in dimethylformamide (40 mL), and potassium carbonate (4.2 g) and chlorodifluoroacetic acid methyl ester (3.2 mL) were slowly dropwisely added at room temperature. The mixed solution was isothermally maintained to 100° C., stirred for 2 hours, and then cooled to room temperature. Then, the resultant was added with water (100 ml) and extracted with diethyl ether (200 mL). The resulting organic layer was washed with saturated brine and dried with sodium sulfate and filtered. The resulting mixture was purified by column chromatography (silica gel, hexane/ethyl acetate) to obtain a target compound as a bright yellow solid.

$^1$H NMR (300 MHz, CD$_3$OD) δ 8.03 (dd, J=9.0, 5.9 Hz, 1H), 7.17-7.06 (m, 2H), 6.65 (t, J=72.3 Hz, 1H).

Step 2: Preparation of 4-(N-boc-piperazin-1-yl)-2-(difluoromethoxy)-1-nitrobenzene The compound (7.0 g) prepared in Step 1 and N-Boc-piperazine (7.0 g) were dissolved in dimethylformamide (100 mL), and added with potassium carbonate (6.0 g). The mixture was stirred at 45° C. overnight, slowly dropwisely added with water (200 mL) to recrystallize the yellow solid. The mixture was filtered to dry the solid and suspended in ethyl acetate (100 mL), added with hexane (200 mL) to recrystallize the yellow solid, and the solid was filtered to obtain a target compound (9.0 g, 71%).
$^1$H NMR (300 MHz, CD$_3$OD) δ 8.04 (d, J=9.3 Hz, 1H), 6.77 (d, J=9.3 Hz, 1H), 6.63 (s, 1H), 6.62 (t, J=74.2 Hz, 1H), 3.63-3.58 (m, 4H), 3.35-3.39 (m, 4H), 1.49 (s, 9H).

Step 3: Preparation of tert-butyl-4-(4-amino-3-(difluoromethoxy)phenyl)piperazin-1-carboxylate The compound (9.0 g) prepared in Step 2 was dissolved in ethanol/ethyl acetate (200 mL/40 mL), added with 10% Pd/C (~0.5 g), and stirred under hydrogen atmosphere overnight. Then, the mixed solution was filtered to remove Pd/C, and the filtrate was concentrated to obtain a target compound as a bright purple solid (8.0 g, 88%).
$^1$H NMR (300 MHz, CD$_3$OD) δ 6.83-6.74 (m, 3H), 6.71 (t, J=73.2 Hz, 1H), 3.71-3.63 (m, 4H), 3.05-2.96 (m, 4H), 1.49 (s, 9H).

Preparation Example 9

Preparation of tert-butyl-4-(4-amino-3-fluorophenyl)piperazin-1-carboxylate

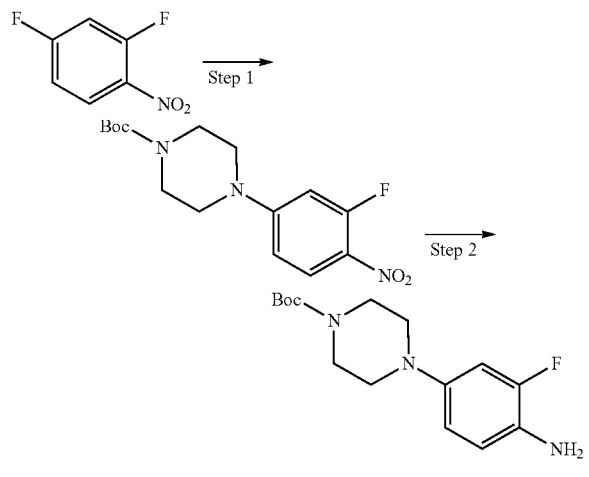

Step 1: Preparation of tert-butyl-4-(3-fluoro-4-nitrophenyl)piperazin-1-carboxylate 2,4-dinitrobenzene (1.2 g), N-Boc-piperazine (1.4 g) and potassium carbonate (1.2 g) were dissolved in dimethylformamide (5 mL) and stirred at 50° C. overnight. Then, the mixture was distilled under reduced pressure to remove dimethylformamide, added with water, and extracted with ethyl acetate. The thus obtained organic layer was washed with brine, and water was removed with sodium sulfate, and the solvent was removed by distillation under reduced pressure. The mixture was purified by column chromatography (silica gel) to obtain target compounds (R$_f$=0.3, hexane:ethyl acetate=2:1) and (tert-butyl-4-(5-fluoro-2-nitrophenyl)piperazin-1-carboxylate (R$_f$=0.6, hexane:ethyl acetate=2:1).
$^1$H NMR (300 MHz, CDCl$_3$) δ 8.04 (t, J=9.0 Hz, 1H), 6.58 (dd, J=3.0, 9.4 Hz, 1H), 6.52 (dd, J=2.7, 14.7 Hz, 1H), 3.60 (m, 4H), 3.41 (m, 4H), 1.49 (s, 9H).

Step 2: Preparation of tert-butyl-4-(4-amino-3-fluorophenyl)piperazin-1-carboxylate The compound prepared in Step 1 was dissolved in ethanol (10 ml) and water (1.0 ml), added with iron (powder, 2.0 g) and ammonium chloride (1.0 g), and stirred at 80° C. for 2 hours. Then, the resultant was filtered with celite, distilled under reduced pressure to remove the solvent. The thus obtained target compound as a white solid was used in the subsequent reaction without further purification.
Mass (M+H$^+$) calcd for C$_{15}$H$_{22}$FN$_3$O$_2$ 295.17. found 296.09.

Preparation Example 10

Preparation of 1-(4-(4-amino-3-(phenylamino)phenyl)piperazin-1-yl)ethanone

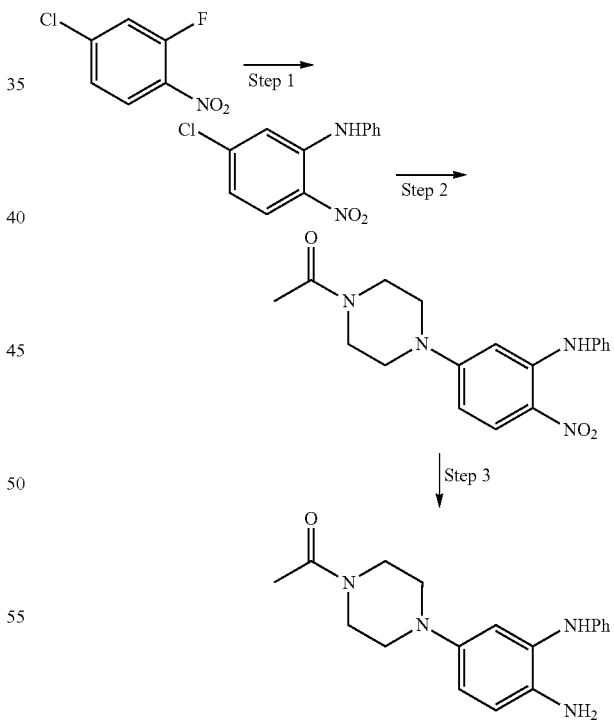

Step 1: Preparation of 5-chloro-2-nitro-N-phenylaniline 4-chloro-2-fluoronitrobenzene (250 mg), aniline (0.40 mL) and potassium carbonate (500 mg) were dissolved in dimethyl sulfoxide (1.5 mL) and stirred at 50° C. overnight.

The mixture was added with water, extracted with ethyl acetate, and the organic layer was washed with saturated brine, and the water was removed with sodium sulfate. The reaction solution was removed of the solvent by distillation under reduced pressure, and the subsequent reaction was proceeded without further purification of the thus obtained compound.

$^1$H NMR (300 MHz, CDCl$_3$) δ 9.54 (br, 1H), 8.16 (d, J=9.1 Hz, 1H), 7.1-7.5 (m, 5H), 6.71 (m, 2H).

Step 2: Preparation of 1-(4-(4-nitro-3-(phenylamino) phenyl)piperazin-1-yl)ethanone The compound (300 mg) prepared in Step 1 and N-acetylpiperazine (300 mg) were dissolved in dimethyl sulfoxide (3 mL), and stirred at 90° C. for 3 hours. The mixture was added with water, and extracted with ethyl acetate. The thus obtained organic layer was washed with saturated brine, the water was removed with sodium sulfate, and the solvent was removed by distillation under reduced pressure. Then, the compound was added with ethyl ether to form a solid, and the solid was filtered to obtain a target compound as a yellow solid.

$^1$H NMR (300 MHz, CDCl$_3$) δ 9.83 (br, 1H), 8.15 (d, J=9.6 Hz, 1H), 7.3-7.5 (m, 5H), 6.37 (d, J=2.6 Hz, 1H), 6.30 (dd, J=2.6, 9.6 Hz, 1H), 3.71 (m, 2H), 3.58 (m, 2H), 3.31 (m, 4H), 2.11 (s, 3H).

Step 3: Preparation of 1-(4-(4-amino-3-(phenylamino)phenyl)piperazin-1-yl)ethanone The compound prepared in Step 2 was dissolved in ethanol, added with 10% Pd/C and stirred under hydrogen atmosphere for 2 hours. Upon completion of the reaction, the Pd/C in the reaction mixture was removed using celite and the solvent was removed under reduced pressure. The thus obtained compound was used in the subsequent reaction without further purification.

Preparation Example 11

Preparation of 1-(4-(4-amino-3-(tert-butylamino) phenyl)piperazin-1-yl)ethanone

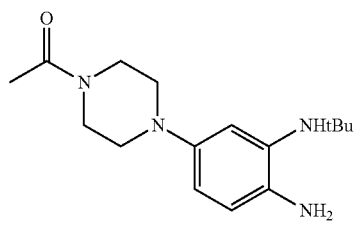

Step 1: Preparation of N-(tert-butyl)-5-chloro-2-nitroaniline 4-chloro-2-fluoronitrobenzene (250 mg) and t-butylamine (0.40 mL) were dissolved in dimethyl sulfoxide (3.0 mL) and stirred at room temperature overnight. Then, the mixture was added with water and extracted with ethyl acetate. The thus obtained organic layer was washed with saturated brine, and the water was removed with sodium sulfate, and the solvent was removed by distillation under reduced pressure. The subsequent reaction was proceeded without further purification of the thus obtained compound.

$^1$H NMR (300 MHz, CDCl$_3$) δ 8.42 (br, 1H), 8.13 (d, J=9.2 Hz, 1H), 7.07 (d, J=2.1 hz, 1H), 6.56 (dd, J=2.1, 9.2 Hz, 1H), 1.51 (s, 9H).

Step 2: Preparation of 1-(4-(3-(tert-butylamino)-4-nitrophenyl)piperazin-1-yl)ethanone A target compound was obtained in the same manner as in Step 2 of Preparation Example 10 except that N-(tert-butyl)-5-chloro-2-nitroaniline (300 mg) was used instead of 5-chloro-2-nitro-N-phenylaniline.

$^1$H NMR (300 MHz, CDCl$_3$) δ 8.71 (br, 1H), 8.11 (d, J=9.5 Hz, 1H), 6.18 (m, 2H), 3.80 (m, 2H), 3.66 (m, 2H), 3.42 (m, 4H), 2.15 (s, 3H), 1.51 (s, 9H).

Step 3: Preparation of 1-(4-(4-amino-3-(tert-butylamino)phenyl)piperazin-1-yl)ethanone A target compound was obtained in the same manner as in Step 3 of Preparation Example 10 except that 1-(4-(3-(tert-butylamino)-4-nitrophenyl)piperazin-1-yl)ethanone was used instead of 1-(4-(4-nitro-3-(phenylamino)phenyl)piperazin-1-yl)ethanone.

Preparation Example 12

Preparation of tert-butyl-4-(4-amino-3-(N-methylpropionamido)phenyl)piperazin-1-carboxylate

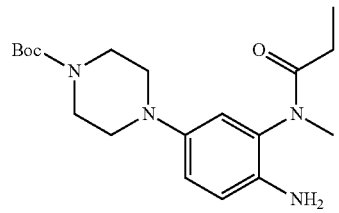 [SMILES: CCC(=O)N(C)c1cc(N2CCN(C(=O)OC(C)(C)C)CC2)ccc1N]

Step 1: Preparation of 5-chloro-N-methyl-2-nitroaniline

A target compound was obtained in the same manner as in Step 1 of Preparation Example 11 except that methylamine (2.0 mL in THF) was used instead of t-butylamine.

$^1$H NMR (300 MHz, CDCl$_3$) δ 8.12 (d, J=9.2 Hz, 1H), 6.83 (d, J=2.1 Hz, 1H), 6.62 (dd, J=2.1, 9.2 Hz, 1H), 3.02 (d, J=5.1 Hz, 3H).

Step 2: Preparation of N-(5-chloro-2-nitrophenyl)-N-methylpropionamide 5-chloro-N-methyl-2-nitroaniline (500 mg) was dissolved in methylene chloride anhydrous (9 mL), added with triethylamine (3 mL) and propionyl chloride (1 mL) and refluxed. Then, saturated sodium bicarbonate was added thereto and extracted with ethyl acetate. The extracted organic layer was washed with saturated sodium bicarbonate, dried with sodium sulfate, filtered and concentrated under reduced pressure. The concentrated filtrate was purified by column chromatography (silica gel, hexane/ethyl acetate) to obtain a target compound as a yellow solid.

¹H NMR (300 MHz, CDCl₃) δ 8.14 (d, J=9.3 Hz, 1H), 6.83 (d, J=9.3 Hz, 1H), 6.61 (s, 1H), 3.69-3.54 (m, 4H), 3.49-3.37 (m, 4H), 3.20 (s, 3H), 2.13-1.92 (m, 2H), 1.49 (s, 9H), 1.05 (t, J=7.2 Hz, 3H).

Step 3: Preparation of 4-(3-(N-methylpropiona-mido)-4-nitrophenyl)piperazin-1-carboxylate The compound (460 mg) prepared in Step 2 was dissolved in dimethylformamide (7 ml), added with N-Boc-piperazine (460 mg) and potassium carbonate (340 mg), and stirred at 90° C. overnight. Then, the mixture was distilled under reduced pressure to remove the solvent, added with water, and extracted with ethyl acetate. The extracted organic layer was washed with saturated brine, dried with sodium sulfate, and filtered. The filtrate was concentrated under reduced pressure and purified by column chromatography (silica gel, hexane/ethyl acetate) to obtain a target compound as a yellow solid (272.3 mg).
¹H NMR (300 MHz, CDCl₃) δ 8.14 (d, J=9.3 Hz, 1H), 6.83 (d, J=9.3 Hz, 1H), 6.61 (s, 1H), 3.69-3.54 (m, 4H), 3.49-3.37 (m, 4H), 3.20 (s, 3H), 2.13-1.92 (m, 2H), 1.49 (s, 9H), 1.05 (t, J=7.2 Hz, 3H).

Step 4: Preparation of tert-butyl-4-(4-amino-3-(N-methylpropionamido)phenyl)piperazin-1-carboxylate The compound (272.3 mg, 0.69 mmol) prepared in Step 3 was dissolved in a mixed solution (2 mL) of ethyl acetate and ethanol, added with 10% Pd/C (70 mg), and stirred at room temperature under hydrogen atmosphere overnight. Then, the Pd/C was removed from the mixture with celite, concentrated under reduced pressure to obtain a target compound as a yellow solid (231.2 mg).
¹H NMR (300 MHz, CDCl₃) δ 6.84-6.80 (m, 1H), 6.79-6.72 (m, 1H), 6.66 (br, 1H), 3.67-3.46 (m, 6H), 3.18 (s, 3H), 3.01-2.92 (m, 4H), 2.20-1.99 (m, 2H), 1.48 (s, 9H), 1.05 (t, J=7.5 Hz, 3H).

Preparation Example 13

Preparation of tert-butyl 4-(4-amino-3-(N-methylbu-tylamido)phenyl)piperazin-1-carboxylate

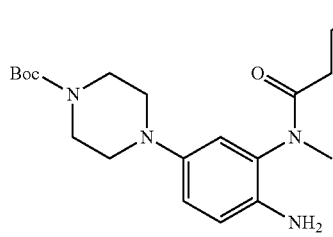

Step 1: Preparation of N-(5-chloro-2-nitrophenyl)-N-methylbutylamide

A target compound as a yellow solid was obtained in the same manner as in Step 2 of Preparation Example 12 except that butylchloride (1 ml) was used instead of propionyl chloride.
¹H NMR (300 MHz, CDCl₃) δ 8.01 (d, J=8.7 Hz, 1H), 7.55 (d, J=8.7 Hz, 1H), 7.38 (s, 1H), 3.21 (s, 3H), 1.96 (q, J=7.2 Hz, 2H), 1.65-1.52 (m, 2H), 0.84 (t, J=7.2 Hz, 3H).

Step 2: Preparation of tert-butyl-4-(3-(N-methylbuty-lamido)-4-nitrophenyl)piperazin-1-carboxylate A target compound (240 mg) was obtained in the same manner as in Step 3 of Preparation Example 12 except that N-(5-chloro-2-nitrophenyl)-N-methylbutylamide prepared in Step 1 was used instead of N-(5-chloro-2-nitrophenyl)-N-methylpropionamide.
¹H NMR (300 MHz, CDCl₃) δ 8.15 (d, J=9.3 Hz, 1H), 6.81 (d, J=9.0 Hz, 1H), 6.62-6.56 (m, 1H), 3.68-3.54 (m, 4H), 3.50-3.34 (m, 4H), 3.20 (s, 3H), 1.95 (q, J=7.8 Hz, 2H), 1.65-1.54 (m, 4H), 1.50 (s, 9H), 1.26 (t, J=6.9 Hz, 2H), 1.01 (t, J=7.5 Hz, 2H), 0.83 (t, J=7.5 Hz, 3H).

Step 3: Preparation of tert-butyl-4-(4-amino-3-(N-methylbutylamido)phenyl)piperazin-1-carboxylate A target compound (220 mg) was obtained in the same manner as in Step 4 of Preparation Example 12 except that the compound prepared in Step 2 was used instead of 4-(3-(N-methylpropionamido)-4-nitrophenyl)piperazin-1-carboxy-late.
¹H NMR (300 MHz, CDCl₃) δ 6.84 (d, J=8.7 Hz, 1H), 6.75 (d, J=9.0 Hz, 1H), 6.61 (s, 1H), 3.66-3.39 (m, 6H), 3.18 (s, 3H), 3.03-2.92 (m, 4H), 2.15-1.96 (m, 2H), 1.69-1.53 (m, 4H), 1.48 (s, 9H), 1.25 (t, J=6.6 Hz, 2H), 1.10-1.01 (m, 2H), 0.84 (t, J=7.2 Hz, 3H).

Preparation Example 14

Preparation of 1-(4-(4-(2,5-dichloropyrimidin-4-ylamino)-3-methoxyphenyl)piperazin-1-yl)ethanone

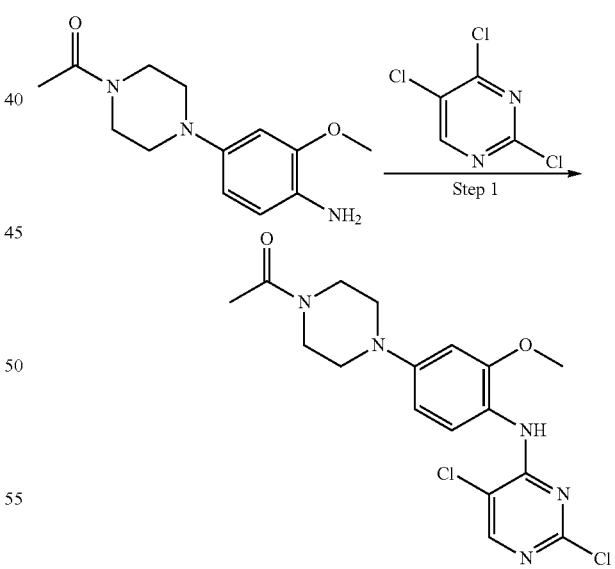

1-(4-(4-amino-3-methoxyphenyl)piperazin-1-yl)ethanone (150 mg) prepared in Preparation Example 1, 2,4,5-trichloropyrimidine (120 mg) and potassium carbonate (120 mg) were dissolved in dimethylformamide (2 ml), and stirred at 80° C. overnight. The dimethylformamide of the mixture was removed under reduced pressure and added with water to form a solid. The solid was filtered to obtain a target compound.

¹H-NMR (300 MHz, CDCl₃) δ 8.32 (d, J=8.8 Hz, 1H), 8.14 (s, 1H), 7.89 (s, 1H), 6.58 (dd, J=2.5, 8.8 Hz, 1H), 6.54 (d, J=2.5 Hz, 1H), 3.93 (s, 3H), 3.78 (m, 2H), 3.64 (m, 2H), 3.16 (m, 4H), 2.15 (s, 3H);

Mass (M+H⁺) calcd for $C_{17}H_{19}Cl_2N_5O_2$ 395.09. found 396.1.

Preparation Example 15

Preparation of 1-(4-(4-(2,5-dichloropyrimidin-4-ylamino)-3-ethoxyphenyl)piperazin-1-yl)ethanone

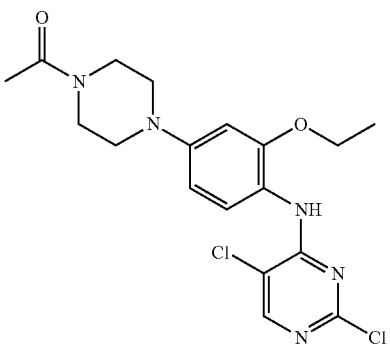 [SMILES: CCOc1cc(N2CCN(C(C)=O)CC2)ccc1Nc1nc(Cl)ncc1Cl]

A target compound was obtained in the same manner as in Preparation Example 14 except that the compound prepared in Preparation Example 2 was used as a starting material instead of 1-(4-(4-amino-3-methoxyphenyl)piperazin-1-yl)ethanone.

¹H-NMR (300 MHz, CDCl₃) δ 8.37 (d, J=8.6 Hz, 1H), 8.16 (s, 1H), 8.04 (s, 1H), 6.61-6.59 (m, 1H), 6.56 (s, 1H), 4.15 (t, J=7.0 Hz, 2H), 3.81 (t, J=4.9 Hz, 2H), 3.66 (t, J=4.9 Hz, 2H), 3.21-3.14 (m, 4H), 2.17 (s, 3H), 1.51 (t, J=7.0 Hz, 3H).

Preparation Example 16

Preparation of 1-(4-(4-(2,5-dichloropyrimidin-4-ylamino)-3-propoxyphenyl)piperazin-1-yl)ethanone

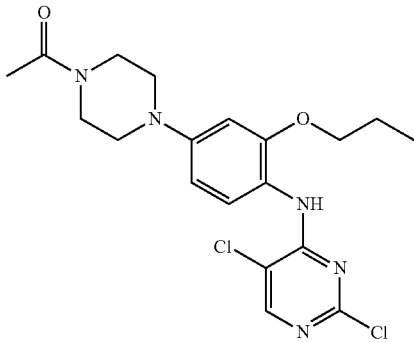 [SMILES: CCCOc1cc(N2CCN(C(C)=O)CC2)ccc1Nc1nc(Cl)ncc1Cl]

A target compound was obtained in the same manner as in Preparation Example 14 except that the compound prepared in Preparation Example 3 was used as a starting material instead of 1-(4-(4-amino-3-methoxyphenyl)piperazin-1-yl)ethanone.

¹H-NMR (300 MHz, CDCl₃) δ 8.37 (d, J=9.1 Hz, 1H), 8.15 (s, 1H), 8.06 (s, 1H), 6.60-6.58 (m, 1H), 6.55 (s, 1H), 4.04 (t, J=6.3 Hz, 2H), 3.80 (t, J=4.9 Hz, 2H), 3.65 (t, J=4.9 Hz, 2H), 3.18 (t, J=5.2 Hz, 2H), 3.15 (t, J=5.2 Hz, 2H), 2.17 (s, 3H), 1.91 (sextet, J=14.3, 7.1 Hz, 2H), 1.11 (t, J=7.4 Hz, 3H).

Preparation Example 17

Preparation of 1-(4-(4-(2,5-dichloropyrimidin-4-ylamino)-3-isopropoxyphenyl)piperazin-1-yl)ethanone

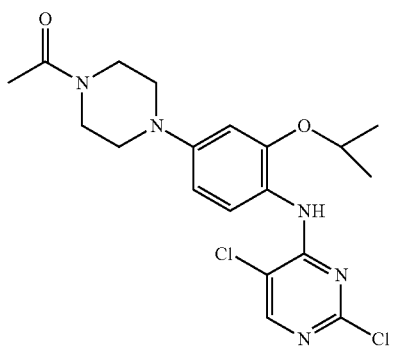 [SMILES: CC(=O)N1CCN(c2ccc(Nc3nc(Cl)ncc3Cl)c(OC(C)C)c2)CC1]

A target compound was obtained in the same manner as in Preparation Example 14 except that the compound prepared in Preparation Example 4 was used as a starting material instead of 1-(4-(4-amino-3-methoxyphenyl)piperazin-1-yl)ethanone.

¹H-NMR (300 MHz, CDCl₃) δ 8.38 (d, J=8.4 Hz, 1H), 8.13 (s, 1H), 8.08 (s, 1H), 6.61-6.54 (m, 2H), 4.64-4.55 (m, 1H), 3.80-3.77 (m, 2H), 3.65-3.62 (m, 2H), 3.17-3.08 (m, 4H), 2.15 (s, 3H), 1.41 (s, 3H), 1.39 (s, 3H).

Preparation Example 18

Preparation of 1-(4-(3-(benzyloxy)-4-(2,5-dichloropyrimidin-4-ylamino)phenyl)piperazin-1-yl)ethanone

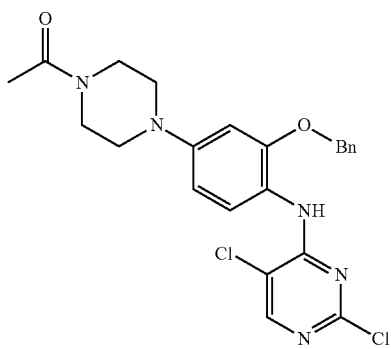 [SMILES: CC(=O)N1CCN(c2ccc(Nc3nc(Cl)ncc3Cl)c(OCc3ccccc3)c2)CC1]

A target compound was obtained in the same manner as in Preparation Example 14 except that the compound prepared in Preparation Example 5 was used as a starting material instead of 1-(4-(4-amino-3-methoxyphenyl)piperazin-1-yl)ethanone.

Mass (M+H⁺) calcd for $C_{23}H_{23}Cl_2N_5O_2$ 471.12. found 471.77.

Preparation Example 19

Preparation of 1-(4-(3-chloro-4-(92,5-dichloropyrimidin-4-yl)amino)phenyl)piperazin-1-yl)ethanone

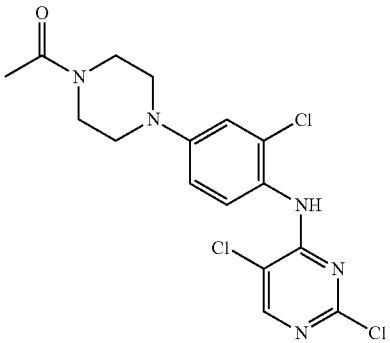 [SMILES: CC(=O)N1CCN(c2ccc(Nc3nc(Cl)ncc3Cl)c(Cl)c2)CC1]

A target compound was obtained in the same manner as in Preparation Example 14 except that the compound prepared in Preparation Example 6 was used as a starting material instead of 1-(4-(4-amino-3-methoxyphenyl)piperazin-1-yl)ethanone.
¹H-NMR (300 MHz, CDCl₃) δ 8.20 (d, J=9.0 Hz, 1H), 8.18 (s, 1H), 6.89 (dd, J=2.8, 9.1 Hz, 1H), 6.76 (dd, J=2.8, 9.1 Hz, 1H), 3.75 (m, 2H), 3.61 (m, 2H), 3.41 (m, 4H), 2.12 (s, 3H).

Preparation Example 20

Preparation of 1-(4-(4-(2,5-dichloropyrimidin-4-ylamino)-3-phenoxyphenyl)piperazin-1-yl)ethanone

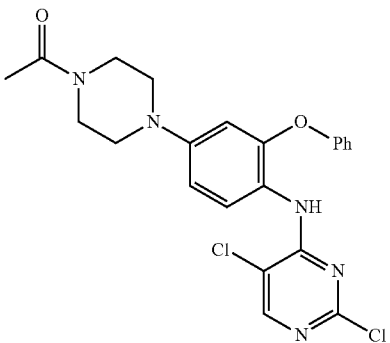 [SMILES: CC(=O)N1CCN(c2ccc(Nc3nc(Cl)ncc3Cl)c(Oc3ccccc3)c2)CC1]

The solid compound, which was obtained in the same manner as in Preparation Example 14 except that the compound prepared in Preparation Example 7 was used as a starting material instead of 1-(4-(4-amino-3-methoxyphenyl)piperazin-1-yl)ethanone, was dissolved in methylenechloride (4 ml), added with trifluoroacetic acid (2 ml) and stirred at room temperature for 10 minutes. The mixture was concentrated under reduced pressure, added with acetic anhydride ((0.01 ml), triethylamine (0.2 ml) and methylenechloride (2 ml), and stirred for 2 hours. Then, saturated aqueous solution of sodium bicarbonate was added thereto, extracted with ethyl acetate, and the extracted organic layer was washed with saturated sodium bicarbonate. The washed organic layer was dried with sodium sulfate, filtered, and concentrated under reduced pressure. The mixture was separated by column chromatography (silica gel, hexane/ethyl acetate) to obtain a target compound.
¹H-NMR (300 MHz, CDCl₃) δ 8.32 (d, J=9.0 Hz, 1H), 8.12 (s, 1H), 5.6-7.4 (m, 7H), 3.73 (m, 2H), 3.59 (m, 2H), 3.15 (m, 4H), 2.12 (s, 3H).

Preparation Example 21

Preparation of tert-butyl-4-(4-((2,5-dichloropyrimidin-4-yl)amino)-3-(difluoromethoxy)phenyl)piperazin-1-carboxylate

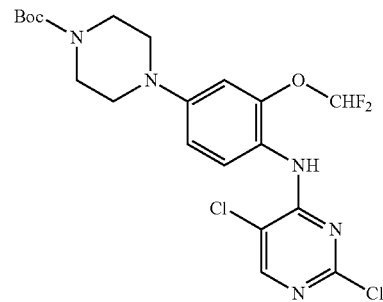 [SMILES: CC(C)(C)OC(=O)N1CCN(c2ccc(Nc3nc(Cl)ncc3Cl)c(OC(F)F)c2)CC1]

A target compound was obtained in the same manner as in Preparation Example 14 except that the compound prepared in Preparation Example 8 was used as a starting material instead of 1-(4-(4-amino-3-methoxyphenyl)piperazin-1-yl)ethanone.
¹H-NMR (300 MHz, DMSO-d₆) δ 8.82 (d, J=14 Hz, 1H), 8.24 (s, 1H), 6.7-7.2 (m, 3H), 3.40 (m, 4H), 3.19 (m, 2H), 3.11 (m, 2H), 1.37 (s, 9H);
Mass (M+H⁺) calcd for $C_{20}H_{23}C_{12}F_2N_5O_3$ 489.11. found 489.65.

Preparation Example 22

Preparation of 4-(4-((2,5-dichloropyrimidin-4-yl)amino)-3-fluorophenyl)piperazin-1-carboxylate

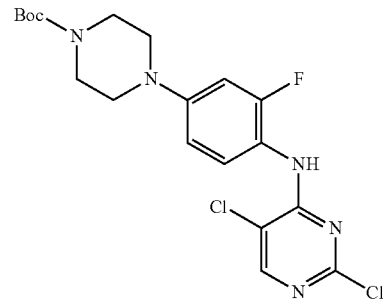 [SMILES: CC(C)(C)OC(=O)N1CCN(c2ccc(Nc3nc(Cl)ncc3Cl)c(F)c2)CC1]

A target compound was obtained in the same manner as in Preparation Example 14 except that the compound prepared in Preparation Example 9 was used as a starting material instead of 1-(4-(4-amino-3-methoxyphenyl)piperazin-1-yl)ethanone.
¹H-NMR (300 MHz, DMSO-d₆) δ 8.15 (s, 1H), 6.65-6.8 (m, 3H), 3.58 (m, 4H), 3.15 (m, 4H), 1.55 (s, 9H);

Mass (M+H$^+$) calcd for $C_{19}H_{22}Cl_2FN_5O_2$ 441.11. found 441.94.

Preparation Example 23

Preparation of 1-(4-(4-(2,5-dichloropyrimidin-4-ylamino)-3-(phenylamino)phenyl)piperazin-1-yl)ethanone

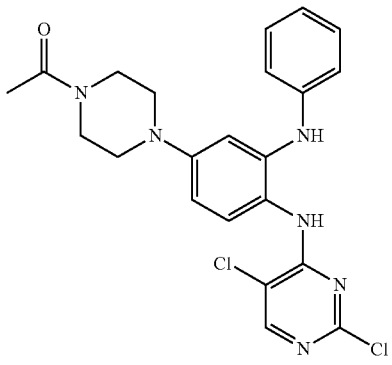 [SMILES: CC(=O)N1CCN(c2ccc(Nc3nc(Cl)ncc3Cl)c(Nc3ccccc3)c2)CC1]

The compound (114.5 mg) prepared in Preparation Example 10, 2,4,5-trichloropyrimidine (40 µl) and potassium carbonate (80 mg) were dissolved in dimethylformamide (1.5 ml), and stirred at 80° C. overnight. Then, the mixture was cooled at room temperature, distilled at room temperature to remove the solvent, added with water, and extracted with ethyl acetate. The extracted organic layer was washed with saturated brine, dried with sodium sulfate, and concentrated under reduced pressure. The mixture was separated by column chromatography (silica gel, ethyl acetate/hexane/methanol=4/4/1) to obtain a target compound as a brown solid (115 mg).

$^1$H-NMR (300 MHz, CDCl$_3$) δ 8.24 (s, 1H), 7.67 (d, J=8.7 Hz, 1H), 7.37-7.08 (m, 5H), 6.92 (d, J=8.7 Hz, 1H), 6.84 (br, 2H), 6.59 (s, 1H), 3.80-3.68 (m, 2H), 3.67-1.54 (m, 2H), 3.20-3.05 (m, 4H), 2.12 (s, 3H).

Preparation Example 24

Preparation of 1-(4-(3-(tert-butylamino)-4-(2,5-dichloropyrimidin-4-yl)amino)phenyl)piperazin-1-yl)ethanone

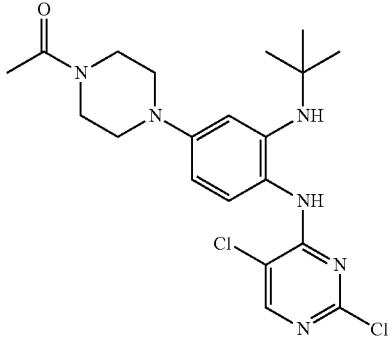 [SMILES: CC(=O)N1CCN(c2ccc(Nc3nc(Cl)ncc3Cl)c(NC(C)(C)C)c2)CC1]

A target compound (115 mg) as a brown solid was obtained in the same manner as in Preparation Example 23 except that the compound (110 mg) prepared in Preparation Example 11 was used as a starting material instead of the compound prepared in Preparation Example 10.

$^1$H-NMR (300 MHz, CD$_3$OH) δ 8.17 (s, 1H), 7.53 (d, J=8.8 Hz, 1H), 6.73 (s, 1H), 6.45 (dd, J=1.9, 9.0 Hz, 1H), 3.80-3.61 (m, 5H), 3.30-3.11 (m, 5H), 2.15 (s, 3H), 1.28 (s, 9H).

Preparation Example 25

Preparation of N-(5-(4-acetylpiperazin-1-yl)-2-(2,5-dichloropyrimidin-4-ylamino)phenyl)-N-methylpropionamide

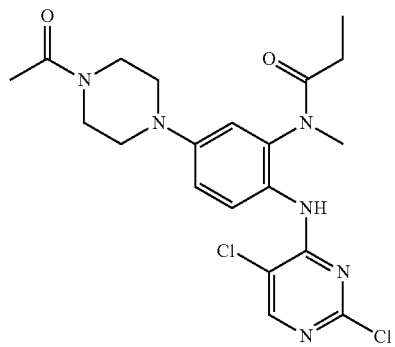 [SMILES: CCC(=O)N(C)c1cc(N2CCN(C(C)=O)CC2)ccc1Nc1nc(Cl)ncc1Cl]

A target compound (115 mg) as a brown solid was obtained in the same manner as in Preparation Example 23 except that the compound (231 mg) prepared in Preparation Example 12 was used as a starting material instead of the compound prepared in Preparation Example 10.

$^1$H-NMR (300 MHz, CDCl$_3$) δ 8.31 (d, J=9.0 Hz, 1H), 8.19 (s, 1H), 7.04-6.96 (m, 1H), 6.73 (s, 1H), 3.67-3.53 (m, 4H), 3.37 (s, 1H), 3.22 (s, 3H), 3.19-3.08 (m, 4H), 2.19-1.96 (m, 2H), 1.50 (s, 9H), 1.26 (t, J=7.2 Hz, 3H).

Preparation Example 26

Preparation of tert-butyl-4-(4-(2,5-dichloropyrimidin-4-yl)amino)-3-(N-methylbutylamido)phenyl)piperazin-1-carboxylate

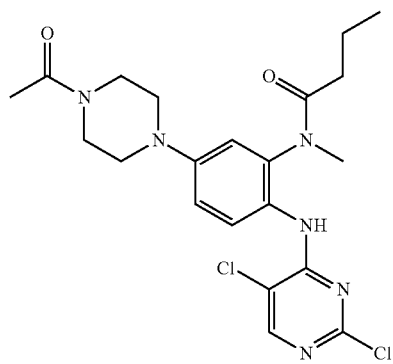 [SMILES: CCCC(=O)N(C)c1cc(N2CCN(C(C)=O)CC2)ccc1Nc1nc(Cl)ncc1Cl]

A target compound (87 mg) as a brown solid was obtained in the same manner as in Preparation Example 14 except that the compound (231 mg) prepared in Preparation Example 13 was used as a starting material instead of the compound prepared in Preparation Example 1.

¹H-NMR (300 MHz, CDCl₃) δ 8.29 (d, J=9.0 Hz, 1H), 8.19 (s, 1H), 7.01 (d, J=9.0 Hz, 1H), 6.72 (s, 1H), 3.61 (s, 4H), 3.48-3.35 (m, 1H), 3.22 (s, 3H), 3.16 (s, 4H), 2.14-1.93 (m, 2H), 1.65-1.50 (m, 2H), 1.49 (s, 9H), 0.82 (t, J=7.2 Hz, 3H);

Mass (M+H¹) calced for $C_{24}H_{32}Cl_2N_6O_3$ 522.19. found 522.85.

Preparation Example 27

Preparation of tert-butyl-4-(4-((2-chloro-5-fluoropyrimidin-4-yl)amino)-3-methoxyphenyl)piperazin-1-carboxylate

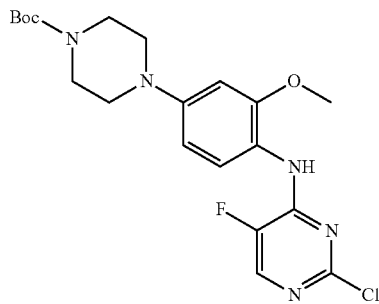 [SMILES: COc1cc(N2CCN(C(=O)OC(C)(C)C)CC2)ccc1Nc1nc(Cl)ncc1F]

A target compound (900 mg) as a grey solid was obtained in the same manner as in Preparation Example 14 except that 2,4-dichloro-5-fluoropyrimidine was used as a starting material instead of 2,4,5-trichloropyrimidine.

¹H-NMR (300 MHz, CDCl₃) δ 8.31 (d, J=8.7 Hz, 1H), 8.00 (s, 1H), 7.51 (s, 1H), 6.58 (d, J=8.7 Hz, 1H), 6.54 (s, 1H), 3.91 (s, 3H), 3.60 (t, J=4.8 Hz, 4H), 3.12 (t, J=4.8 Hz, 4H), 1.49 (s, 9H).

Preparation Example 28

Preparation of tert-butyl-4-(4-((2-chloro-5-fluoropyrimidin-4-yl)amino)-3-(difluoromethoxy)phenyl)piperazin-1-carboxylate

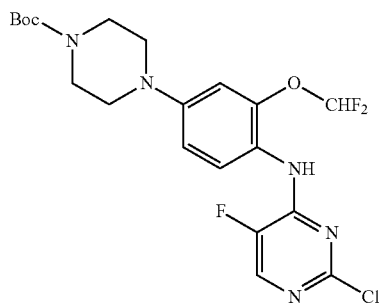 [SMILES: CC(C)(C)OC(=O)N1CCN(c2ccc(Nc3nc(Cl)ncc3F)c(OC(F)F)c2)CC1]

A target compound (850 mg) as a grey solid was obtained in the same manner as in Preparation Example 14 except that 2,4-dichloro-5-fluoropyrimidine was used as a starting material instead of 2,4,5-trichloropyrimidine, and the compound prepared in Preparation Example 8 was used instead of the compound prepared in Preparation Example 1.

¹H-NMR (300 MHz, CDCl₃) δ 8.19 (d, J=5.4 Hz, 1H), 8.07 (s, 1H), 7.20 (s, 1H), 6.86 (d, J=5.4 Hz, 1H), 6.76 (s, 1H), 6.56 (t, J=7.45 hz, 1H), 3.63-3.59 (m, 4H), 3.20-3.15 (m, 4H), 1.51 (s, 6H).

Preparation Example 29

Preparation of tert-butyl-4-(4-(2-chloro-5-(trifluoromethyl)pyrimidin-4-yl-amino)-3-methoxyphenyl)piperazin-1-carboxylate

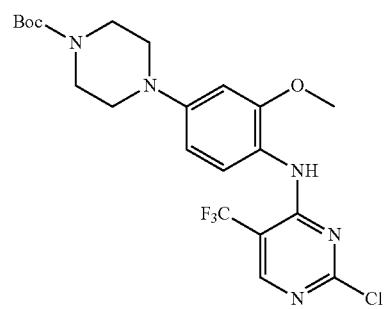 [SMILES: COc1cc(N2CCN(C(=O)OC(C)(C)C)CC2)ccc1Nc1nc(Cl)ncc1C(F)(F)F]

2,4-dichloro-5-(trifluoromethyl)pyrimidine (800 mg) and potassium carbonate (510 mg) were dissolved in n-butanol (15 ml), dropwisely added with a reaction solution, in which 4-(4-amino-3-methoxyphenyl)piperazin-1-carboxylate (1.13 g) was dissolved in n-butanol (5 ml), and stirred at room temperature overnight. Then, the mixture was distilled under reduced pressure to remove the solvent, added with ethyl acetate, and washed with saturated brine. The washed organic layer was dried with sodium sulfate, and concentrated under reduced pressure. The concentrated mixture was purified by column chromatography to obtain a target compound (430 mg).

¹H-NMR (300 MHz, CDCl₃) δ 8.35 (s, 1H), 8.22 (d, J=8.8 Hz, 1H), 7.79 (s, 1H), 6.57 (d, J=8.8 Hz, 1H), 6.53 (s, 1H), 3.90 (s, 3H), 3.59 (s, 4H), 3.13 (s, 4H), 1.49 (s, 9H).

Preparation Example 30

Preparation of tert-butyl-4-(4-((4-chloro-5-(trifluoromethyl)pyrimidin-2-yl)amino)-3-methoxyphenyl)piperazin-1-carboxylate

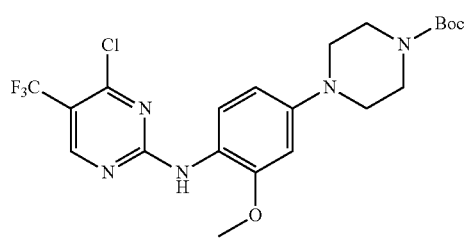 [SMILES: COc1cc(N2CCN(C(=O)OC(C)(C)C)CC2)ccc1Nc1ncc(C(F)(F)F)c(Cl)n1]

A target compound (286 mg) was obtained as a side reaction product in the same manner as in Preparation Example 29.

¹H-NMR (300 MHz, CDCl₃) δ 8.52 (s, 1H), 8.16 (d, J=8.4 Hz, 1H), 7.85 (s, 1H), 6.54 (d, J=8.4 Hz, 1H), 6.53 (s, 1H), 3.88 (s, 3H), 3.59 (s, 4H), 3.11 (s, 4H), 1.48 (s, 9H).

Preparation Example 31

Preparation of 1-(4-(4-((2-chloropyrimidin-4-yl)amino)-3-methoxyphenyl)piperazin-1-yl)ethanone

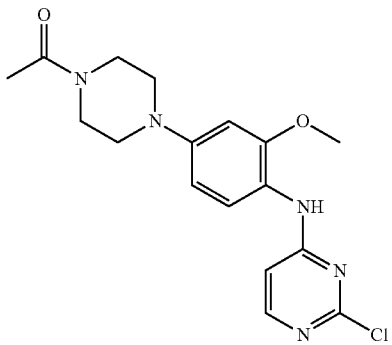 [SMILES: COc1cc(N2CCN(C(C)=O)CC2)ccc1Nc1ccnc(Cl)n1]

A target compound as a brown solid was obtained in the same manner as in Preparation Example 14 except that 2,4-dichloropyrimidine was used as a starting material instead of 2,4,5-trichloropyrimidine.

¹H-NMR (300 MHz, DMSO-d₆) δ 9.21 (s, 1H), 8.00 (d, J=6.0 Hz, 1H), 7.33 (m, 1H), 6.68 (d, J=2.4 Hz, 1H), 6.53 (dd, J=2.4, 8.6 Hz, 1H), 3.79 (s, 3H), 3.58 (s, 4H), 3.20 (s, 2H), 3.12 (m, 2H), 2.05 (s, 3H);

Mass (M+H⁺) calcd for $C_{17}H_{20}ClN_5O_2$ 361.13. found 361.90.

Preparation Example 32

Preparation of 1-(4-(4-((2,5-dichloropyrimidin-4-yl)amino)phenyl)piperazin-1-yl)ethanone

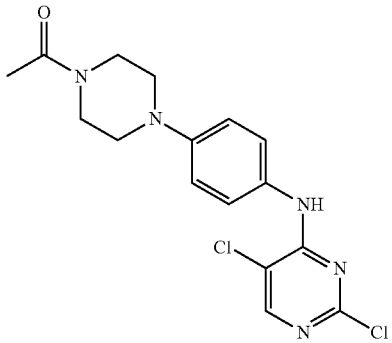 [SMILES: CC(=O)N1CCN(c2ccc(Nc3nc(Cl)ncc3Cl)cc2)CC1]

A target compound was obtained in the same manner as in Preparation Example 14 except that 1-(4-(4-aminophenyl)piperazin-1-yl)ethanone was used as a starting material instead of the compound prepared in Preparation Example 1.

Mass (M+H⁺) calcd for $C_{16}H_{17}Cl_2N_5O$ 365.08. found 366.1

Preparation Example 33

Preparation of 1-(4-(4-((2-chloro-5-fluoropyrimidin-4-yl)amino)-3-methoxyphenyl)piperazin-1-yl)ethanone

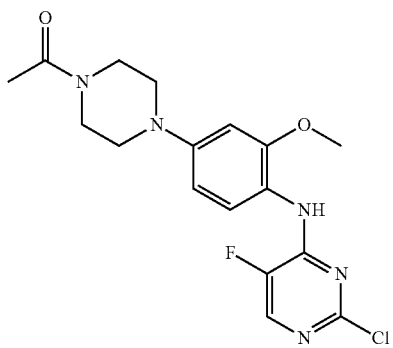 [SMILES: COc1cc(N2CCN(C(C)=O)CC2)ccc1Nc1nc(Cl)ncc1F]

A target compound was obtained in the same manner as in Preparation Example 14 except that 2,4,5,-trifluoropyrimidine was used as a starting material instead of the compound prepared in Preparation Example 1.

¹H-NMR (300 MHz, CDCl₃) δ 8.34 (d, J=8.7 Hz, 1H), 8.02 (d, J=2.8 Hz, 1H), 7.54 (s, 1H), 6.62-6.59 (m, 1H), 6.56 (s, 1H), 3.94 (s, 3H), 3.82-3.80 (m, 2H), 3.67-3.65 (m, 2H), 3.20-3.15 (m, 4H), 2.17 (s, 3H).

Preparation Example 34

Preparation of tert-butyl-4-(4-amino-3-methoxyphenyl)piperazin-1-carboxylate

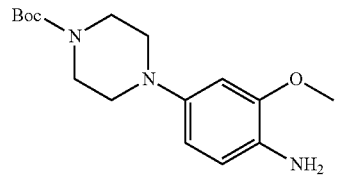

A target compound was obtained in the same manner as in Step 2 of Preparation Example 1 except that N-Boc-piperazine was used instead of N-acetylpiperazine.

¹H-NMR (300 MHz, CDCl₃) δ 6.65 (d, J=8.3 Hz, 1H), 6.51 (s, 1H), 6.41 (d, J=8.3 Hz, 1H), 3.84 (s, 3H), 3.56 (m, 4H), 2.98 (m, 4H), 1.48 (s, 9H).

Preparation Example 35

Preparation of tert-butyl-4-(4-((2,5-dichloropyrimidin-4-yl)amino)-3-methoxyphenyl)piperazin-1-carboxylate

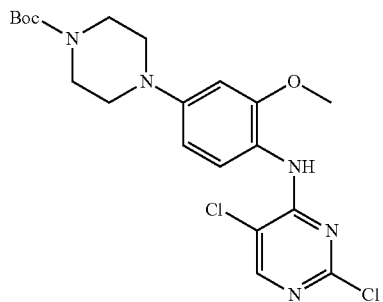 [SMILES: COc1cc(N2CCN(C(=O)OC(C)(C)C)CC2)ccc1Nc1nc(Cl)ncc1Cl]

A target compound was obtained in the same manner as in Preparation Example 21 except that the compound prepared in Preparation Example 34 was used instead of the compound prepared in Preparation Example 8.

¹H-NMR (300 MHz, CDCl₃) δ 8.30 (d, J=8.6 Hz, 1H), 8.13 (s, 1H), 7.88 (s, 1H), 6.62-6.53 (m, 2H), 3.93 (s, 3H), 3.60 (m, 4H), 3.14 (m, 4H), 1.49 (s, 9H).

Example 1

Preparation of 1-(4-(4-(4-(4-(4-acetylpiperazin-1-yl)-2-ethoxyphenylamino)-5-chloropyrimidin-2-ylamino)-3-methoxyphenyl)piperazin-1-yl)ethanone

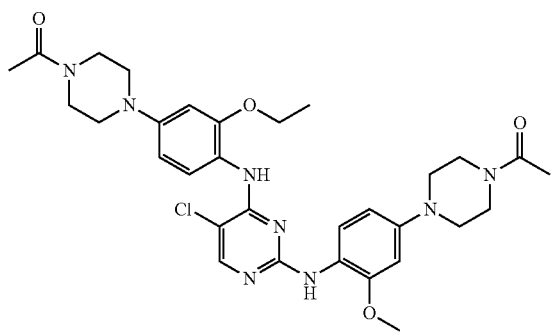 [SMILES: CCOc1cc(N2CCN(C(C)=O)CC2)ccc1Nc1nc(Nc2ccc(N3CCN(C(C)=O)CC3)cc2OC)ncc1Cl]

1-(4-(4-amino-3-methoxyphenyl)piperazin-1-yl)ethanone (40 mg) prepared in Preparation Example 1 and 1-(4-(4-(2,5-dichloropyrimidine-4-ylamino)-3-ethoxyphenyl)piperazin-1-yl)ethanone (50 mg) prepared in Preparation Example 15 were dissolved in 0.08M HCl ethoxyethanol solution (1.2 mL), and allowed to react at 115° C. overnight. Upon completion of the reaction, the solvent of the mixture was removed under reduced pressure, diluted with ethyl acetate, neutralized with an aqueous saturated sodium carbonate solution, water was removed from the organic layer with sodium sulfate, and the solvent was removed under reduced pressure. The mixture was purified by column chromatography to obtain a target compound.

¹H-NMR (300 MHz, CDCl₃) δ 8.36 (d, J=8.5 Hz, 1H), 8.19 (d, J=8.5 Hz, 1H), 8.03 (s, 1H), 7.74 (s, 1H), 7.27 (s, 1H), 6.57-6.52 (m, 4H), 4.14 (q, J=6.7 Hz, 2H), 3.90 (s, 3H), 3.82-3.78 (m, 4H), 3.68-3.65 (m, 4H), 3.18-3.10 (m, 8H), 2.19 (s, 3H), 2.18 (s, 3H), 1.51 (t, J=6.7 Hz, 3H);

Mass (M+H⁺) calcd for $C_{31}H_{39}ClN_8O_4$ 622.27. found 623.01.

Example 2

Preparation of 1-(4-(4-(2-(4-(4-acetylpiperazin-1-yl)-2-methoxyphenylamino)-5-chloropyrimidin-4-ylamino)-3-propoxyphenyl)piperazin-1-yl)ethanone

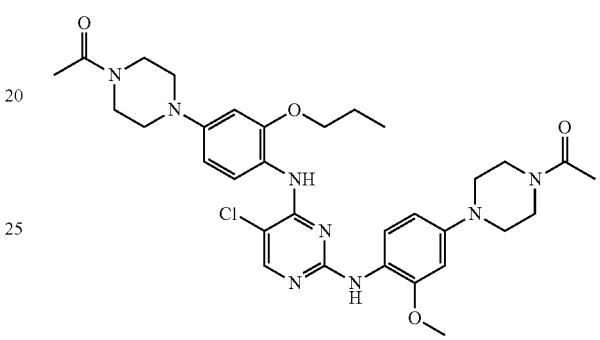

A target compound was obtained in the same manner as in Example 1 except that the compound prepared in Preparation Example 16 was used as a starting material instead of the compound prepared in Preparation Example 15.

¹H-NMR (300 MHz, CDCl₃) δ 8.34 (d, J=9.1 Hz, 1H), 8.14 (d, J=9.1 Hz, 1H), 8.02 (s, 1H), 7.83 (s, 1H), 6.57 (s, 2H), 6.53 (d, J=8.1 Hz, 2H), 4.03 (t, J=6.2 Hz, 2H), 3.90 (s, 3H), 3.82 (t, J=4.8 Hz, 4H), 3.69-3.65 (m, 4H), 3.19-3.11 (m, 8H), 2.19 (s, 3H), 2.18 (s, 3H), 1.91 (sextet, J=13.4, 7.1 Hz, 2H), 1.12 (t, J=7.6 Hz, 3H);

Mass (M+H⁺) calcd for $C_{32}H_{41}ClN_8O_4$ 636.29. found 637.05.

Example 3

Preparation of 1-(4-(4-(4-(4-(4-acetylpiperazin-1-yl)-2-isopropoxyphenylamino)-5-chloropyrimidin-2-ylamino)-3-methoxyphenyl)piperazin-1-yl)ethanone

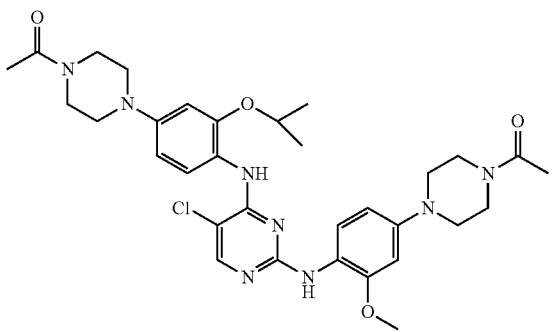 [SMILES: COc1cc(N2CCN(C(C)=O)CC2)ccc1Nc1ncc(Cl)c(Nc2ccc(N3CCN(C(C)=O)CC3)cc2OC(C)C)n1]

A target compound was obtained in the same manner as in Example 1 except that the compound prepared in Preparation Example 17 was used as a starting material instead of the compound prepared in Preparation Example 15.

$^1$H-NMR (300 MHz, CDCl$_3$) δ 8.31 (d, J=8.6 Hz, 1H), 8.11-8.03 (m, 1H), 7.98-7.90 (m, 2H), 6.60-6.46 (m, 4H), 4.64-4.35 (m, 1H), 3.88 (s, 3H), 3.85-3.75 (m, 4H), 3.69-3.60 (m, 4H), 3.20-3.07 (m, 8H), 2.16 (s, 6H), 1.42 (s, 3H), 1.40 (s, 3H);

Mass (M+H$^+$) calcd for C$_{32}$H$_{41}$ClN$_8$O$_4$ 636.29. found 637.05.

Example 4

Preparation of 1-(4-(4-(4-(4-(4-acetylpiperazin-1-yl)-2-propoxyphenylamino)-5-chloropyrimidin-2-ylamino)phenyl)piperazin-1-yl)ethanone

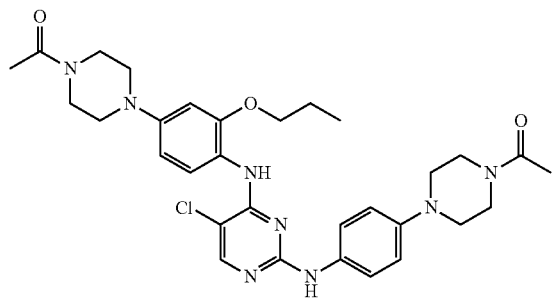 [SMILES: CCCOc1cc(N2CCN(C(C)=O)CC2)ccc1Nc1nc(Nc2ccc(N3CCN(C(C)=O)CC3)cc2)ncc1Cl]

A target compound was obtained in the same manner as in Example 1 except that the compound prepared in Preparation Example 16 was used as a starting material instead of the compound prepared in Preparation Example 15, and 1-(4-(4-aminophenyl)piperazin-1-yl)ethanone was used instead of 1-(4-(4-amino-3-methoxyphenyl)piperazin-1-yl)ethanone.

$^1$H-NMR (300 MHz, CDCl$_3$) δ 8.33 (d, J=8.6 Hz, 1H), 8.02 (s, 1H), 7.81 (s, 1H), 7.47 (d, J=8.6 Hz, 2H), 6.94 (d, J=9.0 Hz, 2H), 6.84 (s, 1H), 6.57 (s, 1H), 6.50 (d, J=9.0 Hz, 1H), 4.03 (t, J=6.27, 2H), 3.83-3.80 (m, 4H), 3.68-3.65 (m, 4H), 3.18-3.11 (m, 8H), 2.19 (s, 3H), 2.18 (s, 3H), 1.91 (sextet, J=14.5, 7.4 Hz, 2H), 1.12 (t, J=7.4 Hz, 3H);

Mass (M+H$^+$) calcd for C$_{31}$H$_{39}$ClN$_8$O$_3$ 606.28. found 607.21.

Example 5

Preparation of 1,1'-(4,4'-(4,4'-(5-fluoropyrimidin-2,4-diyl)bis(azanediyl)bis(3-methoxy-4,1-phenylene))bis(piperazin-4,1-diyl))diethanone

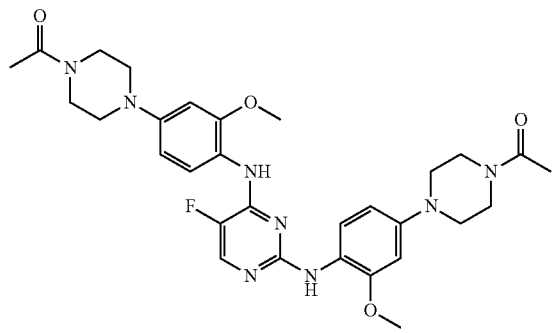 [SMILES: COc1cc(N2CCN(C(C)=O)CC2)ccc1Nc1ncc(F)c(Nc2ccc(N3CCN(C(C)=O)CC3)cc2OC)n1]

A target compound was obtained in the same manner as in Example 1 except that the compound prepared in Preparation Example 33 was used as a starting material instead of the compound prepared in Preparation Example 15.

$^1$H-NMR (300 MHz, CDCl$_3$) δ 8.33 (d, J=8.7 Hz, 1H), 8.18 (d, J=8.7 Hz, 1H), 7.90 (s, 1H), 7.21 (s, 1H), 6.58-6.47 (m, 3H), 3.91 (s, 3H), 3.88 (m, 3H), 3.83-3.74 (m, 4H), 3.70-3.59 (m, 4H), 3.18-3.04 (m, 8H), 2.16 (s, 3H), 2.15 (s, 3H); Mass (M+H$^+$) calcd for C$_{30}$H$_{37}$FN$_8$O$_4$ 592.29. found 592.20.

Example 6

Preparation of 1-(4-(4-(4-(4-(4-acetylpiperazin-1-yl)-2-ethoxyphenylamino)-5-chloropyrimidin-2-ylamino)phenyl)piperazin-1-yl)ethanone

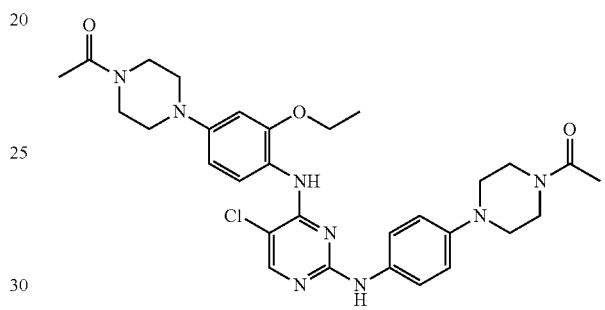

A target compound was obtained in the same manner as in Example 1 except that 1-(4-(4-aminophenyl)piperazin-1-yl)ethanone was used as a starting material instead of the compound prepared in Preparation Example 1.

$^1$H-NMR (300 MHz, CDCl$_3$) δ 8.55 (s, 1H), 8.05 (d, J=8.8 Hz, 1H), 7.81 (s, 1H), 7.61-7.51 (m, 2H), 4.19-4.10 (m, 2H), 4.06-3.95 (m, 2H), 3.93-3.81 (m, 4H), 3.80-3.72 (m, 2H), 3.40-3.19 (m, 8H), 2.18 (s, 6H), 2.15 (t, J=7.24 Hz, 3H);

Mass (M+H$^+$) calcd for C$_{30}$H$_{37}$ClN$_8$O$_3$ 592.26. found 591.15.

Example 7

Preparation of 1,1'-(4,4'-(4,4'-(5-chloropyrimidin-2,4-diyl)bis(azanediyl)bis(3-methoxy-4,1-phenylene))bis(piperazin-4,1-diyl))diethanone

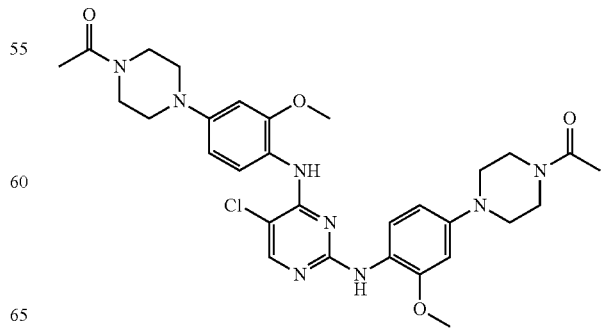

A target compound was obtained in the same manner as in Example 1 except that the compound prepared in Preparation Example 14 was used as a starting material instead of the compound prepared in Preparation Example 15.

$^1$H-NMR (300 MHz, CDCl$_3$) δ 8.29 (d, J=8.6 Hz, 1H), 8.15 (d, J=8.6 Hz, 1H), 8.01 (s, 1H), 7.57 (s, 1H), 6.53 (m, 4H), 3.92 (s, 3H), 3.88 (s, 3H), 3.81 (m, 4H), 3.67 (m, 4H), 3.12 (m, 8H), 2.16 (s, 3H), 2.15 (s, 3H);

Mass (M+H$^+$) calcd for C$_{30}$H$_{37}$ClN$_8$O$_4$ 608.26. found 609.17.

Example 8

Preparation of 1-(4-(4-(2-(4-(4-acetylpiperazin-1-yl)-2-methoxyphenylamino)-5-chloropyrimidin-4-ylamino)phenyl)piperazin-1-yl)ethanone

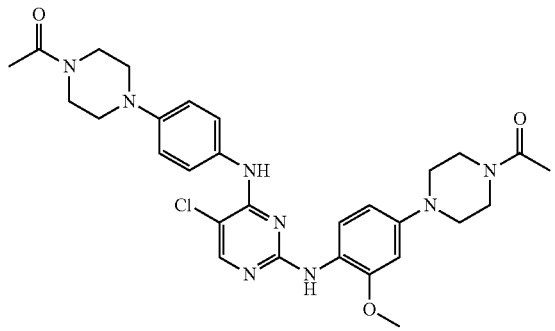 [SMILES: COc1cc(N2CCN(C(C)=O)CC2)ccc1Nc1ncc(Cl)c(Nc2ccc(N3CCN(C(C)=O)CC3)cc2)n1]

A target compound was obtained in the same manner as in Example 1 except that the compound prepared in Preparation Example 32 was used as a starting material instead of the compound prepared in Preparation Example 15.

$^1$H-NMR (300 MHz, CDCl$_3$) δ 8.12 (d, J=8.8 Hz, 1H), 8.02 (s, 1H), 7.50 (d, J=8.9 Hz, 2H), 7.28 (s, 1H), 6.95 (d, J=8.9 Hz, 2H), 6.92 (s, 1H), 6.52 (d, J=2.5 Hz, 1H), 6.42 (dd, J=2.5, 8.0 Hz, 1H), 3.86 (s, 3H), 3.80 (m, 4H), 3.62 (m, 4H), 3.19 (m, 4H), 3.08 (m, 4H), 2.16 (s, 3H), 2.15 (s, 3H);

Mass (M+H$^+$) calcd for C$_{29}$H$_{35}$ClN$_8$O$_3$ 578.25. found 579.13.

Example 9

Preparation of 1,1'-(4,4'-(4,4'-(5-chloropyrimidin-2,4-diyl)bis(azanediyl)bis(4,1-phenylene))bis(piperazin-4,1-diyl))diethanone

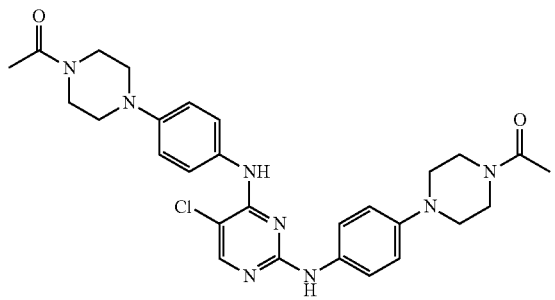 [SMILES: CC(=O)N1CCN(c2ccc(Nc3ncc(Cl)c(Nc4ccc(N5CCN(C(C)=O)CC5)cc4)n3)cc2)CC1]

A target compound was obtained in the same manner as in Example 1 except that the compound prepared in Preparation Example 32 was used as a starting material instead of the compound prepared in Preparation Example 15, and 1-(4-(4-aminophenyl)piperazin-1-yl)ethanone was used instead of the compound prepared in Preparation Example 1.

$^1$H-NMR (300 MHz, CDCl$_3$) δ 8.01 (s, 1H), 7.48 (d, J=8.9 Hz, 2H), 7.41 (d, J=9.0 Hz, 2H), 6.93 (d, J=8.9 Hz, 2H), 6.92 (s, 1H), 6.87 (d, J=9.0 Hz, 2H), 6.76 (s, 1H), 3.79 (m, 4H), 3.63 (m, 4H), 3.16 (m, 4H), 3.10 (m, 4H), 2.16 (s, 3H), 2.15 (s, 3H);

Mass (M+H$^+$) calcd for C$_{28}$H$_{33}$ClN$_8$O$_2$ 548.24. found 549.17.

Example 10

Preparation of 1-(4-(4-(4-(4-acetylpiperazin-1-yl)-2-methoxyphenylamino)-5-chloropyrimidin-2-ylamino)phenyl)piperazin-1-yl)ethanone

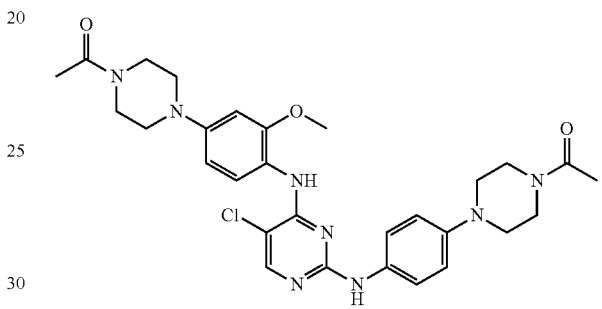

A target compound was obtained in the same manner as in Example 1 except that the compound prepared in Preparation Example 14 was used as a starting material instead of the compound prepared in Preparation Example 15, and 1-(4-(4-aminophenyl)piperazin-1-yl)ethanone was used instead of the compound prepared in Preparation Example 1.

$^1$H-NMR (300 MHz, CDCl$_3$) δ 8.26 (d, J=8.8 Hz, 1H), 8.00 (s, 1H), 7.61 (s, 1H), 7.43 (m, 2H), 6.90 (m, 2H), 6.79 (s, 1H), 6.55 (s, 1H), 6.49 (d, J=8.8 Hz, 1H), 3.90 (s, 3H), 3.80 (m, 4H), 3.63 (m, 4H), 3.12 (m, 8H), 2.16 (s, 3H), 2.15 (s, 3H);

Mass (M+H$^+$) calcd for C$_{29}$H$_{35}$ClN$_8$O$_3$ 578.25. found 579.07.

Example 11

Preparation of 1,1'-(4,4'-(4,4'-(5-(trifluoromethyl)pyrimidin-2,4-diyl)bis(azanediyl)bis(3-methoxy-4,1-phenylene))bis(piperazin-4,1-diyl))diethanone

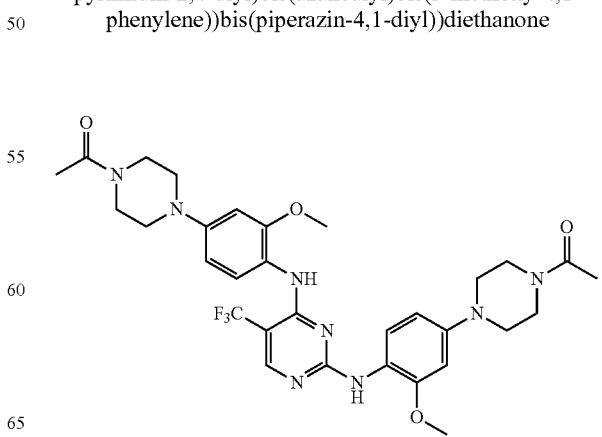

1-(4-(4-amino-3-methoxyphenyl)piperazin-1-yl)ethanone (250 mg) prepared in Preparation Example 1 and potassium carbonate (120 mg) were dissolved in DMF (2 mL), slowly added with 2,4-dichloro-5-(trifluoromethyl)pyrimidine (100 mg) at 0° C., and stirred at 100° C. overnight. Upon completion of the reaction, the dimethylformamide in the mixture was removed under reduced pressure, added with water to form a solid, and filtered to obtain a target compound as a white solid.

$^1$H-NMR (300 MHz, CDCl$_3$) δ 8.27 (s, 1H), 8.15 (m, 2H), 7.44 (s, 1H), 7.39 (s, 1H), 6.54 (m, 2H), 6.51 (m, 1H), 6.42 (m, 1H), 3.89 (s, 3H), 3.88 (s, 3H), 3.80 (m, 4H), 3.70 (m, 4H), 3.16 (m, 8H), 2.17 (s, 6H);

Mass (M+H$^+$) calcd for C$_{31}$H$_{37}$F$_3$N$_8$O$_4$ 642.29. found 643.06.

Example 12

Preparation of 1-(4-(4-(5-chloro-4-(2-methoxy-4-(piperazin-1-yl)phenylamino)pyrimidin-2-ylamino)-3-methoxyphenyl)piperazin-1-yl)ethanone

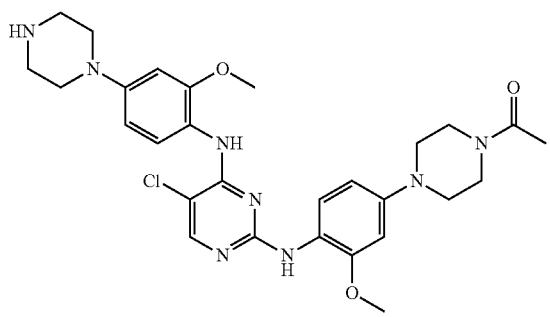

Step 1: Preparation of tert-butyl-4-(4-(2-(4-(4-acetylpiperazin-1-yl)-2-methoxyphenylamino)-5-chloropyrimidin-4-ylamino)-3-methoxyphenyl)piperazin-1-carboxylate A target compound was obtained in the same manner as in Example 1 except that the compound prepared in Preparation Example 35 was used as a starting material instead of the compound prepared in Preparation Example 15.

Step 2: Preparation of 1-(4-(4-(5-chloro-4-(2-methoxy-4-(piperazin-1-yl)phenylamino)pyrimidin-2-ylamino)-3-methoxyphenyl)piperazin-1-yl)ethanone The compound prepared in Step 1 was dissolved in methylenechloride (10 ml), added with 4M HCl (dioxane solution, 2 ml), and stirred at room temperature overnight. Then, the mixture was distilled under reduced pressure, and dissolved in methylenechloride. The mixed solution was neutralized with an saturated aqueous solution of sodium bicarbonate, washed with brine, and the organic layer was dried with sodium sulfate. The dried organic layer was concentrated under reduced pressure and the target compound was obtained without further purification.

$^1$H-NMR (300 MHz, CDCl$_3$) δ 7.89 (s, 1H), 7.77-7.70 (m, 2H), 6.67-6.64 (m, 2H), 6.49-6.47 (m, 1H), 6.41-6.38 (m, 1H), 3.84 (s, 6H), 3.75-3.64 (m, 4H), 3.17-3.06 (m, 8H), 3.02-2.97 (m, 4H), 2.15 (s, 3H);

Mass (M+H$^+$) calcd for C$_{28}$H$_{35}$ClN$_8$O$_3$ 566.25. found 566.92.

Example 13

Preparation of 1-(4-(4-(5-chloro-4-(2-methoxy-4-(4-(methylsulfonyl)piperazin-1-yl)phenylamino)pyrimidin-2-ylamino)-3-methoxyphenyl)piperazin-1-yl)ethanone

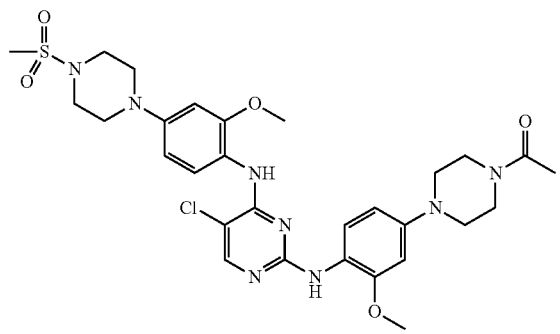 [SMILES: COc1cc(N2CCN(C(C)=O)CC2)ccc1Nc1ncc(Cl)c(Nc2ccc(N3CCN(S(C)(=O)=O)CC3)cc2OC)n1]

The compound (20 mg) prepared in Example 12 was dissolved in methylenechloride (1 mL), stirred at 0° C., added with triethylamine (10 μl) and methanesulfonylchloride (10 μl), and stirred at 0° C. In 5 minutes, a small amount of methanol was added thereto, and the solvent of the reaction mixture was removed under reduced pressure. The mixture was purified with HPLC to obtain a target compound.

$^1$H-NMR (300 MHz, CDCl$_3$) δ 9.37 (s, 1H), 8.16 (s, 1H), 7.35-7.26 (m, 2H), 6.75 (s, 1H), 6.65 (s, 1H), 6.54 (d, J=8.5 Hz, 1H), 6.35-6.30 (m, 1H), 3.79 (s, 6H), 3.59-3.57 (m, 4H), 3.30-3.27 (m, 8H), 3.16-3.10 (m, 4H), 2.96 (s, 3H), 2.20 (s, 3H);

Mass (M+H$^+$) calcd for C$_{29}$H$_{37}$ClN$_8$O$_5$S 644.23. found 644.88.

Example 14

Preparation of 1-(4-(4-(2-(4-(4-acetylpiperazin-1-yl)-2-methoxyphenylamino)-5-chloropyrimidin-4-ylamino)-3-methoxyphenyl)piperazin-1-yl)-2-hydroxyethanone

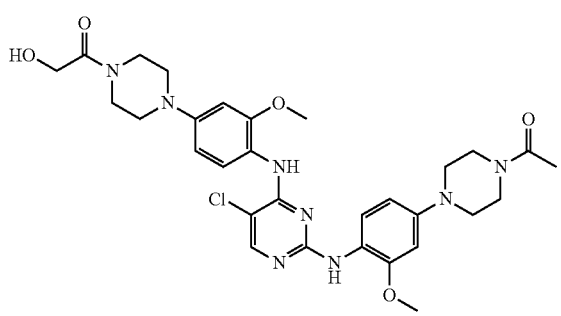

The compound (20 mg) prepared in Example 12, glycolic acid (8 mg), EDCI (20 mg) and DMAP (5.4 mg) were dissolved in methylenechloride (1 ml), and stirred at room temperature for 3 hours. Upon completion of the reaction, the solvent was removed under reduced pressure, and the mixture removed of the solvent was diluted with ethyl acetate, and washed with a saturated aqueous solution of ammonium chloride. The water in the thus obtained organic layer was removed with sodium sulfate and the solvent was removed under reduced pressure. The reaction mixture was purified by column chromatography to obtain a target compound as a white solid.

$^1$H-NMR (300 MHz, CDCl$_3$) δ 8.59 (d, J=8.4 Hz, 1H), 8.13 (d, J=8.4 Hz, 1H), 8.01 (s, 1H), 7.29 (s, 1H), 6.59-6.47 (m, 3H), 4.24 (s, 2H), 3.94-3.74 (m, 10H), 3.69-3.60 (m, 2H), 3.53-3.44 (m, 2H), 3.22-3.00 (m, 8H), 2.16 (s, 3H);

Mass (M+H1 calcd for C$_{30}$H$_{37}$ClN$_8$O$_5$ 624.25. found 624.90.

Example 15

Preparation of tert-butyl 4-(4-(2-(4-(4-acetylpiperazin-1-yl)-2-methoxyphenylamino)-5-chloropyrimidin-4-ylamino)-3-methoxyphenyl)piperazin-1-carboxylate

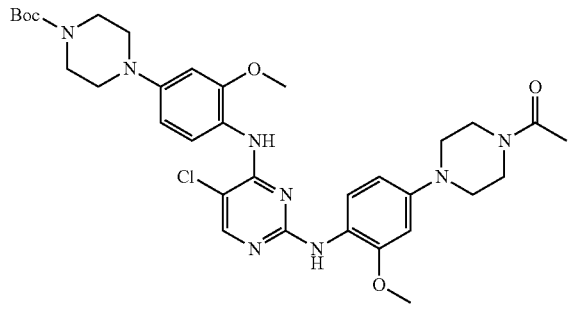 [SMILES: COc1cc(N2CCN(C(C)=O)CC2)ccc1Nc1ncc(Cl)c(Nc2ccc(N3CCN(C(=O)OC(C)(C)C)CC3)cc2OC)n1]

A target compound as a white solid was obtained in the same manner as in Step 1 of Example 12.

$^1$H-NMR (300 MHz, CDCl$_3$) δ 8.27 (d, J=8.9 Hz, 1H), 8.16 (d, J=8.5 Hz, 1H), 8.01 (s, 1H), 7.56 (s, 1H), 6.58-6.48 (m, 5H), 3.67-3.56 (m, 6H), 3.16-3.05 (m, 8H), 2.15 (s, 3H), 1.49 (s, 9H);

Mass (M+H$^+$) calcd for C$_{33}$H$_{43}$ClN$_8$O$_5$ 666.30. found 667.02.

Example 16

Preparation of 1-(4-(4-(5-chloro-4-(4-(4-(2-hydroxyethyl)piperazin-1-yl)-2-methoxyphenylamino)pyrimidin-2-ylamino)-3-methoxyphenyl)piperazin-1-yl)ethanone

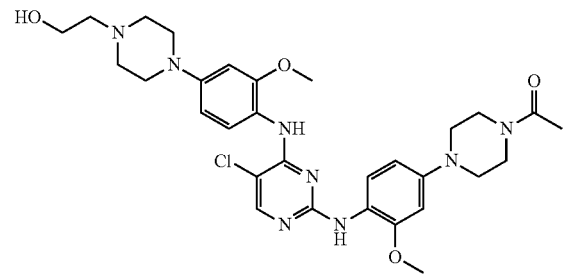 [SMILES: COc1cc(N2CCN(C(C)=O)CC2)ccc1Nc1ncc(Cl)c(Nc2ccc(N3CCN(CCO)CC3)cc2OC)n1]

The compound (30 mg) prepared in Example 12, 2-bromoethanol (5.7 μl) and potassium carbonate (22 mg) were dissolved in dimethylformamide (1.5 mL), and reacted at 60° C. overnight. Upon completion of the reaction, dimethylformamide was removed under reduced pressure, added with water, and extracted with ethyl acetate. The thus obtained organic layer was washed with saturated brine, the water was removed with sodium sulfate, and the solvent was removed under reduced pressure, and the mixture was purified by HPLC to obtain a target compound as a yellow oil.

$^1$H-NMR (300 MHz, CDCl$_3$) δ 7.98 (s, 1H), 7.70 (d, J=9.0 Hz, 1H), 7.35 (d, J=9.0 Hz, 1H), 6.78 (s, 1H), 6.71 (s, 1H), 6.59 (d, J=9.9 Hz, 1H), 6.50 (d, J=9.0 Hz, 1H), 4.05-3.99 (m, 2H), 3.96 (t, J=4.9 Hz, 2H), 3.90 (s, 3H), 3.86 (s, 3H), 3.83-3.69 (m, 6H), 3.56-3.45 (m, 2H), 3.39 (t, J=4.9 Hz, 2H), 3.29-3.19 (m, 6H), 2.17 (s, 3H);

Mass (M+H$^+$) calcd for C$_{30}$H$_{39}$ClN$_8$O$_4$ 610.27. found 610.93.

Example 17

Preparation of 1-(4-(4-(4-(4-(4-acetylpiperazin-1-yl)-2-(benzyloxy)phenylamino)-5-chloropyrimidin-2-ylamino)-3-methoxyphenyl)piperazin-1-yl)ethanone

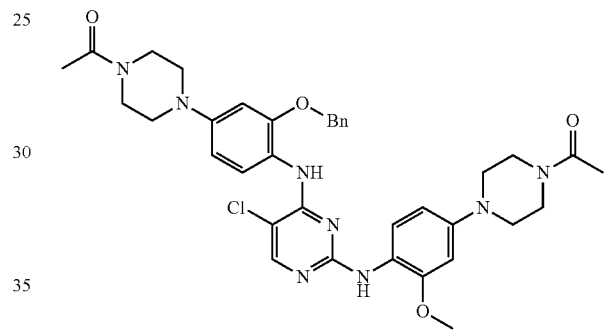

A target compound was obtained in the same manner as in Example 1 except that the compound prepared in Preparation Example 18 was used instead of the compound prepared in Preparation Example 15.

$^1$H-NMR (300 MHz, DMSO-d$_6$) δ 9.25 (br, 1H), 8.13 (s, 1H), 7.31 (m, 7H), 6.84 (d, J=2.4 Hz, 1H), 6.65 (d, J=2.4 Hz, 1H), 6.53 (dd, J=2.4, 8.6 Hz, 1H), 6.32 (br, 1H), 5.13 (s, 2H), 3.77 (s, 3H), 3.15 (m, 7H), 2.07 (s, 3H), 2.05 (s, 3H);

Mass (M+H$^+$) calcd for C$_{36}$H$_{41}$ClN$_8$O$_4$ 684.29. found 684.84.

Example 18

Preparation of 1,1'-(4,4'-(4,4'-(5-bromopyrimidin-2,4-diyl)bis(azanediyl)bis(3-methoxy-4,1-phenylene))bis(piperazin-4,1-diyl))diethanone

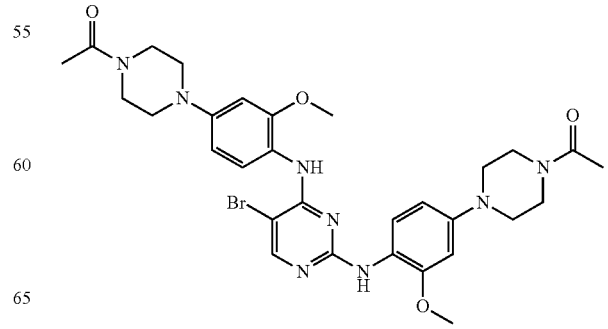

1-(4-(4-amino-3-methoxyphenyl)piperazin-1-yl)ethanone (200 mg) and potassium carbonate (230 mg) were dissolved in dimethylformamide (3 ml), and slowly added with 5-bromo-2,4-dichloropyrimidine (70 mg) at 0° C., and stirred at 100° C. overnight. Upon completion of the reaction, the dimethylformamide of the reaction mixture was removed under reduced pressure, added with water to form a solid, and filtered to obtain a target compound as a white solid.

$^1$H-NMR (300 MHz, DMSO-$d_6$) δ 9.10 (br, 1H), 8.15 (br, 1H), 7.30 (br, 1H), 7.20 (br, 1H), 6.68 (br, 1H), 6.60 (br, 1H), 6.42 (m, 1H), 6.23 (br, 1H), 3.71 (s, 6H), 3.50 (m, 4H), 3.41 (m, 4H), 3.08 (m, 8H), 1.99 (s, 6H);

Mass (M+H$^+$) calcd for $C_{30}H_{37}BrN_8O_4$ 652.21. found 652.85.

Example 19

Preparation of 1,1'-(4,4'-(4,4'-(pyrimidin-2,4-diylbis (azanediyl))bis(3-methoxy-4,1-phenylene))bis(piper-azin-4,1-diyl))diethanone

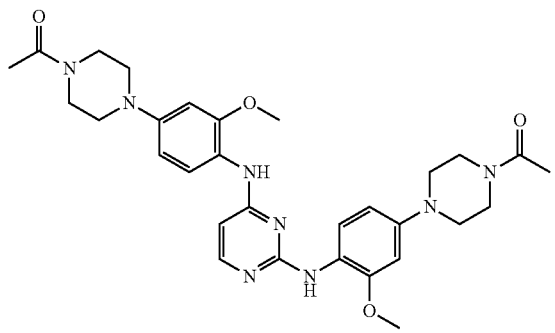 [SMILES: COc1cc(N2CCN(C(C)=O)CC2)ccc1Nc1ccnc(Nc2ccc(N3CCN(C(C)=O)CC3)cc2OC)n1]

A target compound was obtained in the same manner as in Example 1 except that the compound prepared in Preparation Example 31 was used as a starting material instead of the compound prepared in Preparation Example 15, followed by a further purification by a reverse phase HPLC.

$^1$H-NMR (300 MHz, DMSO-$d_6$) δ 11.64 (br, 1H), 10.0 (s, 1H), 9.51 (br, 1H), 7.72 (br, 1H), 7.46 (br, 1H), 7.28 (br, 1H), 6.69 (s, 2H), 6.56 (br, 1H), 6.48 (s, 1H), 6.46 (s, 1H), 3.81 (s, 3H), 3.79 (s, 3H), 3.16 (m, 8H), 2.01 (s, 6H);

Mass (M+H$^+$) calcd for $C_{30}H_{38}FN_8O_4$ 574.30. found 574.95.

Example 20

Preparation of methyl 4-(4-(2-(4-(4-acetylpiperazin-1-yl)-2-methoxyphenylamino)-5-chloropyrimidin-4-ylamino)-3-methoxyphenyl)piperazin-1-carboxylate

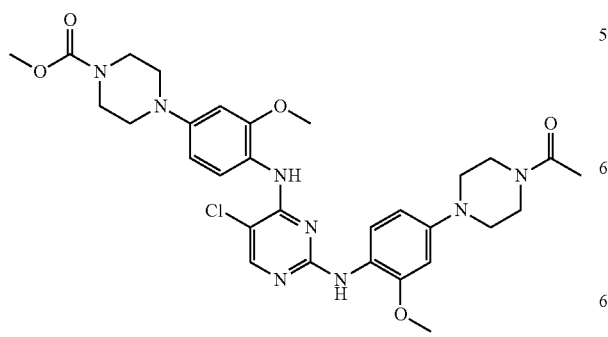

A target compound as a white solid was obtained in the same manner as in Example 13 except that methylcarbonochloridate was used instead of methane sulfonylchloride.

$^1$H-NMR (300 MHz, CD$_3$OD) δ 7.98 (s, 1H), 7.55 (s, 1H), 7.59 (d, J=9.2 Hz, 1H), 6.76-6.69 (m, 3H), 6.52 (d, J=7.6 Hz, 1H), 6.47 (d, J=7.6 Hz, 1H), 3.92 (s, 1H), 3.90-3.83 (m, 6H), 3.79-3.73 (m, 3H), 3.72-3.61 (m, 8H), 3.29-3.17 (m, 8H), 2.17 (s, 3H);

Mass (M+H$^+$) calcd for $C_{30}H_{37}ClN_8O_5$ Exact Mass: 624.26. found 624.90.

Example 21

Preparation of 4-(4-(2-(4-(4-acetylpiperazin-1-yl)-2-methoxyphenylamino)-5-chloropyrimidin-4-ylamino)-3-methoxyphenyl)piperazin-1-sulfonamide

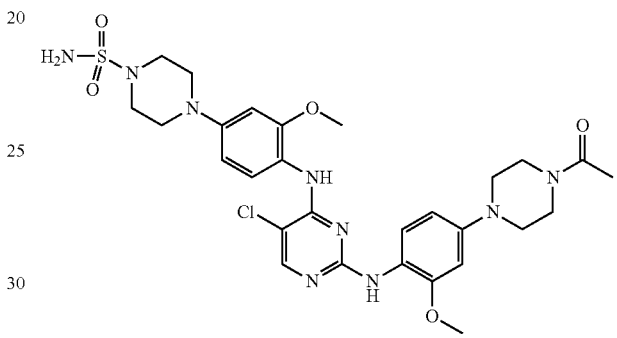

A target compound as a white solid was obtained in the same manner as in Example 14 except that triethylamine (10 μl) was added using disulfide and refluxed for 2 hours instead of using glycolic acid.

$^1$H-NMR (300 MHz, CD$_3$OD) δ 7.99 (s, 1H), 7.48 (s, 1H), 7.28 (d, J=8.6 Hz, 1H), 6.73 (s, 1H), 6.68 (s, 1H), 6.58 (d, J=9.2 Hz, 1H), 6.42 (s, 1H), 4.22 (s, 1H), 3.84 (s, 6H), 3.76-3.69 (m, 4H), 3.35-3.17 (m, 12H), 2.16 (s, 3H);

Mass (M+H$^+$) calcd for $C_{28}H_{36}ClN_9O_5S$ Exact Mass: 645.22. found 645.89.

Example 22

Preparation of 1-(4-(4-(2-(4-(4-acetylpiperazin-1-yl)-2-methoxyphenylamino)-5-chloropyrimidin-4-ylamino)-3-methoxyphenyl)piperazin-1-yl)propan-1-one

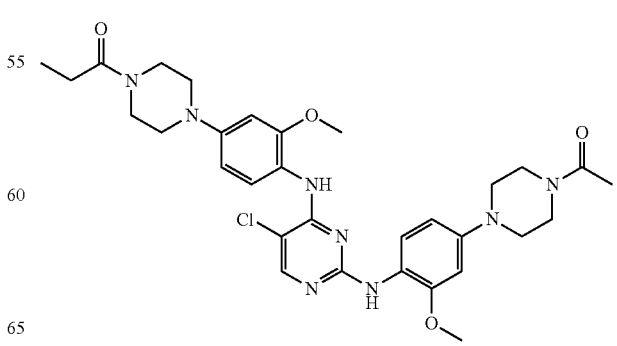

A target compound as a white solid was obtained in the same manner as in Example 13 except that propionic acid was used instead of methanesulfonylchloride.

$^1$H-NMR (300 MHz, DMSO-d$_6$) δ 9.35 (s, 1H), 8.16 (s, 1H), 7.30 (m, 2H), 6.72 (s, 1H), 6.65 (s, 1H), 6.50 (d, J=8.9 Hz, 1H), 6.30 (m, 1H), 3.78 (s, 6H), 3.17 (m, 12H), 2.38 (q, J=7.4 Hz, 2H), 2.05 (s, 3H), 1.02 (t, J=7.4 Hz, 3H);

Mass (M+H$^+$) calcd for C$_{31}$H$_{39}$ClN$_8$O$_4$ Exact Mass: 622.28. found 623.12.

Example 23

Preparation of 1-(4-(4-(2-(4-(4-acetylpiperazin-1-yl)-2-methoxyphenylamino)-5-chloropyrimidin-4-ylamino)-3-methoxyphenyl)piperazin-1-yl)-2,2-dimethylpropan-1-one

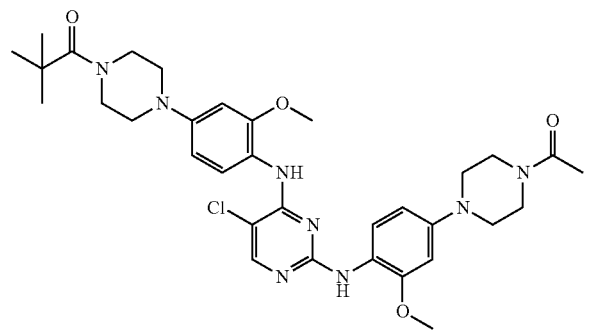 [SMILES: COc1cc(N2CCN(C(C)=O)CC2)ccc1Nc1ncc(Cl)c(Nc2ccc(N3CCN(C(=O)C(C)(C)C)CC3)cc2OC)n1]

A target compound was obtained in the same manner as in Example 13 except that pivaloyl chloride was used instead of methanesulfonylchloride.

$^1$H-NMR (300 MHz, CD$_3$OD) δ 7.90 (s, 1H), 7.79 (d, J=8.7 Hz, 1H), 7.74 (d, J=8.7 Hz, 1H), 6.69 (s, 1H), 6.63 (s, 1H), 6.48 (d, J=8.1 Hz, 1H), 6.36 (d, J=9.8 Hz, 1H), 3.85 (s, 3H), 3.84 (s, 3H), 3.82-3.77 (m, 4H), 3.67 (dt, J=16.8, 4.6 Hz, 4H), 3.19-3.03 (m, 8H), 2.13 (s, 3H), 1.30 (s, 9H);

Mass (M+H$^+$) calcd for C$_{33}$H$_{43}$ClN$_8$O$_4$ Exact Mass: 650.31. found 650.96.

Example 24

Preparation of 1-(4-(4-(4-(4-(4-acetylpiperazin-1-yl)-2-methoxyphenylamino)-5-fluoropyrimidin-2-ylamino)phenyl)piperazin-1-yl)ethanone

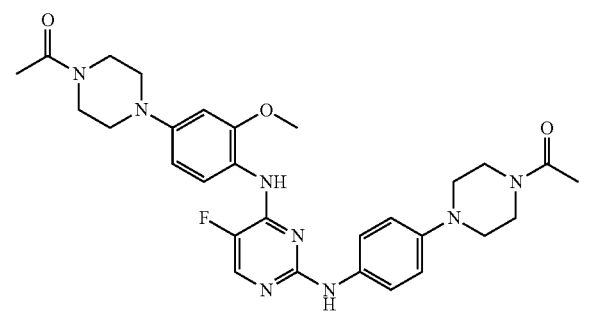 [SMILES: COc1cc(N2CCN(C(C)=O)CC2)ccc1Nc1nc(Nc2ccc(N3CCN(C(C)=O)CC3)cc2)ncc1F]

A target compound was obtained in the same manner as in Example 1 except that the compound prepared in Preparation Example 33 was used as a starting material instead of the compound prepared in Preparation Example 15, and 1-(4-(4-aminophenyl)piperazin-1-yl)ethanone was used instead of 1-(4-(4-amino-3-methoxyphenyl)piperazin-1-yl)ethanone.

$^1$H NMR (300 MHz, CDCl$_3$) δ 8.30 (d, J=8.7 Hz, 1H), 7.89 (s, 1H), 7.45 (d, J=8.5 Hz, 2H), 6.91 (d, J=8.5 Hz, 2H), 6.80 (s, 1H), 6.55 (s, 1H), 6.50 (d, J=8.7 Hz, 1H), 3.91 (s, 3H), 3.79 (d, J=4.3 Hz, 4H), 3.64 (d, J=4.3 Hz, 4H), 3.12 (t, J=4.3 Hz, 8H), 2.15 (s, 6H);

Mass (M+H$^+$) calcd for C$_{29}$H$_{35}$FN$_8$O$_3$ 562.64. found 562.89.

Example 25

Preparation of 1-(4-(4-(5-fluoro-4-(2-methoxy-4-(piperazin-1-yl)phenylamino)pyrimidin-2-ylamino)-3-methoxyphenyl)piperazin-1-yl)ethanone

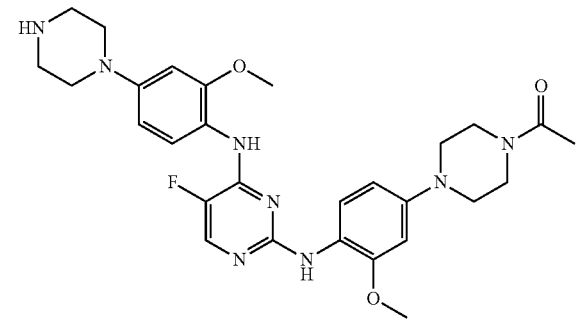 [SMILES: COc1cc(N2CCN(C(C)=O)CC2)ccc1Nc1ncc(F)c(Nc2ccc(N3CCNCC3)cc2OC)n1]

Step 1: Preparation of tert-butyl-4-(4-(2-(4-(4-acetylpiperazin-1-yl)-2-methoxyphenylamino)-5-fluoropyrimidin-4-ylamino)-3-methoxyphenyl)piperazin-1-carboxylate A target compound was obtained in the same manner as in Example 1 except that the compound prepared in Preparation Example 27 was used as a starting material instead of the compound prepared in Preparation Example 15.

Step 2: Preparation of 1-(4-(4-(5-fluoro-4-(2-methoxy-4-(piperazin-1-yl)phenylamino)pyrimidin-2-ylamino)-3-methoxyphenyl)piperazin-1-yl)ethanone A target compound was obtained in the same manner as in Step 2 of Example 12 except that the compound prepared in Step 1 above was used as a starting material instead of the compound prepared in Step 1 of Example 12.

$^1$H NMR (300 MHz, CDCl$_3$) δ 7.81 (s, 1H), 7.79 (d, J=11 Hz, 1H), 7.69 (d, J=8 Hz, 1H), 6.69 (s, 1H), 6.64 (s, 1H), 6.53 (d, J=8.0 Hz, 1H), 6.40 (d, J=11 Hz, 1H), 3.84 (s, 6H), 3.75-3.67 (m, 4H), 3.18-2.99 (m, 12H), 2.15 (s, 3H);

Mass (M+H⁺) calcd for $C_{28}H_{35}FN_8O_3$ Exact Mass: 550.63. found 551.16.

Example 26

Preparation of 1-(4-(4-(5-fluoro-4-(2-methoxy-4-(4-(methylsulfonyl)piperazin-1-yl)phenylamino)pyrimidin-2-ylamino)-3-methoxyphenyl)piperazin-1-yl)ethanone

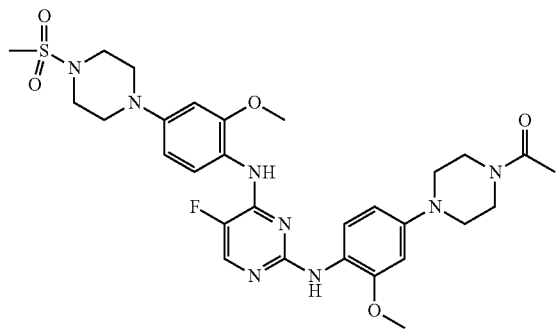 [SMILES: COc1cc(N2CCN(C(C)=O)CC2)ccc1Nc1ncc(F)c(Nc2ccc(N3CCN(S(C)(=O)=O)CC3)cc2OC)n1]

A target compound was obtained in the same manner as in Example 13 except that the compound prepared in Example 25 was used as a starting material instead of the compound prepared in Example 12.

$^1$H NMR (300 MHz, CDCl₃) δ 8.35 (d, J=8.8 Hz, 1H), 8.18 (d, J=8.8 Hz, 1H), 7.91 (s, 1H), 7.22 (s, 1H), 6.55 (d, J=7.5 Hz, 1H), 3.91 (s, 3H), 3.88 (m, 3H), 3.78 (d, J=4.0 Hz, 2H), 3.64 (s, 2H), 3.42 (d, J=4.0 Hz, 4H), 3.27 (d, J=4.0 Hz, 4H), 3.10 (s, 4H), 2.85 (s, 3H), 2.15 (s, 3H);

Mass (M+H⁺) calcd for $C_{29}H_{37}FN_8O_5S$ 628.72. found 628.88.

Example 27

Preparation of methyl 4-(4-(2-(4-(4-acetylpiperazin-1-yl)-2-methoxyphenylamino)-5-fluoropyrimidin-4-ylamino)-3-methoxyphenyl)piperazin-1-carboxylate

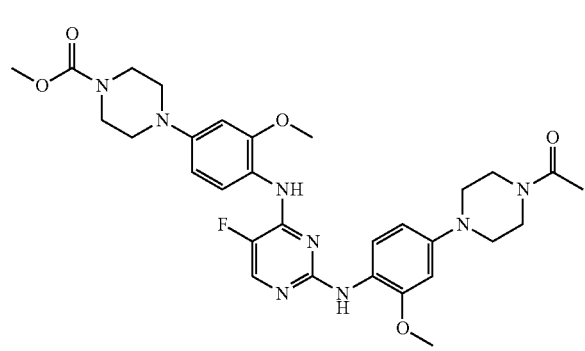 [SMILES: COC(=O)N1CCN(c2ccc(Nc3nc(Nc4ccc(N5CCN(C(C)=O)CC5)cc4OC)ncc3F)c(OC)c2)CC1]

A target compound was obtained in the same manner as in Example 13 except that the compound prepared in Example 25 was used as a starting material instead of the compound prepared in Example 12.

$^1$H NMR (300 MHz, CD₃OD) δ 8.31 (d, J=8.6 Hz, 1H), 8.18 (d, J=8.6 Hz, 1H), 7.89 (s, 1H), 6.55 (d, J=5.1 Hz, 3H), 3.90 (s, 3H), 3.88 (s, 3H), 3.78 (d, J=4.2 Hz, 2H), 3.74 (s, 3H), 3.65 (s, 6H), 3.11 (d, J=4.2 Hz, 8H), 2.15 (s, 3H);

Mass (M+H⁺) calcd for $C_{30}H_{37}FN_8O_5$ 608.66. found 608.97.

Example 28

Preparation of 1-(4-(4-(5-fluoro-4-(4-(4-(2-hydroxyethyl)piperazin-1-yl)-2-methoxyphenylamino)pyrimidin-2-ylamino)-3-methoxyphenyl)piperazin-1-yl)ethanone

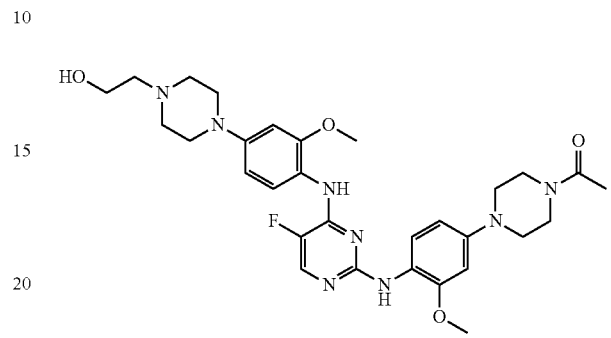

A target compound was obtained in the same manner as in Example 16 except that the compound prepared in Example 25 was used as a starting material instead of the compound prepared in Example 12.

$^1$H NMR (500 MHz, CD₃OD) δ 8.29 (d, J=8.5 Hz, 1H), 8.17 (d, J=8.5 Hz, 1H), 7.89 (s, 1H), 7.21 (s, 1H), 6.55 (s, 2H), 6.54 (s, 1H), 6.51 (d, J=8.6 Hz, 1H), 3.90 (s, 3H), 3.87 (s, 3H), 3.79 (t, J=4.9 Hz, 2H), 3.71 (t, J=5.1 Hz, 2H), 3.63 (t, J=4.9 Hz, 2H), 3.22 (t, J=4.6 Hz, 4H), 3.11 (t, J=4.9 Hz, 2H), 3.08 (t, J=4.9 Hz, 2H), 2.76 (t, J=4.6 Hz, 4H), 2.67 (t, J=5.1 Hz, 2H), 2.15 (s, 3H);

Mass (M+H⁺) calcd for $C_{30}H_{39}FN_8O_4$ 594.68. found 594.93.

Example 29

Preparation of 1-(4-(4-(4-(4-acetylpiperazin-1-yl)-2-ethoxyphenylamino)-5-fluoropyrimidin-2-ylamino)-3-methoxyphenyl)piperazin-1-yl)ethanone

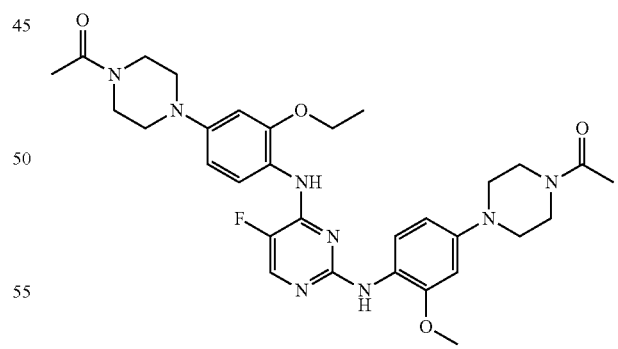

Step 1: Preparation of 1-(4-(4-(2-chloro-5-fluoropyrimidin-4-ylamino)-3-ethoxyphenyl)piperazin-1-yl)ethanone A target compound was obtained in the same manner as in Preparation Example 33 except that the compound prepared in Preparation Example 2 was used as a starting material instead of the compound prepared in Preparation Example 1.

Step 2: Preparation of 1-(4-(4-(4-(4-(4-acetylpiper-azin-1-yl)-2-ethoxyphenylamino)-5-fluoropyrimidin-2-ylamino)-3-methoxyphenyl)piperazin-1-yl)ethanone A target compound (21 mg, 28%) was obtained in the same manner as in Example 1 except that the compound prepared in Step 1 of Preparation Example 29 was used as a starting material instead of the compound prepared in Preparation Example 15.

¹H NMR (300 MHz, CDCl₃) δ 8.35 (d, J=8.0 Hz, 1H), 8.19 (d, J=8.0 Hz, 1H), 7.90 (s, 1H), 7.31 (s, 1H), 7.21 (s, 1H), 6.52 (s, 3H), 6.51 (s, 1H), 4.12 (q, J=6.8 Hz, 2H), 3.88 (s, 3H), 3.79 (s, 4H), 3.64 (s, 4H), 3.16-3.08 (m, 8H), 2.15 (s, 6H) 1.47 (t, J=6.8 Hz, 3H);

Mass (M+H⁺) calcd for $C_{31}H_{39}FN_8O_4$ 606.69. found 606.94.

Example 30

Preparation of 1-(4-(4-(5-fluoro-4-(2-methoxy-4-(4-methylpiperazin-1-yl)phenylamino)pyrimidin-2-ylamino)-3-methoxyphenyl)piperazin-1-yl)ethanone

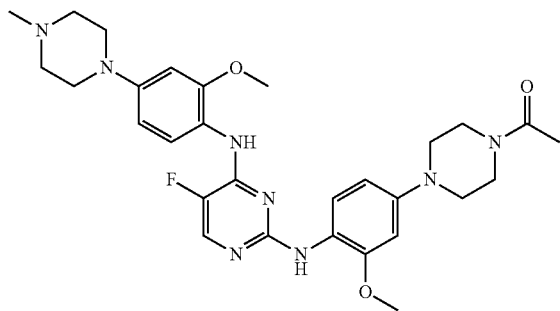 [SMILES: COc1cc(N2CCN(C(C)=O)CC2)ccc1Nc1ncc(F)c(Nc2ccc(N3CCN(C)CC3)cc2OC)n1]

A target compound was obtained in the same manner as in Example 13 except that methyliodide was used instead of methanesulfonylchloride.

¹H NMR (300 MHz, CD₃OD) δ 8.28 (d, J=8.0 Hz, 1H), 8.19 (d, J=8.0 Hz, 1H), 7.88 (s, 1H), 7.20 (s, 1H), 6.55 (d, J=7.7 Hz, 3H), 3.90 (s, 3H), 3.87 (s, 3H), 3.77 (s, 2H), 3.64 (s, 2H), 3.19 (s, 4H), 3.09 (s, 4H), 2.62 (s, 4H), 2.38 (s, 3H), 2.15 (s, 3H);

Mass (M+H⁺) calcd for $C_{29}H_{37}FN_8O_3$ 564.65. found 564.83.

Example 31

Preparation of 4-(4-(2-(4-(4-acetylpiperazin-1-yl)-2-methoxyphenylamino)-5-fluoropyrimidin-4-ylamino)-3-methoxyphenyl)-N-ethylpiperazin-1-carboxyamide

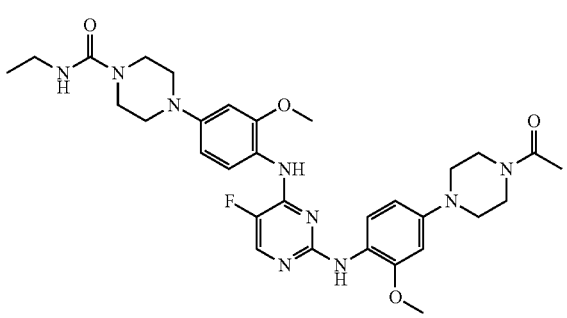 [SMILES: CCNC(=O)N1CCN(c2ccc(Nc3nc(Nc4ccc(N5CCN(C(C)=O)CC5)cc4OC)ncc3F)c(OC)c2)CC1]

A target compound was obtained in the same manner as in Example 13 except that ethyl isocyanate was used instead of methane sulfonylchloride.

¹H NMR (300 MHz, CD₃OD) δ 8.29 (d, J=8.6 Hz, 1H), 8.13 (d, J=8.6 Hz, 1H), 7.89 (s, 1H), 7.22 (s, 1H), 7.16 (s, 1H), 6.55 (s, 2H), 6.53 (s, 1H), 6.50 (s, 1H), 4.63 (br, 1H), 3.90 (s, 3H), 3.87 (s, 3H), 3.80 (t, J=4.1 Hz, 2H), 3.66 (t, J=4.4 Hz, 2H), 3.55 (t, J=4.1 Hz, 4H), 3.30 (q, J=7.2 Hz, 2H), 3.13 (t, J=4.4 Hz, 8H), 2.15 (s, 3H), 3.30 (t, J=7.2 Hz, 3H);

Mass (M+H⁺) calcd for $C_{31}H_{40}FN_9O_4$ 621.71. found 622.00.

Example 32

Preparation of tert-butyl-4-(4-(2-(4-(4-acetylpiper-azin-1-yl)-2-methoxyphenylamino)-5-fluoropyrimi-din-4-ylamino)-3-methoxyphenyl)piperazin-1-carboxylate

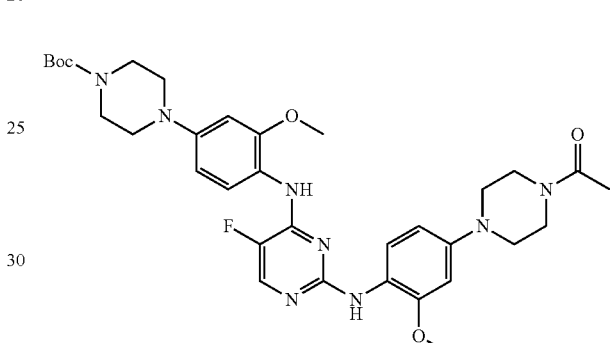

A target compound was obtained in the same manner as in Step 1 of Example 25.

¹H NMR (300 MHz, CD₃OD) δ 8.32 (d, J=8.7 Hz, 1H), 8.19 (d, J=8.7 Hz, 1H), 7.90 (s, 1H), 7.22 (s, 1H), 6.55 (d, J=6.4 Hz, 1H), 3.90 (s, 3H), 3.88 (m, 3H), 3.79 (s, 2H), 3.61 (s, 6H), 3.11 (s, 8H), 2.15 (s, 3H), 1.49 (s, 9H);

Mass (M+H⁺) calcd for $C_{33}H_{43}FN_8O_5$ 650.74. found 651.02.

Example 33

Preparation of 1-(4-(4-(5-chloro-4-(2-(difluo-romethoxy)-4-(piperazin-1-yl)phenylamino)pyrimi-din-2-ylamino)-3-methoxyphenyl)piperazin-1-yl)ethanone

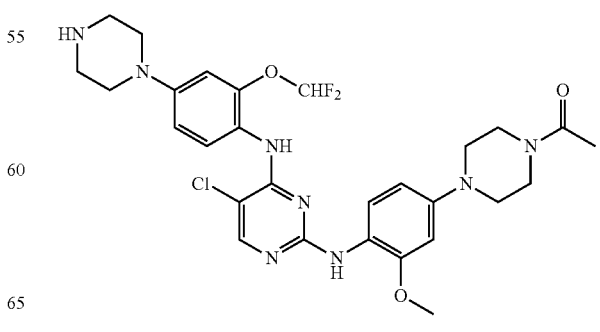

A target compound was obtained in the same manner as in Example 1 except that the compound prepared in Preparation Example 21 was used as a starting material instead of the compound prepared in Preparation Example 15.

$^1$H-NMR (300 MHz, DMSO-d$_6$) δ 8.85 (br, 2H), 8.13 (s, 1H), 7.42 (d, J=8.8 Hz, 1H), 7.29 (d, J=8.8 Hz, 1H), 7.01 (t, J=74 Hz, 1H), 6.90 (m, 2H), 6.64 (d, J=2.4 Hz, 1H), 6.32 (br, 1H), 3.77 (s, 3H), 3.58 (m, 4H), 3.41 (m, 4H), 3.26 (m, 4H), 3.15 (m, 2H), 3.08 (m, 2H), 2.05 (s, 3H);

Mass (M+H$^+$) calcd for $C_{28}H_{33}ClF_2N_8O_3$ 602.23. found 602.89.

Example 34

Preparation of tert-butyl 4-(4-(2-(4-(4-acetylpiperazin-1-yl)-2-methoxyphenylamino)-5-chloropyrimidin-4-ylamino)-3-(difluoromethoxy)phenyl)piperazin-1-carboxylate

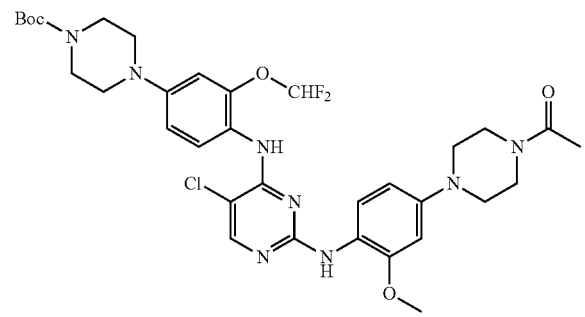 [SMILES: COc1cc(N2CCN(C(C)=O)CC2)ccc1Nc1ncc(Cl)c(Nc2ccc(N3CCN(C(=O)OC(C)(C)C)CC3)cc2OC(F)F)n1]

The compound prepared in Example 33 was dissolved in methylenechloride, added with Di-tert-butyl dicarbonate, and stirred at room temperature for 1 hour. Then, the mixture was concentrated under reduced pressure and purified by column chromatography (silica gel) to obtain a target compound.

$^1$H-NMR (300 MHz, CDCl$_3$) δ 8.21 (d, J=8.8 Hz, 1H), 8.08 (d, J=8.8 Hz, 1H), 805 (s, 1H), 7.29 (s, 1H), 6.81 (d, 8.8 Hz, 1H), 6.77 (s, 1H), 6.53 (s, 1H), 6.50 (t, J=74 Hz, 1H), 6.45 (d, J=8.8 Hz, 1H), 3.88 (s, 3H), 3.79 (m, 2H), 3.60 (m, 6H), 3.30 (m, 8H), 2.16 (s, 3H), 1.26 (s, 9H);

Mass (M+H$^+$) calcd for $C_{33}H_{41}ClF_2N_8O_5$ 702.29. found 702.94.

Example 35

Preparation of 1-(4-(4-(4-(4-(4-acetylpiperazin-1-yl)-2-(difluoromethoxy)phenylamino)-5-chloropyrimidin-2-ylamino)-3-methoxyphenyl)piperazin-1-yl)ethanone

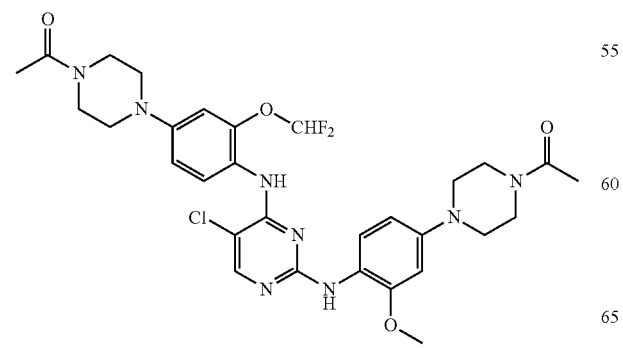

A target compound was obtained in the same manner as in Example 34 except that acetic anhydride was used instead of Di-tert-butyl dicarbonate.

$^1$H-NMR (300 MHz, DMSO-d$_6$) δ 8.34 (s, 1H), 7.99 (s, 1H), 7.64 (s, 1H), 7.40 (m, 2H), 6.94 (t, J=74 Hz, 1H), 6.83 (m, 2H), 6.60 (d, J=2.4 Hz, 1H), 6.23 (m, 1H), 3.74 (s, 3H), 3.57 (m, 4H), 3.17 (m, 4H), 3.04 (m, 4H), 2.07 (s, 3H), 2.05 (s, 3H);

Mass (M+H$^+$) calcd for $C_{30}H_{35}ClF_2N_8O_4$ 644.24. found 644.95.

Example 36

Preparation of 1-(4-(4-(2-(4-(4-acetylpiperazin-1-yl)-2-methoxyphenylamino)-5-fluoropyrimidin-4-ylamino)-3-methoxyphenyl)piperazin-1-yl)-2-hydroxyethanone

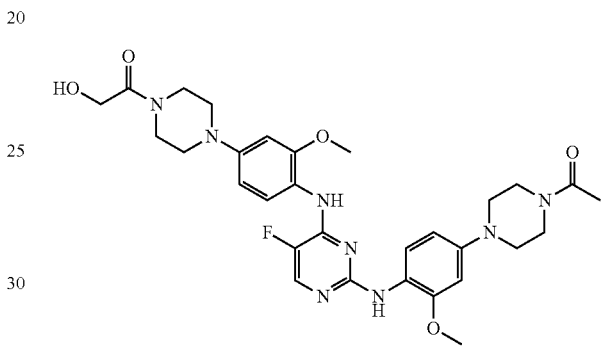

A target compound as a white solid was obtained in the same manner as in Example 14 except that the compound prepared in Example 25 was used as a starting material instead of the compound prepared in Example 12.

$^1$H NMR (300 MHz, CDCl$_3$) δ 8.35 (d, J=8.8 Hz, 1H), 8.18 (d, J=8.8 Hz, 1H), 7.90 (s, 1H), 7.22 (s, 1H), 6.55-6.50 (m, 4H), 4.23 (s, 2H), 3.91 (s, 36H), 3.88 (s, 3H), 3.85 (s, 2H), 3.79 (s, 2H), 3.63 (s, 2H), 3.46 (s, 2H), 3.17-3.10 (m, 8H), 2.15 (s, 3H);

Mass (M+H$^+$) calcd for $C_{30}H_{37}FN_8O_5$ 608.66. found 608.83.

Example 37

Preparation of 1-(4-(4-(4-(2-(difluoromethoxy)-4-(piperazin-1-yl)phenylamino)-5-fluoropyrimidin-2-ylamino)-3-methoxyphenyl)piperazin-1-yl)ethanone

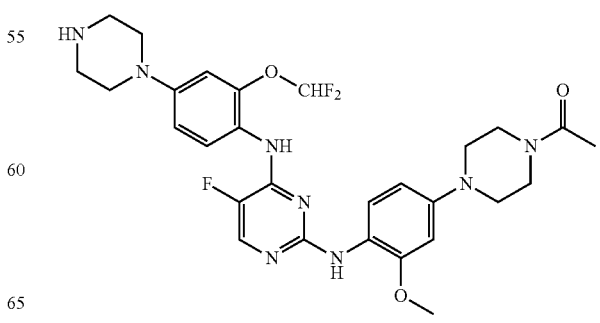

Step 1: Preparation of tert-butyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate A target compound as a white solid was obtained in the same manner as in Example 1 except that the compound prepared in Preparation Example 28 was used as a starting material instead of the compound prepared in Preparation Example 15.

Step 2: Preparation of 1-(4-(4-(4-(2-(difluoromethoxy)-4-(piperazin-1-yl)phenylamino)-5-fluoropyrimidin-2-ylamino)-3-methoxyphenyl)piperazin-1-yl)ethanone A target compound as a white solid was obtained in the same manner as in Step 2 of Example 12 except that the compound prepared in Step 1 above was used as a starting material instead of the compound prepared in Step 1 of Example 12.

$^1$H NMR (300 MHz, CD$_3$OD) δ 7.83 (d, J=3.4 Hz, 1H), 7.66 (d, J=8.8 Hz, 1H), 7.33 (d, J=8.0 Hz, 1H), 6.68 (s, 1H), 6.57 (d, J=8 Hz, 1H), 6.47 (s, 1H), 6.35 (s, 1H), 6.34 (t, J=74.6 Hz, 1H), 3.72 (s, 3H), 3.71-3.64 (m, 4H), 3.33-3.27 (m, 8H), 3.15-3.10 (m, 4H), 2.10 (s, 3H);

Mass (M+H$^+$) calcd for C$_{28}$H$_{33}$F$_3$N$_8$O$_5$ 587.27. found 587.15.

Example 38

Preparation of 1-(4-(4-(4-(2-(difluoromethoxy)-4-(4-methylpiperazin-1-yl)phenylamino)-5-fluoropyrimidin-2-ylamino)-3-methoxyphenyl)piperazin-1-yl)ethanone

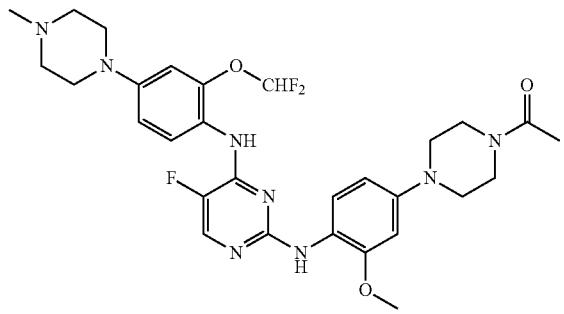 [SMILES: COc1cc(N2CCN(C(C)=O)CC2)ccc1Nc1ncc(F)c(Nc2ccc(N3CCN(C)CC3)cc2OC(F)F)n1]

A target compound (8.4 mg, 24%) was obtained in the same manner as in Example 13 except that the compound prepared in Example 37 was used as a starting material instead of the compound prepared in Example 12, and methyliodide was used instead of methanesulfonylchloride.

$^1$H NMR (300 MHz, CDCl$_3$) δ 8.18 (d, J=9.0 Hz, 1H), 8.11 (d, J=8.9 Hz, 1H), 7.93 (s, 1H), 7.21 (s, 1H), 6.89 (s, 1H), 6.81 (d, J=9.0 Hz, 1H), 6.74 (s, 1H), 6.53 (s, 1H), 6.50 (t, J=74.3 Hz, 1H), 6.46 (d, J=8.9 Hz, 1H), 3.87 (s, 3H), 3.78 (s, 2H), 3.62 (s, 2H), 3.21 (s, 4H), 3.09 (s, 4H), 2.60 (s, 4H), 2.38 (s, 3H), 2.15 (s, 3H);

Mass (M+H$^+$) calcd for C$_{29}$H$_{35}$F$_3$N$_8$O$_3$ 600.64. found 601.19.

Example 39

Preparation of tert-butyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate

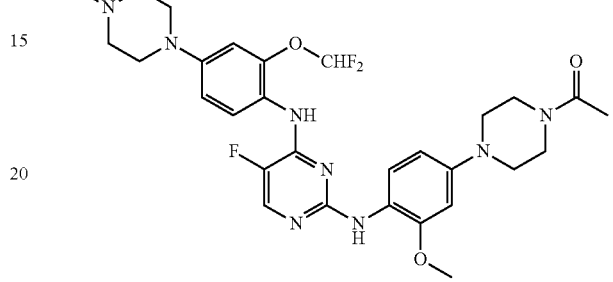

A target compound was obtained in the same manner as in Example 34 except that the compound prepared in Example 37 was used as a starting material instead of the compound prepared in Example 33.

$^1$H NMR (300 MHz, CDCl$_3$) δ 8.23 (d, J=9.1 Hz, 1H), 8.12 (d, J=8.7 Hz, 1H), 7.94 (s, 1H), 7.22 (s, 1H), 6.93 (s, 1H), 6.81 (d, J=9.1 Hz, 1H), 6.75 (s, 1H), 6.54 (s, 1H), 6.51 (t, J=73.5 Hz, 1H), 6.48 (d, J=8.7 Hz, 1H), 3.87 (s, 3H), 3.78 (s, 2H), 3.61 (s, 6H), 3.21 (s, 8H), 2.15 (s, 3H), 1.49 (s, 9H);

Mass (M+H$^+$) calcd for C$_{33}$H$_{41}$F$_3$N$_8$O$_3$ 686.72, fond 687.24.

Example 40

Preparation of 1-(4-(4-(4-(2-(difluoromethoxy)-4-(4-(methylsulfonyl)piperazin-1-yl)phenylamino)-5-fluoropyrimidin-2-ylamino)-3-methoxyphenyl)piperazin-1-yl)ethanone

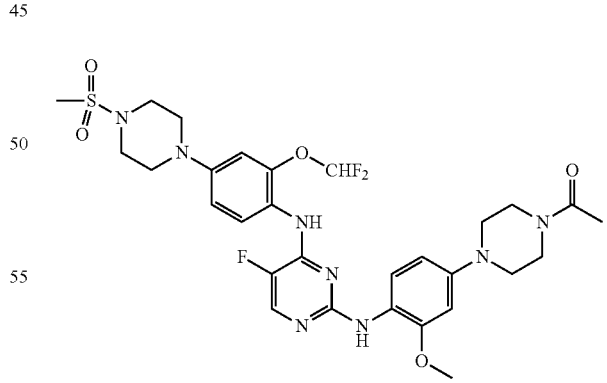

A target compound was obtained in the same manner as in Example 13 except that the compound prepared in Example 37 was used as a starting material instead of the compound prepared in Example 12.

$^1$H NMR (300 MHz, CDCl$_3$) δ 8.27 (d, J=8.9 Hz, 1H), 8.10 (d, J=8.7 Hz, 1H), 7.94 (s, 1H), 7.23 (s, 1H), 6.95 (s, 1H), 6.82 (d, J=8.9 Hz, 1H), 6.78 (s, 1H), 6.54 (s, 1H), 6.52 (t, J=75.6

Hz, 1H), 6.47 (d, J=8.7 Hz, 1H), 3.87 (s, 3H), 3.78 (s, 2H), 3.63 (s, 2H), 3.41 (s, 4H), 3.28 (s, 4H), 3.09 (s, 4H), 2.85 (s, 3H), 2.15 (s, 3H);

Mass (M+H$^+$) calcd for $C_{29}H_{35}F_3N_8O_5S$ 664.70, fond 665.24.

Example 41

Preparation of methyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate

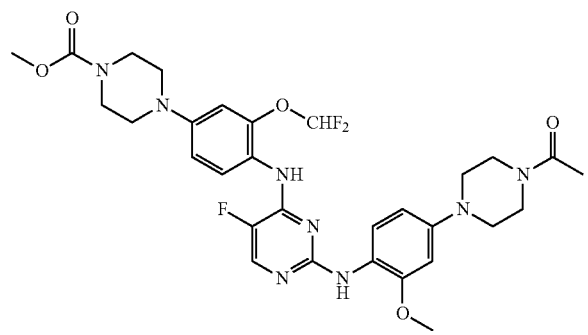 [SMILES: COC(=O)N1CCN(c2ccc(Nc3nc(Nc4ccc(N5CCN(C(C)=O)CC5)cc4OC)ncc3F)c(OC(F)F)c2)CC1]

A target compound was obtained in the same manner as in Example 13 except that the compound prepared in Example 37 was used as a starting material instead of the compound prepared in Example 12, and methyl carbonochloridate was used instead of methanesulfonylchloride.

$^1$H NMR (300 MHz, CDCl$_3$) δ 8.23 (d, J=8.9 Hz, 1H), 8.11 (d, J=8.7 Hz, 1H), 7.94 (s, 1H), 7.22 (s, 1H), 6.94 (s, 1H), 6.81 (d, J=8.9 Hz, 1H), 6.75 (s, 1H), 6.53 (s, 1H), 6.50 (t, J=75.6 Hz, 1H), 6.47 (d, J=8.7 Hz, 1H), 3.87 (s, 3H), 3.77 (s, 2H), 3.74 (s, 3H), 3.64-3.60 (m, 6H), 3.13-3.06 (m, 8H), 2.14 (s, 3H);

Mass (M+H$^+$) calcd for $C_{30}H_{35}F_3N_8O_5$ 644.64, fond 645.19.

Example 42

Preparation of 1-(4-(4-(4-(2-(difluoromethoxy)-4-(4-(2-hydroxyethyl)piperazin-1-yl)phenylamino)-5-fluoropyrimidin-2-ylamino)-3-methoxyphenyl)piperazin-1-yl)ethanone

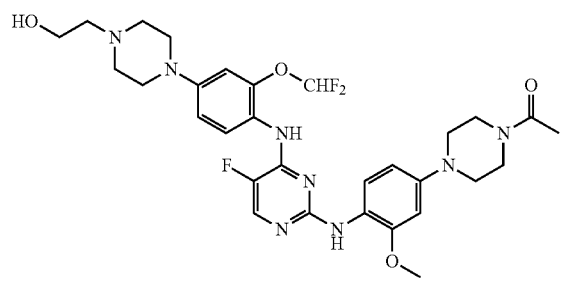 [SMILES: COc1cc(N2CCN(C(C)=O)CC2)ccc1Nc1ncc(F)c(Nc2ccc(N3CCN(CCO)CC3)cc2OC(F)F)n1]

A target compound was obtained in the same manner as in Example 16 except that the compound prepared in Example 37 was used as a starting material instead of the compound prepared in Example 12.

$^1$H NMR (300 MHz, CDCl$_3$) δ 8.19 (d, J=9.2 Hz, 1H), 8.10 (d, J=8.9 Hz, 1H), 7.93 (s, 1H), 7.21 (s, 1H), 6.89 (s, 1H), 6.81 (d, J=9.2 Hz, 1H), 6.75 (s, 1H), 6.53 (s, 1H), 6.50 (t, J=74.2 Hz, 1H), 6.47 (d, J=8.9 Hz, 1H), 3.87 (s, 3H), 3.77 (s, 2H), 3.71-3.66 (m, 2H), 3.63 (s, 2H), 3.22 (s, 4H), 3.09 (s, 4H), 2.71 (s, 4H), 2.66-2.63 (m, 2H), 2.15 (s, 3H);

Mass (M+H$^+$) calcd for $C_{30}H_{37}F_3N_8O_4$ 630.66, fond 631.22.

Example 43

Preparation of 4-(4-(2-(4-(4-acetylpiperazin-1-yl)-2-methoxyphenylamino)-5-fluoropyrimidin-4-ylamino)-3-(difluoromethoxy)phenyl)-N-ethylpiperazin-1-carboxyamide

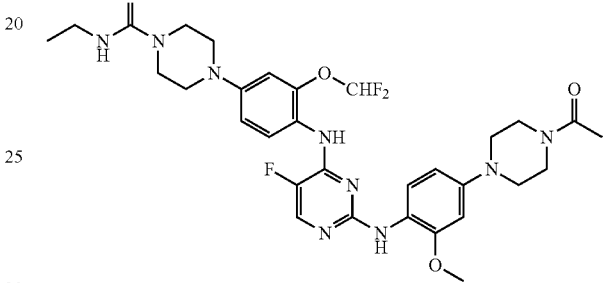

A target compound was obtained in the same manner as in Example 14 except that the compound prepared in Example 37 was used as a starting material instead of the compound prepared in Example 12, and ethylcarbamic acid was used instead of glycolic acid.

$^1$H NMR (300 MHz, CDCl$_3$) δ 8.20 (d, J=8.7 Hz, 1H), 8.05 (d, J=8.6 Hz, 1H), 7.94 (s, 1H), 7.18 (s, 1H), 6.93 (s, 1H), 6.78 (d, J=8.7 Hz, 1H), 6.75 (s, 1H), 6.54 (s, 1H), 6.50 (t, J=74.5 Hz, 1H), 6.46 (d, J=8.6 Hz, 1H), 4.68 (brs, 1H), 3.86 (s, 3H), 3.79 (s, 2H), 3.64 (m, 2H), 3.55 (s, 4H), 3.30 (q, J=6.7 Hz, 2H), 3.18-3.09 (m, 8H), 2.15 (s, 4H), 1.17 (t, J=6.7 Hz, 3H);

Mass (M+H$^+$) calcd for $C_{31}H_{38}F_3N_9O_4$ 657.69, fond 658.22.

Example 44

Preparation of 1-(4-(4-(2-(4-(4-acetylpiperazin-1-yl)-2-methoxyphenylamino)-5-fluoropyrimidin-4-ylamino)-3-(difluoromethoxy)phenyl)piperazin-1-yl)-2-hydroxyethanone

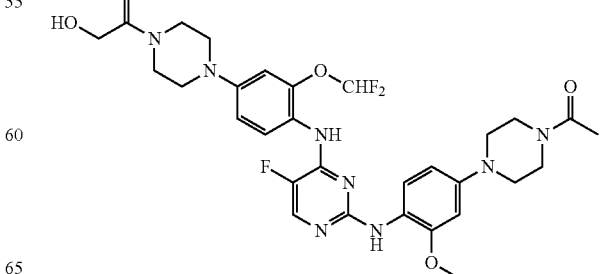

A target compound was obtained in the same manner as in Example 14 except that the compound prepared in Example 37 was used as a starting material instead of the compound prepared in Example 12.

¹H NMR (300 MHz, CDCl₃) δ 8.28 (d, J=9.0 Hz, 1H), 8.12 (d, J=8.6 Hz, 1H), 7.95 (s, 1H), 7.22 (s, 1H), 6.97 (s, 1H), 6.81 (d, J=9.0 Hz, 1H), 6.77 (s, 1H), 6.54 (s, 1H), 6.52 (t, J=73.4 Hz, 1H), 6.48 (d, J=8.6 Hz, 1H), 4.23 (s, 2H), 3.87 (s, 5H), 3.78 (s, 2H), 3.63 (m, 2H), 3.47 (s, 2H), 3.18 (s, 4H), 3.09 (s, 4H), 2.15 (s, 3H);

Mass (M+H⁺) calcd for $C_{30}H_{35}F_3N_8O_5$ 644.64, fond 645.19.

Example 45

Preparation of 1-(4-(4-(4-((4-((4-(4-acetylpiperazin-1-yl)-2-(difluoromethoxy)phenyl)amino)-5-fluoropyrimidin-2-yl)amino)-3-methoxyphenyl)piperazin-1-yl)ethanone

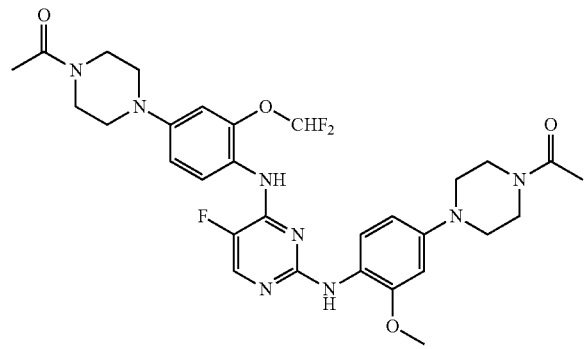 [SMILES: COc1cc(N2CCN(C(C)=O)CC2)ccc1Nc1ncc(F)c(Nc2ccc(N3CCN(C(C)=O)CC3)cc2OC(F)F)n1]

The compound (30 mg) of Example 37, acetic anhydride (7 μl), and triethylamine (11 μl) were dissolved in methylenechloride (1 ml) and stirred at room temperature overnight. Upon completion of the reaction, the solvent was removed by distillation under reduced pressure, and purified by prep. TLC to obtain a target compound (26.9 mg, 79%).

¹H NMR (300 MHz, CDCl₃) δ 8.25 (d, J=9.0 Hz, 1H), 8.11 (d, J=8.6 Hz, 1H), 7.94 (s, 1H), 7.24 (s, 1H), 6.96 (s, 1H), 6.81 (d, J=9.0 Hz, 1H), 6.76 (s, 1H), 6.54 (s, 1H), 6.52 (t, J=73.4 Hz, 1H), 6.47 (d, J=8.6 Hz, 1H), 3.87 (s, 3H), 3.79 (s, 4H), 3.63 (m, 4H), 3.16-3.09 (m, 8H), 2.15 (s, 6H);

Mass (M+H⁺) calcd for $C_{30}H_{35}F_3N_8O_4$ 628.65, fond 629.20.

Example 46

Preparation of 1-(4-(4-(4-(4-(4-acetylpiperazin-1-yl)-2-(tert-butylamino)phenylamino)-5-chloropyrimidin-2-ylamino)-3-methoxyphenyl)piperazin-1-yl)ethanone

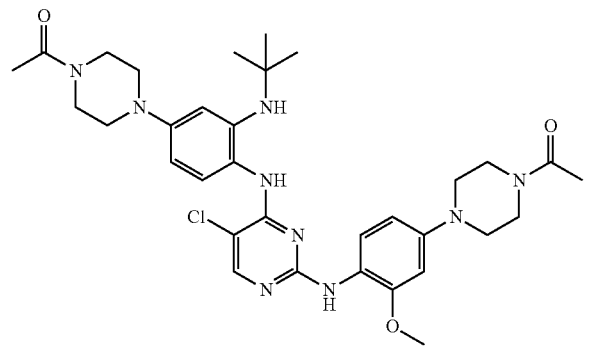 [SMILES: COc1cc(N2CCN(C(C)=O)CC2)ccc1Nc1ncc(Cl)c(Nc2ccc(N3CCN(C(C)=O)CC3)cc2NC(C)(C)C)n1]

A target compound was obtained in the same manner as in Example 1 except that the compound prepared in Preparation Example 24 was used as a starting material instead of the compound prepared in Preparation Example 15.

¹H NMR (300 MHz, CDCl₃) δ 7.92 (s, 1H), 7.72 (d, J=9.0 Hz, 1H), 7.33 (d, J=8.4 Hz, 1H), 6.76-6.70 (m, 1H), 6.63-6.54 (m, 2H), 6.32-6.24 (m, 1H), 3.84 (s, 3H), 3.79-3.47 (m, 11H), 3.25-3.17 (m, 4H), 3.12-3.00 (m, 4H), 2.15 (d, J=5.7 Hz, 6H);

Mass (M+H⁺) calcd for $C_{33}H_{44}ClN_9O_3$ 649.33, fond 650.08.

Example 47

Preparation of 1-(4-(4-(4-(4-(4-acetylpiperazin-1-yl)-2-(phenylamino)phenylamino)-5-chloropyrimidin-2-ylamino)-3-methoxyphenyl)piperazin-1-yl)ethanone

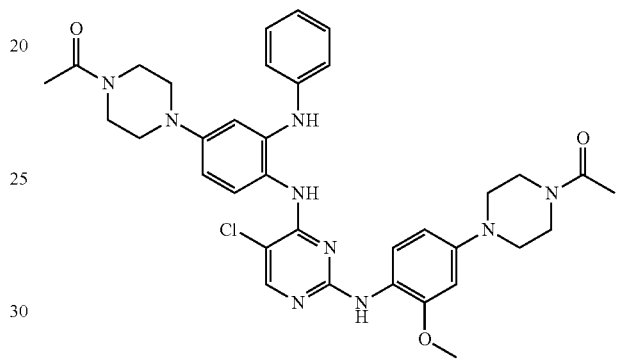

A target compound was obtained in the same manner as in Example 1 except that the compound prepared in Preparation Example 23 was used as a starting material instead of the compound prepared in Preparation Example 15.

¹H NMR (300 MHz, CDCl₃) δ 8.20 (d, J=9.6 Hz, 1H), 8.06-7.95 (m, 1H), 7.76-7.64 (m, 1H), 7.63-7.47 (m, 3H), 7.44-7.33 (m, 1H), 7.10-6.95 (m, 2H), 6.65-6.47 (m, 3H), 3.81 (s, 3H), 3.69-3.41 (m, 10H), 3.40-3.31 (m, 1H), 3.21-3.00 (m, 8H), 2.12 (d, J=9.0 Hz, 6H);

Mass (M+H⁺) calcd for $C_{35}H_{40}ClN_9O_3$ 669.29, fond 669.93.

Example 48

Preparation of N-(2-(2-(4-(4-acetylpiperazin-1-yl)-2-methoxyphenylamino)-5-chloropyrimidin-4-ylamino)-5-(piperazin-1-yl)phenyl)-N-methylpropionamide

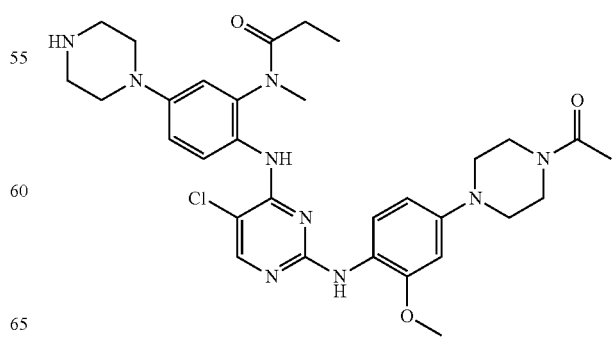

Step 1: Preparation of tert-butyl 4-(4-(2-(4-(4-acetylpiperazin-1-yl)-2-methoxyphenylamino)-5-chloropyrimidin-4-ylamino)-3-(N-methylpropionamido)phenyl)piperazin-1-carboxylate A target compound was obtained in the same manner as in Example 1 except that the compound prepared in Preparation Example 25 was used as a starting material instead of the compound prepared in Preparation Example 15.

Step 2: Preparation of N-(2-(2-(4-(4-acetylpiperazin-1-yl)-2-methoxyphenylamino)-5-chloropyrimidin-4-ylamino)-5-(piperazin-1-yl)phenyl)-N-methylpropionamide A target compound was obtained in the same manner as in Step 2 of Example 12 except that the compound prepared in Step 1 above was used as a starting material instead of the compound prepared in Step 1 of Example 12.

$^1$H NMR (300 MHz, CDCl$_3$) δ 7.91 (s, 1H), 7.51 (dd, J=9.3 Hz, 2H), 7.15-7.08 (m, 1H), 6.9 (s, 1H), 6.61 (s, 1H), 6.21 (dd, J=1.2, 9.0 Hz, 1H), 3.78-3.63 (m, 8H), 3.31 (s, 3H), 3.14-3.01 (m, 8H), 2.15 (s, 3H), 2.11-1.99 (m, 2H), 0.80 (t, J=7.2 Hz, 3H);

Mass (M+H$^+$) calcd for C$_{31}$H$_{40}$ClN$_9$O$_3$ 621.19, fond 622.11.

Example 49

Preparation of N-(2-(2-(4-(4-acetylpiperazin-1-yl)-2-methoxyphenylamino)-5-chloropyrimidin-4-ylamino)-5-(piperazin-1-yl)phenyl)-N-methylbutylamide

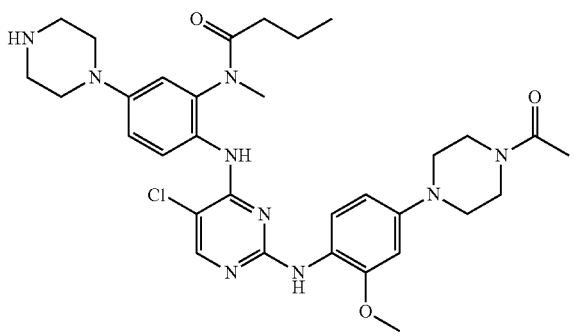 [SMILES: CCCC(=O)N(C)c1cc(N2CCNCC2)ccc1Nc1nc(Nc2ccc(N3CCN(C(C)=O)CC3)cc2OC)ncc1Cl]

Step 1: Preparation of tert-butyl 4-(4-(2-(4-(4-acetylpiperazin-1-yl)-2-methoxyphenylamino)-5-chloropyrimidin-4-ylamino)-3-(N-methylbutylamido)phenyl)piperazin-1-carboxylate A target compound was obtained in the same manner as in Example 1 except that the compound prepared in Preparation Example 26 was used as a starting material instead of the compound prepared in Preparation Example 15.

Step 2: Preparation of N-(2-(2-(4-(4-acetylpiperazin-1-yl)-2-methoxyphenylamino)-5-chloropyrimidin-4-ylamino)-5-(piperazin-1-yl)phenyl)-N-methylbutylamide A target compound was obtained in the same manner as in Step 2 of Example 12 except that the compound prepared in Step 1 above was used as a starting material instead of the compound prepared in Step 1 of Example 12.

$^1$H NMR (300 MHz, CDCl$_3$) δ 7.91 (s, 1H), 7.58 (d, J=8.7 Hz, 1H), 7.47 (d, J=8.7 Hz, 1H), 7.11 (d, J=8.7 Hz, 1H), 6.93 (s, 1H), 6.61 (s, 1H), 6.21 (d, J=8.7 Hz, 1H), 3.83 (s, 3H), 3.74-3.71 (m, 4H), 3.31 (s, 3H), 3.26-3.20 (m, 4H), 3.14-2.98 (m, 8H), 2.15)s, 3H), 2.08-1.96 (m, 2H), 1.42-1.82 (m, 2H), 0.58 (t, J=7.2 Hz, 3H);

Mass (M+H$^+$) calcd for C$_{31}$H$_{41}$ClN$_9$O$_3$ 635.31, fond 636.15.

Example 50

Preparation of tert-butyl 4-(4-(2-(4-(4-acetylpiperazin-1-yl)-2-methoxyphenylamino)-5-chloropyrimidin-4-ylamino)-3-(N-methylpropionamido)phenyl)piperazin-1-carboxylate

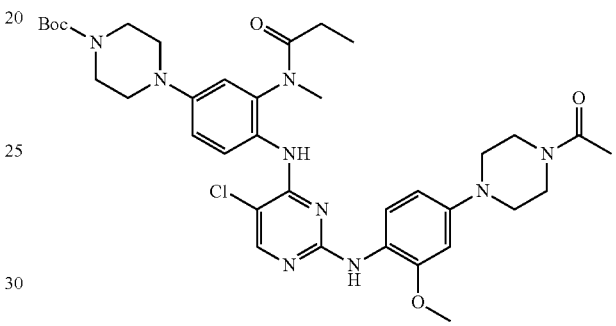

A target compound was obtained in the same manner as in Example 34 except that the compound prepared in Example 48 was used as a starting material instead of the compound prepared in Example 33.

$^1$H NMR (300 MHz, CDCl$_3$) δ 8.32 (d, J=8.7 Hz, 1H), 8.14-8.02 (m, 2H), 7.04 (s, 1H), 6.98 (d, J=8.1 Hz, 1H), 6.40-6.70 (m, 1H), 6.59-6.43 (m, 1H), 3.89 (s, 3H), 3.71-3.48 (m, 8H), 3.23 (s, 3H), 3.14-3.03 (m, 8H), 2.16 (s, 3H), 1.50 (s, 9H), 1.04 (t, J=6.9 Hz, 3H);

Mass (M+H$^+$) calcd for C$_{36}$H$_{48}$ClN$_9$O$_5$ 721.35, fond 722.34.

Example 51

Preparation of tert-butyl 4-(4-(2-(4-(4-acetylpiperazin-1-yl)-2-methoxyphenylamino)-5-chloropyrimidin-4-ylamino)-3-(N-methylbutylamido)phenyl)piperazin-1-carboxylate

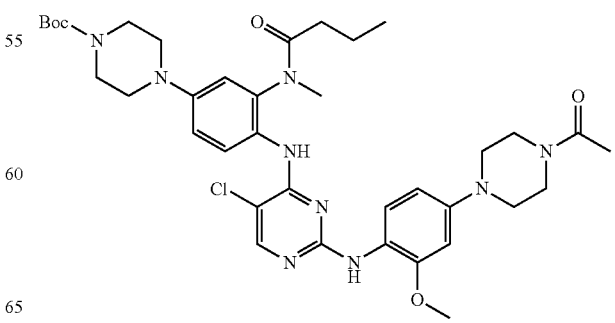

A target compound was obtained in the same manner as in Example 34 except that the compound prepared in Example 49 was used as a starting material instead of the compound prepared in Example 33.

$^1$H NMR (300 MHz, CDCl$_3$) δ 8.32 (d, J=9.0 Hz, 1H), 8.11 (d, J=8.7 Hz, 1H), 8.04 (s, 1H), 6.99-6.93 (m, 1H), 6.76-6.69 (m, 1H), 6.55 (m, 1H), 6.50 (d, J=8.7 Hz, 1H), 3.89 (s, 3H), 3.763-3.52 (m, 8H), 3.22 (s, 3H), 3.14-3.13 (m, 8H), 2.16 (s, 3H), 1.61-1.53 (m, 2H), 1.50 (s, 9H), 1.28-1.20 (m, 2H), 0.80 (t, J=7.2 Hz, 3H);

Mass (M+H$^+$) calcd for C$_{37}$H$_{450}$ClN$_9$O$_5$ 735.36, fond 736.38.

Example 52

Preparation of tert-butyl 4-(4-(4-(4-(4-acetylpiperazin-1-yl)-2-methoxyphenylamino)-5-chloropyrimidin-2-ylamino)-3-methoxyphenyl)piperazin-1-carboxylate

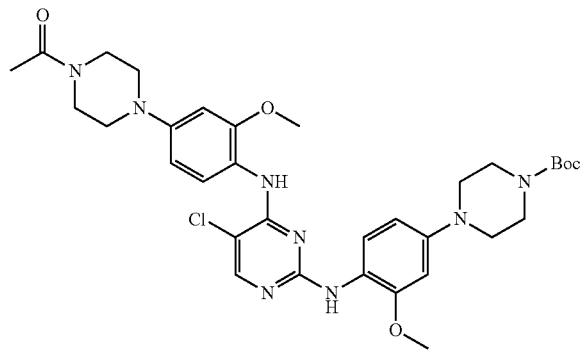 [SMILES: COc1cc(N2CCN(C(=O)OC(C)(C)C)CC2)ccc1Nc1ncc(Cl)c(Nc2ccc(N3CCN(C(C)=O)CC3)cc2OC)n1]

A target compound was obtained in the same manner as in Example 1 except that the compound prepared in Preparation Example 14 was used as a starting material instead of the compound prepared in Preparation Example 15, and the compound prepared in Preparation Example 34 was used instead of the compound prepared in Preparation Example 1.

$^1$H-NMR (300 MHz, CDCl$_6$) δ 8.28 (d, J=8.6 Hz, 1H), 8.12 (d, J=8.6 Hz, 1H), 8.00 (s, 1H), 7.57 (s, 1H), 7.23 (s, 1H), 6.52 (m, 4H), 3.91 (s, 3H), 3.87 (s, 3H), 3.80 (m, 2H), 3.65 (m, 2H), 3.59 (m, 4H), 3.14 (m, 4H), 3.07 (m, 4H), 2.16 (s, 3H), 1.48 (s, 9H);

Mass (M+H$^+$) calcd for C$_{33}$H$_{43}$ClN$_8$O$_5$ 666.30. found 667.19.

Example 53

Preparation of N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylpropionamide

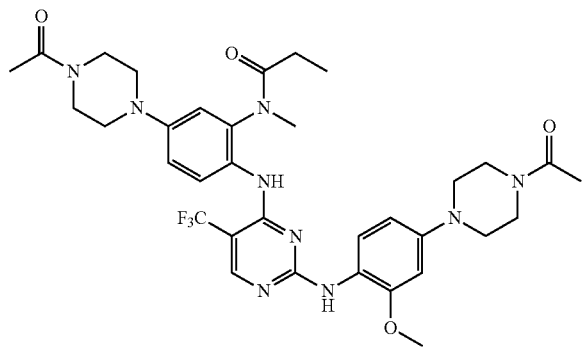 [SMILES: CCC(=O)N(C)c1cc(N2CCN(C(C)=O)CC2)ccc1Nc1nc(Nc2ccc(N3CCN(C(C)=O)CC3)cc2OC)ncc1C(F)(F)F]

A target compound was obtained in the same manner as in Example 45 except that the compound prepared in Example 48 was used as a starting material instead of the compound prepared in Example 37.

$^1$H-NMR (500 MHz, CDCl$_6$) δ 8.35 (d, J=8.5 Hz, 1H), 8.09 (d, J=8.5 Hz, 1H), 8.05 (s, 1H), 7.06 (s, 1H), 6.97 (ddd, J=0.5, 2.0, 9.5 Hz, 1H), 6.73 (d, J=2.0 Hz, 1H), 6.54 (d, J=1.5 Hz, 1H), 6.48 (dd, J=1.5, 8.5 Hz, 1H), 3.89 (s, 3H), 3.80-3.75 (m, 4H), 3.68-3.62 (m, 4H), 3.23 (s, 3H), 3.20-3.00 (m, 2H), 2.17 (s, 3H), 2.16 (s, 3H), 2.10-2.00 (m, 2H), 1.10-1.00 (m, 3H).

Example 54

Preparation of N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylbutylamide

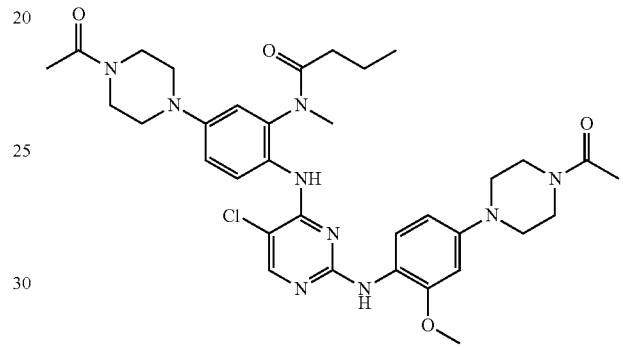

A target compound was obtained in the same manner as in Example 45 except that the compound prepared in Example 49 was used as a starting material instead of the compound prepared in Example 37.

$^1$H-NMR (500 MHz, CDCl$_6$) δ 8.35 (d, J=8.5 Hz, 1H), 8.09 (d, J=8.5 Hz, 1H), 8.05 (s, 1H), 7.06 (s, 1H), 6.97 (ddd, J=0.5, 2.0, 9.5 Hz, 1H), 6.73 (d, J=2.0 Hz, 1H), 6.54 (d, J=1.5 Hz, 1H), 6.48 (dd, J=1.5, 8.5 Hz, 1H), 3.89 (s, 3H), 3.80-3.75 (m, 4H), 3.68-3.62 (m, 4H), 3.23 (s, 3H), 3.20-3.00 (m, 2H), 2.17 (s, 3H), 2.16 (s, 3H), 2.10-2.00 (m, 2H), 1.70-1.45 (m, 2H), 0.90-0.75 (m, 3H).

Example 55

Preparation of tert-butyl 4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-carboxylate

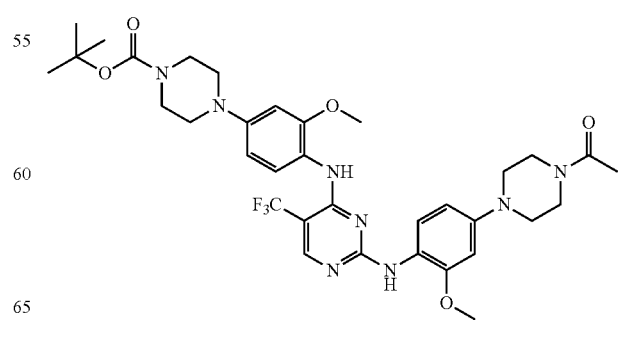

The compound (928 mg) prepared in Preparation Example 29 and the compound (474 mg) prepared in Preparation Example 1 were dissolved in 0.08M HCl (19 ml, in ethoxyethanol solution), and stirred at 50° C. overnight. Upon completion of the reaction, the solvent was removed by distillation under reduced pressure, and dissolved in ethyl acetate. The mixture was neutralized with a saturated aqueous solution of sodium bicarbonate, subjected to a layer separation, and washed with saturated brine. The washed mixture was dried with sodium sulfate, distilled under reduced pressure to remove the solvent. The concentrated mixture formed crystals using ether, and filtered to obtain a target compound (1.07 mg, 80%).

$^1$H-NMR (300 MHz, CD$_3$OD) δ 8.25 (s, 1H), 8.12 (d, J=8.6 Hz, 2H), 7.43 (s, 1H), 7.37 (s, 1H), 6.54 (s, 2H), 6.53 (s, 1H), 6.45 (d, J=8.6 Hz, 1H), 3.88 (s, 6H), 3.79 (s, 2H), 3.66-3.65 (m, 6H), 3.14-3.08 (m, 8H), 2.15 (s, 3H), 1.45 (s, 9H);

Mass (M+H$^+$) calcd for C$_{34}$H$_{43}$F$_3$N$_8$O$_5$ 700.5. found 701.28.

Example 56

Preparation of 1-(4-(3-methoxy-4-((4-((2-methoxy-4-(piperazin-1-yl)phenyl)amino)-5-(trifluoromethyl)pyrimidin-2-yl)amino)phenyl)piperazin-1-yl)ethanone

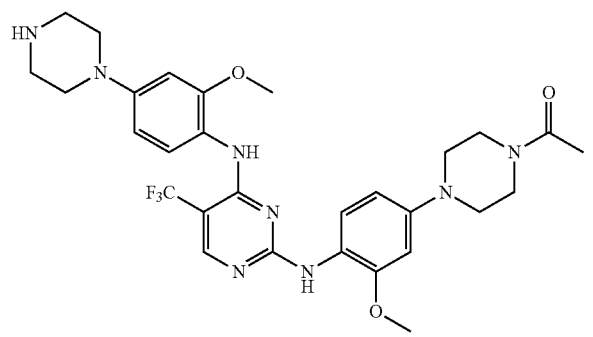 [SMILES: COc1cc(N2CCN(C(C)=O)CC2)ccc1Nc1ncc(C(F)(F)F)c(Nc2ccc(N3CCNCC3)cc2OC)n1]

The compound (1.07 g) prepared in Example 55 was dissolved in methylenechloride (10 ml), added with 4M HCl (dioxane solution, 2 ml), and stirred at room temperature overnight. Then, the resultant was distilled under reduced pressure to remove the solvent and diluted again with methylenechloride. The resultant was neutralized with a saturated aqueous solution of sodium bicarbonate and subjected to a layer separation. The separated organic layer was washed with saturated brine and dried with sodium sulfate. Then, the organic layer was distilled under reduced pressure to remove the solvent and a target compound (721.4 mg, 77%) was obtained without further purification.

$^1$H-NMR (300 MHz, CD$_3$OD) δ 8.23 (s, 1H), 8.10-8.04 (m, 2H), 7.45 (s, 1H), 7.33 (s, 1H), 6.53-6.41 (m, 4H), 3.85 (s, 6H), 3.77 (s, 2H), 3.61 (s, 2H), 3.13-3.07 (m, 12H), 2.13 (s, 3H);

Mass (M+H$^+$) calcd for C$_{29}$H$_{35}$F$_3$N$_8$O$_3$ 600.64. found 601.19.

Example 57

Preparation of 4-(4-(((2-((4-(4-acetylpiperazine)-2-methoxyphenyl)amino)-5-(trifluoromethyl)pyrimidin-4-yl)amino)-3-methoxyphenyl)-N-ethylpiperazin-1-carboxyamide

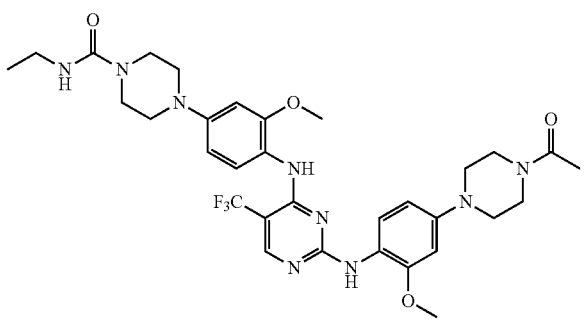 [SMILES: CCNC(=O)N1CCN(c2ccc(Nc3nc(Nc4ccc(N5CCN(C(C)=O)CC5)cc4OC)ncc3C(F)(F)F)c(OC)c2)CC1]

A target compound (26 mg, 77%) was obtained in the same manner as in Example 13 except that the compound prepared in Example 56 was used as a starting material instead of the compound prepared in Example 12, and ethyl isocyanate was used instead of methanesulfonylchloride.

$^1$H-NMR (300 MHz, CD$_3$OD) δ 8.25 (s, 1H), 8.07 (d, J=8.4 Hz, H), 8.01 (d, J=8.4 HZ, 1H), 7.42 (s, 1H), 7.38 (s, 1H), 6.53 (s, 2H), 6.45 (d, J=8.4 Hz, 2H), 4.86 (br, 1H), 3.87 (s, 3H), 3.85 (s, 3H), 3.79 (s, 2H), 3.65 (s, 2H), 3.56 (s, 4 h), 3.31 (dd, J=6.2, 12.2 Hz, 2H), 3.14 (s, 4H), 2.15 (s, 3H), 1.18 (t, J=6.2 Hz, 3H));

Mass (M+H$^+$) calcd for C$_{32}$H$_{40}$F$_3$N$_9$O$_4$ 671.71. found 672.258.

Example 58

Preparation of 1-(4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-yl)-2-hydroxyethanone

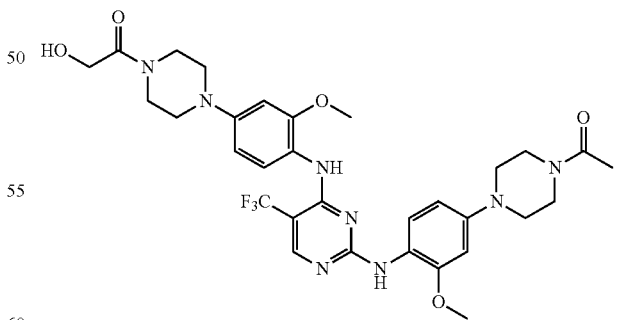

A target compound (23.9 mg, 72%) was obtained in the same manner as in Example 14 except that the compound prepared in Example 56 was used as a starting material instead of the compound prepared in Example 12.

$^1$H-NMR (300 MHz, CD$_3$OD) δ 8.26 (s, 1H), 8.15-8.08 (m, 2H), 7.45 (s, 1H), 7.41 (s, 1H), 6.53-6.43 (m, 4H), 4.23 (s,

2H), 3.87 (s, 8H), 3.78 (s, 2H), 3.64 (s, 2H), 3.47 (s, 2H), 3.17 (s, 4H), 3.12 (s, 4H), 2.15 (s, 3H);

Mass (M+H⁺) calcd for $C_{31}H_{37}F_3N_8O_5$ 658.67. found 659.23.

Example 59

Preparation of 1-(4-(3-methoxy-4-((4-((2-methoxy-4-(4-methylpiperazin-1-yl)phenyl)amino)-5-trifluoromethyl)pyrimidin-2-yl)amino)phenyl)piperazin-1-yl)ethanone

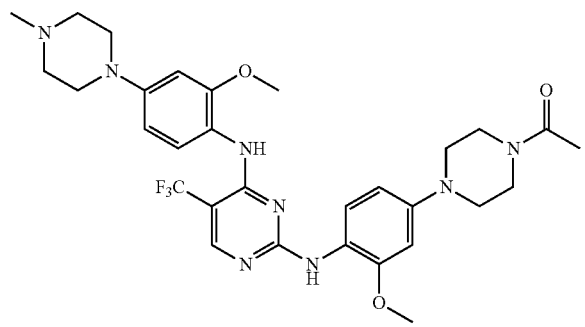 [SMILES: COc1cc(N2CCN(C(C)=O)CC2)ccc1Nc1ncc(C(F)(F)F)c(Nc2ccc(N3CCN(C)CC3)cc2OC)n1]

A target compound (7.4 mg, 24%) was obtained in the same manner as in Example 13 except that the compound prepared in Example 56 was used as a starting material instead of the compound prepared in Example 12, and reacted overnight using methyliodide instead of methanesulfonylchloride.

¹H-NMR (300 MHz, CD₃OD) δ 8.24 (s, 1H), 8.10 (d, J=8.4 Hz, 1H), 7.44 (s, 1H), 7.33 (s, 1H), 6.55-6.51 (m, 3H), 6.44 (d, J=8.4 Hz, 1H), 3.87 (s, 6H), 3.79 (s, 2H), 3.63 (s, 2H), 3.22 (s, 4H), 3.11 (s, 4H), 2.62 (s, 4H), 2.38 (s, 3H), 2.15 (s, 3H);

Mass (M+H⁺) calcd for $C_{30}H_{37}F_3N_8O_3$ 614.66. found 615.23.

Example 60

Preparation of N1-(4-(3-methoxy-4-((4-((2-methoxy-4-(4-methylsulfonyl)piperazin-1-yl)phenyl)amino)-5-(trifluoromethyl)pyrimidin-2-yl)amino)phenyl)piperazin-1-yl)ethanone

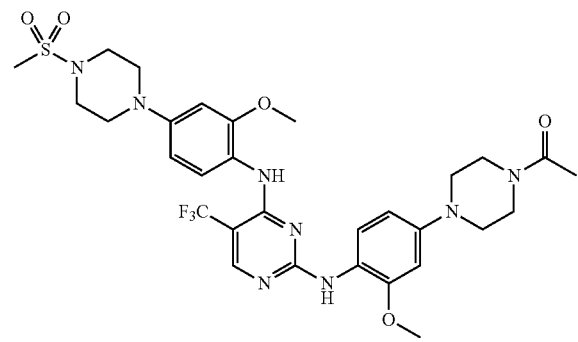 [SMILES: COc1cc(N2CCN(C(C)=O)CC2)ccc1Nc1ncc(C(F)(F)F)c(Nc2ccc(N3CCN(S(C)(=O)=O)CC3)cc2OC)n1]

A target compound (12.4 mg, 36%) was obtained in the same manner as in Example 13 except that the compound prepared in Example 56 was used as a starting material instead of the compound prepared in Example 12.

¹H-NMR (300 MHz, CD₃OD) δ 8.26 (s, 1H), 8.13 (d, J=7.5 Hz, 1H), 8.08 (d, J=8.5 Hz, 1H), 7.45 (s, 1H), 7.38 (s, 1H), 6.54 (d, J=7.5 Hz, 3H), 6.43 (d, J=8.5 Hz, 1H), 3.88 (s, 6H), 3.78 (s, 6H), 3.64 (s, 2H), 3.42 (s, 4H), 3.28 (s, 4H), 3.12 (s, 4H), 2.86 (s, 3H), 2.15 (s, 3H);

Mass (M+H⁺) calcd for $C_{30}H_{37}F_3N_8O_5S$ 678.73. found 679.14.

Example 61

Preparation of 1-(4-(4-((4-((4-(4-(2-hydroxyethyl)piperazin-1-yl)-2-methoxyphenyl)amino)-5-(trifluoromethyl)pyrimidin-2-yl)amino)-3-methoxyphenyl)piperazin-1-yl)ethanone

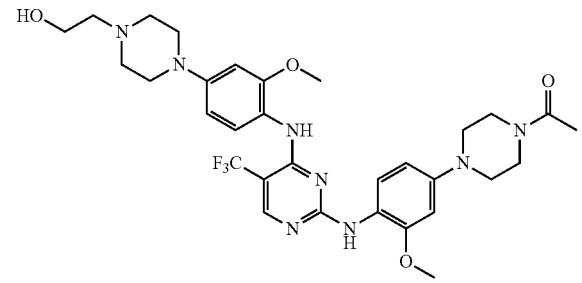

A target compound (18.2 mg, 56%) was obtained in the same manner as in Example 16 except that the compound prepared in Example 56 was used as a starting material instead of the compound prepared in Example 12.

¹H-NMR (300 MHz, CD₃OD) δ 8.24 (s, 1H), 8.08 (d, J=8.5 Hz, 2H), 7.44 (s, 1H), 7.33 (s, 1H), 6.54-6.50 (m, 3H), 6.43 (d, J=8.5 Hz, 1H), 3.87 (s, 6H), 3.79 (s, 2H), 3.69 (s, 2H), 3.63 (s, 2H), 3.22 (s, 4H), 3.11 (s, 4H), 2.72 (s, 4H), 2.64 (s, 2H), 2.15 (s, 3H);

Mass (M+H⁺) calcd for $C_{31}H_{39}F_3N_8O_4$ 644.69. found 645.12.

Example 62

Preparation of tert-butyl-4-(4-((4-((4-(4-acetylpiperazin-1-yl)-2-methoxyphenyl)amino)-5-(trifluoromethyl)pyrimidin-2-yl)amino)-3-methoxyphenyl)piperazin-1-carboxylate

The compound (337 mg) prepared in Preparation Example 30 and the compound (172 mg) prepared in Preparation Example 1 were dissolved in 0.08M HCl (ethoxyethanol, 7 ml), and stirred overnight at 50° C. Upon completion of the reaction, the mixture was distilled under reduced pressure to remove the solvent and dissolved in ethyl acetate. The mixture dissolved in the organic solvent was neutralized with a saturated aqueous solution of sodium bicarbonate, subjected to a layer separation of the organic layer, and the organic layer was washed with brine. The organic layer was dried with sodium sulfate, distilled under reduced pressure to remove the solvent. The concentrated mixture was added with ether to form crystals, and the thus formed crystals were filtered to obtain a target compound (412 mg, 85%).

$^1$H-NMR (300 MHz, CD$_3$OD) δ 8.26 (s, 1H), 8.17-8.07 (m, 2H), 7.41 (s, 2H), 6.54-6.44 (m, 4H), 3.89 (s, 3H), 3.87 (s, 3H), 3.80 (s, 2H), 3.73 (s, 2H), 3.67 (s, 2H), 3.60-3.56 (m, 2H), 3.16-3.08 (m, 8H), 2.16 (s, 3H), 1.49 (s, 9H);

Mass (M+H$^+$) calcd for C$_{34}$H$_{43}$F$_3$N$_8$O$_5$ 700.75. found 701.28.

Example 63

Preparation of 1-(4-(3-methoxy-4-((2-((2-methoxy-4-(piperazin-1-yl)phenyl)amino)-5-(trifluoromethyl)pyrimidin-4-yl)amino)phenyl)piperazin-1-yl)ethanone

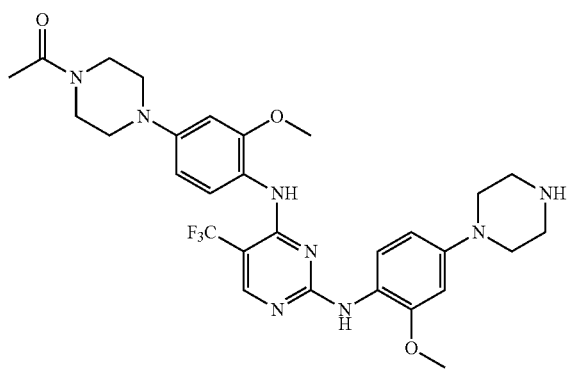 [SMILES: COc1cc(N2CCNCC2)ccc1Nc1ncc(C(F)(F)F)c(Nc2ccc(N3CCN(C(C)=O)CC3)cc2OC)n1]

The compound (410 mg) prepared in Example 62 was dissolved in methylenechloride (10 ml), added with 4M HCl (dioxane solution, 1.5 ml), and stirred at room temperature overnight. Upon completion of the reaction, the mixture was distilled under reduced pressure to remove the solvent, and diluted in methylenechloride. The mixture was neutralized with a saturated aqueous solution of sodium bicarbonate, subjected to separation of the organic layer, and washed with saturated brine. Then, the washed organic layer was dried with sodium sulfate, distilled under reduced pressure to remove the solvent and a target compound (322.1 mg, 55%) was obtained without further purification.

$^1$H-NMR (300 MHz, CD$_3$OD) δ 8.26 (s, 1H), 8.09 (s, 1H), 7.70 (s, 1H), 7.54 (s, 1H), 7.37 (s, 1H), 6.55-6.43 (m, 4H), 3.88 (s, 3H), 3.87 (s, 3H), 3.80-3.75 (m, 6H), 3.67-3.63 (m, 6H), 3.17 (s, 4H), 2.17 (s, 3H);

Mass (M+H1 calcd for C$_{29}$H$_{35}$F$_3$N$_8$O$_3$ 600.64. found 601.19.

Example 64

Preparation of 4-(4-((4-((4-(4-acetylpiperazin-1-yl)-2-methoxyphenyl)amino)-5-(trifluoromethyl)pyrimidin-2-yl)amino)-3-methoxyphenyl)-N-ethylpiperazin-1-carboxyamide

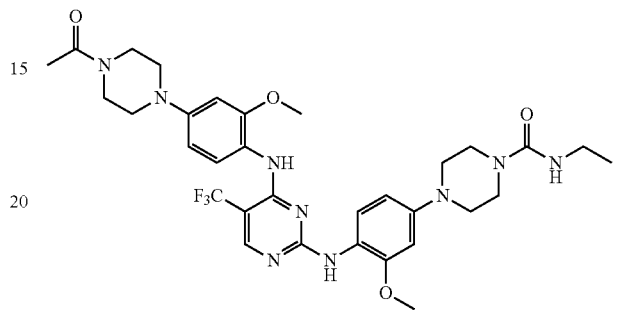

A target compound (26 mg, 77%) was obtained in the same manner as in Example 13 except that the compound prepared in Example 63 was used as a starting material instead of the compound prepared in Example 12, and ethyl isocyanate was used instead of methylsulfonyl chloride.

$^1$H NMR (300 MHz, CD$_3$OD) δ 8.25 (s, 1H), 8.01 (d, J=8.0 Hz, 2H), 7.47 (s, 1H), 6.56 (s, 1H), 6.52 (s, 2H), 6.35 (d, J=8.0 Hz, 1H), 4.91 (brs, 1H) 3.86 (s, 3H), 3.82 (s, 3H), 3.67 (s, 2H), 3.54 (s, 4H), 3.31 (p, J=6.2, 12.2 Hz, 2H), 3.18 (s, 4H), 3.09 (s, 4H), 2.16 (s, 3H), 1.18 (t, J=6.2 Hz, 3H);

Mass (M+H$^+$) calcd for C$_{32}$H$_{40}$F$_3$N$_9$O$_4$ 671.71. found 672.25.

Example 65

Preparation of 1-(4-(4-((4-((4-(4-acetylpiperazin-1-yl)-2-methoxyphenyl)amino)-5-(trifluoromethyl)pyrimidin-2-yl)amino)-3-methoxyphenyl)piperazin-1-yl)-2-hydroxyethanone

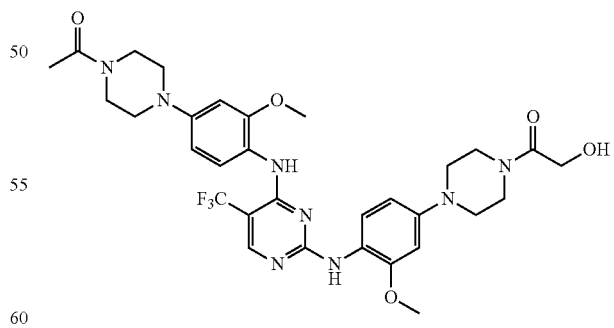

A target compound (24.5 mg, 74%) was obtained in the same manner as in Example 14 except that the compound prepared in Example 63 was used as a starting material instead of the compound prepared in Example 12.

$^1$H NMR (300 MHz, CDCl$_3$) δ 8.26 (s, 1H), 8.12 (d, J=8.0 Hz, 2H), 7.47 (s, 1H), 7.39 (s, 1H), 6.55-6.43 (m, 4H), 4.23 (s,

2H), 3.88 (s, 3H), 3.84-3.80 (m, 4H), 3.65 (s, 2H), 3.47 (s, 2H), 3.14 (s, 8H), 2.16 (s, 3H);

Mass (M+H$^+$) calcd for C$_{31}$H$_{37}$F$_3$N$_8$O$_5$ 658.67. found 659.23.

Example 66

Preparation of 1-(4-(3-methoxy-4-((2-((2-methoxy-4-(4-methylpiperazin-1-yl)phenyl-5-(trifluoromethyl)pyrimidin-4-yl)amino)phenyl)piperazin-1-yl)ethanone

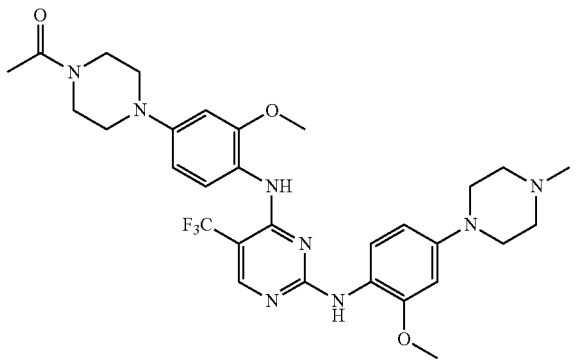 [SMILES: COc1cc(N2CCN(C)CC2)ccc1Nc1ncc(C(F)(F)F)c(Nc2ccc(N3CCN(C(C)=O)CC3)cc2OC)n1]

A target compound (9.3 mg, 30%) was obtained in the same manner as in Example 13 except that the compound prepared in Example 63 was used as a starting material instead of the compound prepared in Example 12, and methyliodide was used instead of methanesulfonylchloride.

$^1$H NMR (300 MHz, CD$_3$OD) δ 8.25 (s, 1H), 8.13 (d, J=8.0 Hz, 1H), 8.03 (d, J=8.5 Hz, 1H), 7.40-7.38 (m, 2H), 6.53-6.49 (m, 3H), 6.45 (d, J=8.5 Hz, 1H), 3.88 (s, 3H), 3.86 (s, 3H), 3.80 (s, 2H), 3.65 (s, 2H), 3.17 (s, 8H), 2.61 (s, 4H), 2.37 (s, 3H), 2.16 (s, 3H);

Mass (M+H$^+$) calcd for C$_{30}$H$_{37}$F$_3$N$_8$O$_3$ 614.66. found 615.23.

Example 67

Preparation of 1-(4-(3-methoxy-4-((2-((2-methoxy-4-(4-(methylsulfonyl)piperazin-1-yl)phenyl)amino)-5-(trifluoromethyl)pyrimidin-4-yl)amino)phenyl)piperazin-1-yl)ethanone

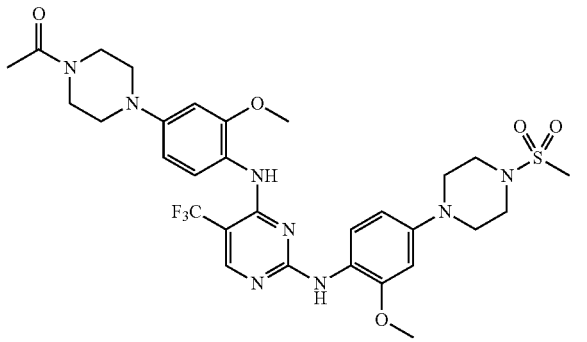

A target compound (7.8 mg, 23%) was obtained in the same manner as in Example 13 except that the compound prepared in Example 63 was used as a starting material instead of the compound prepared in Example 12.

$^1$H NMR (300 MHz, CD$_3$OD) δ 8.26 (s, 1H), 8.14-8.10 (m, 2H), 7.43 (s, 1H), 7.39 (s, 1H), 6.55-6.45 (m, 4H), 3.88 (s, 6H), 3.80 (s, 2H), 3.66 (s, 2H), 3.41 (s, 4H), 3.24 (s, 4H), 3.16 (s, 4H), 2.85 (s, 3H), 2.16 (s, 3H);

Mass (M+H$^+$) calcd for C$_{30}$H$_{37}$F$_3$N$_8$O$_5$S 678.73. found 679.14.

Example 68

Preparation of 1-(4-(4-((2-((4-(4-(2-hydroxyethyl)piperazin-1-yl)-2-methoxyphenyl)amino)-5-(trifluoromethyl)pyrimidin-4-yl)amino)-3-methoxyphenyl)piperazin-1-yl)ethanone

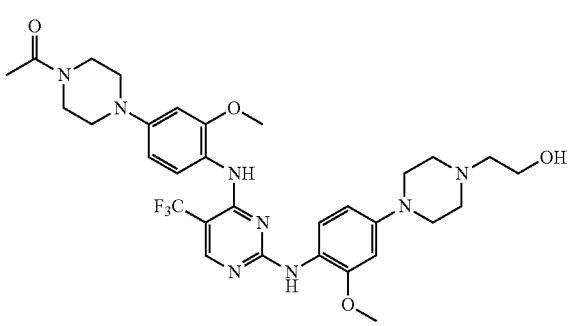 [SMILES: COc1cc(N2CCN(CCO)CC2)ccc1Nc1ncc(C(F)(F)F)c(Nc2ccc(N3CCN(C(C)=O)CC3)cc2OC)n1]

A target compound (15.6 mg, 48%) was obtained in the same manner as in Example 16 except that the compound prepared in Example 63 was used as a starting material instead of the compound prepared in Example 12.

$^1$H NMR (300 MHz, CD$_3$OD) δ 8.25 (s, 1H), 8.11 (d, J=8.0 Hz, 1H), 8.03 (d, J=8.5 Hz, 1H), 7.42 (s, 1H), 7.37 (s, 1H), 6.53 (s, 2H), 6.51 (d, J=8.0 Hz, 1H), 6.44 (d, J=8.5 Hz, 1H), 3.88 (s, 3H), 3.86 (s, 3H), 3.80 (s, 2H), 3.70-3.64 (m, 4H), 3.17 (s, 8H), 2.70 (s, 4H), 2.65 (s, 2H), 2.15 (s, 3H);

Mass (M+H$^+$) calcd for C$_{31}$H$_{39}$F$_3$N$_8$O$_4$ 644.69. found 645.12.

Example 69> Preparation of N2,N4-bis(2-methoxy-4-(piperazin-1-yl)phenyl)-5-(trifluoromethyl)pyrimidin-2,4-diamine

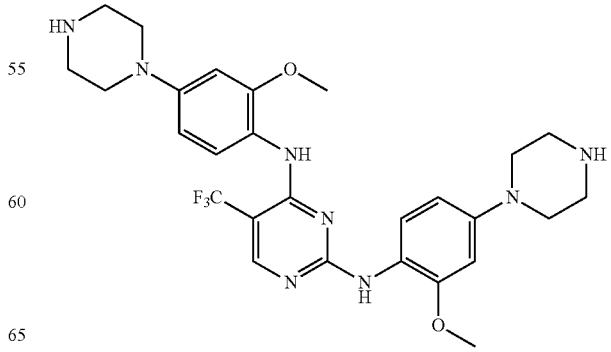

Step 1: Preparation of di-tert-butyl 4,4'-(((5-(trifluoromethyl)pyrimidin-2,4-diyl)bis(azanediyl))bis(3-methoxy-4,1-phenylene))bis(piperazin-1-carboxylate)

2,4-dichloro-5-(trifluoromethyl)pyrimidine (500 mg), potassium carbonate (796 mg) and the compound (1.42 g) prepared in Preparation Example 27 were dissolved in dimethylformamide (5 ml), and stirred at room temperature overnight. Upon completion of the reaction, the mixture was distilled under reduced pressure to remove the solvent, and diluted with ethyl acetate. The diluted mixture was washed with saturated brine, and the organic layer was dried with sodium sulfate. The organic layer was distilled under reduced pressure to remove the solvent and then separated by column chromatography to obtain a target compound (489 mg, 28%).

$^1$H NMR (300 MHz, CD$_3$OD) δ 8.25 (s, 1H), 8.09 (d, J=8.6 Hz, 1H), 7.39 (s, 1H), 6.64 (d, J=8.2 Hz, 1H), 6.49-6.39 (m, 3H), 6.46 (d, J=8.2 Hz, 1H), 3.88 (s, 3H), 3.86 (s, 3H), 3.61-3.56 (m, 8H), 3.12-3.06 (m, 4H), 2.98 (s, 4H), 1.49 (s, 18H).

Step 2: Preparation of N2,N4-bis(2-methoxy-4-(piperazin-1-yl)phenyl)-5-(trifluoromethyl)pyrimidin-2,4-diamine The compound (489 mg) prepared in Step 1 was dissolved in methylenechloride (6 ml), added with 4M HCl (dioxane solution, ml), and stirred at room temperature overnight. Upon completion of the reaction, the mixture was distilled under reduced pressure to remove the solvent, and dissolved again in methylenechloride. Then, the resultant was neutralized with a saturated solution of sodium bicarbonate, washed with saturated brine, and dried with sodium sulfate. The dried organic layer was distilled under reduced pressure to remove the solvent to obtain a target compound (320 mg, 89%).

$^1$H NMR (300 MHz, CD$_3$OD) δ 8.22 (s, 1H), 7.70 (d, J=8.2 Hz, 1H), 7.35 (d, J=8.2 Hz, 1H), 6.57 (s, 1H), 6.54 (s, 1H), 6.47 (d, J=8.6 Hz, 1H), 3.88 (s, 3H), 3.86 (s, 3H), 3.52 (s, 8H), 3.43 (s, 8H);

Mass (M+H$^+$) calcd for C$_{27}$H$_{33}$F$_3$N$_8$O$_2$ 558.60. found 559.08.

Example 70

Preparation of dimethyl 4,4'-(((5-(trifluoromethyl)pyrimidin-2,4-diyl)bis(azanediyl))bis(3-methoxy-4,1-phenylene))bis(piperazin-1-carboxylate)

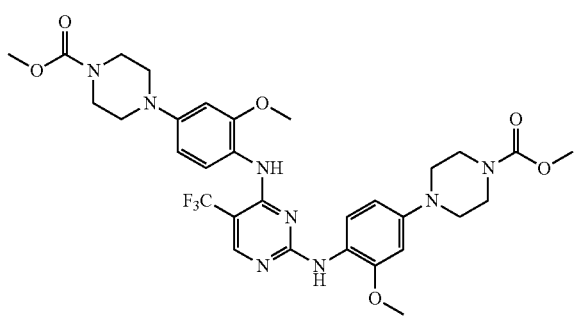

The compound (50 mg) prepared in Example 69 was dissolved in methylenechloride (1 ml), added with methyl choroformate (15 μl), and stirred at room temperature overnight. Upon completion of the reaction, the solvent was removed by distillation under reduced pressure, and purified with prep. TLC to obtain a target compound (5.6 mg, 15%).

$^1$H NMR (300 MHz, CD$_3$OD) δ 8.25 (s, 1H), 8.12-8.05 (m, 2H), 7.38 (s, 1H), 6.54-6.42 (m, 4H), 3.88 (s, 3H), 3.87 (s, 3H), 3.75 (s, 6H), 3.66 (s, 8H), 3.14-3.09 (m, 8H);

Mass (M+H$^+$) calcd for C$_{31}$H$_{37}$F$_3$N$_8$O$_6$ 674.67. found 675.11.

Example 71

Preparation of 4,4'-(((5-(trifluoromethyl)pyrimidin-2,4-diyl)bis(azanediyl))bis(3-methoxy-4,1-phenylene))bis(N-ethylpiperazin-1-carboxyamide)

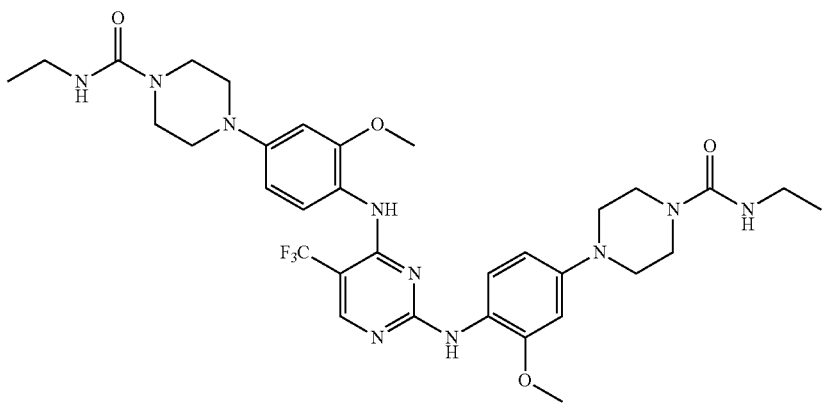 [SMILES: CCNC(=O)N1CCN(c2ccc(Nc3ncc(C(F)(F)F)c(Nc4ccc(N5CCN(C(=O)NCC)CC5)cc4OC)n3)c(OC)c2)CC1]

A target compound (22.2 mg, 50%) was obtained in the same manner as in Example 13 except that the compound prepared in Example 69 was used as a starting material instead of the compound prepared in Example 12, and ethyl isocyanate was used instead of methanesulfonylchloride.

¹H NMR (300 MHz, CD₃OD) δ 8.24 (s, 1H), 7.95 (d, J=8.2 Hz, 2H), 7.40 (s, 1H), 6.53 (d, J=8.2 Hz, 2H), 6.47 (d, J=8.6 Hz, 1H), 6.37 (d, J=8.6 Hz, 1H), 4.87-4.78 (m, 2H), 3.85 (s, 6H), 3.56 (s, 8H), 3.32 (q, J=7.2 Hz, 2H), 3.17 (s, 4H), 3.11 (s, 4H), 1.18 (t, J=7.2 Hz, 6H);

Mass (M+H⁺) calcd for $C_{33}H_{43}F_3N_{10}O_4$ 700.75. found 701.28.

Example 72

Preparation of 1,1'-(4,4'-(((5-(trifluoromethyl)pyrimidin-2,4-diyl)bis(azanediyl))bis(3-methoxy-4,1-phenylene))bis(piperazin-4,1))bis(2-hydroxyethanone)

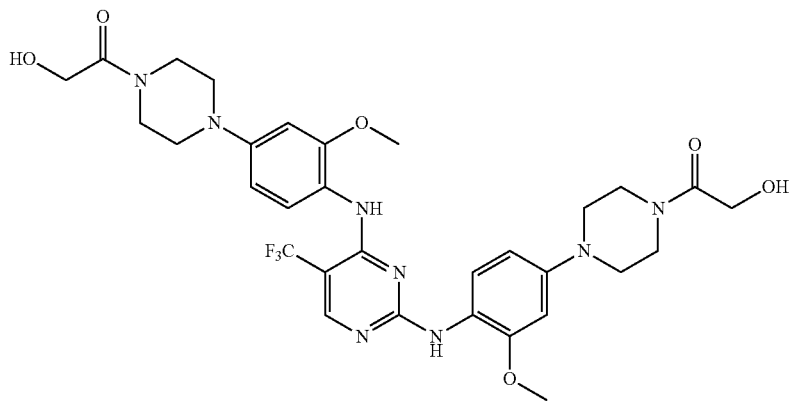

A target compound (8 mg, 19) was obtained in the same manner as in Example 14 except that the compound prepared in Example 69 was used as a starting material instead of the compound prepared in Example 12.

¹H NMR (300 MHz, CD₃OD) δ 8.27 (s, 1H), 8.18-8.11 (m, 2H), 7.45 (s, 1H), 7.41 (s, 1H), 6.54-6.44 (m, 4H), 4.23 (s, 4H), 3.89 (s, 3H), 3.87 (s, 3H), 3.85 (s, 4H), 3.65 (br, 2H), 3.46 (s, 4H), 3.18-3.14 (m, 8H);

Mass (M+H⁺) calcd for $C_{31}H_{37}F_3N_8O_6$ 674.67. found 675.22.

Example 73

Preparation of 1,1'-(4,4'-(((5-(trifluoromethyl)pyrimidin-2,4-diyl)bis(azanediyl))bis(3-difluoromethoxy)-4,1-phenylene))bis(piperazin-4,1-diyl))diethanone

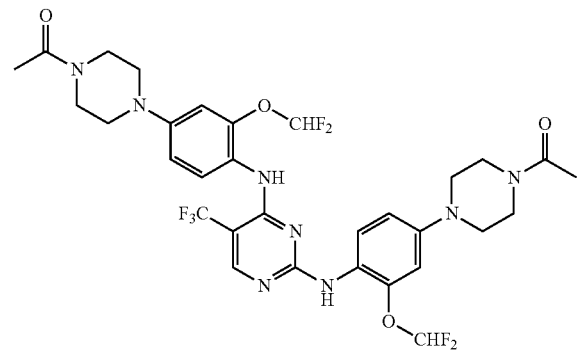 [SMILES: CC(=O)N1CCN(c2ccc(Nc3ncc(C(F)(F)F)c(Nc4ccc(N5CCN(C(C)=O)CC5)cc4OC(F)F)n3)c(OC(F)F)c2)CC1]

2,4-dichloro-5-(trifluoromethyl)pyrimidine (50 mg), 1-(4-(4-amino-3-(difluoromethoxy)phenyl)piperazin-1-yl)ethanone (140 mg) and potassium carbonate (90 mg) were dissolved in dimethylformamide (1 ml), and stirred at room temperature overnight. Upon completion of the reaction, the mixture was distilled under reduced pressure to remove the solvent, and diluted in ethyl acetate. The diluted mixture was washed with saturated brine, dried with sodium sulfate, and distilled under reduced pressure to remove the solvent. The concentrated mixture was purified by column chromatography to obtain a target compound (100 mg, 18%).

¹H NMR (300 MHz, CDCl₃) δ 8.28 (s, 1H), 7.94 (d, J=8.7 Hz, 1H), 7.31 (s, 1H), 7.13 (s, 1H), 6.81-6.63 (m, 5H), 6.47 (d, J=3.9 Hz, 1H), 3.79 (dd, J=5.0, 9.8 Hz, 4H), 3.64 (dd, J=5.1, 9.9 Hz, 4H), 3.24-3.03 (m, 8H), 2.16 (s, 3H), 2.15 (s, 3H);

Mass (M+H⁺) calcd for $C_{31}H_{33}F_7N_6O_4$ 714.25. found 715.18.

Example 74

Preparation of 1-(4-(4-((4-((4-(4-acetylpiperazin-yl)-2-chlorophenyl)amino)-5-chloropyrimidin-2-yl)amino)-3-methoxyphenyl)piperazin-1-yl)ethanone

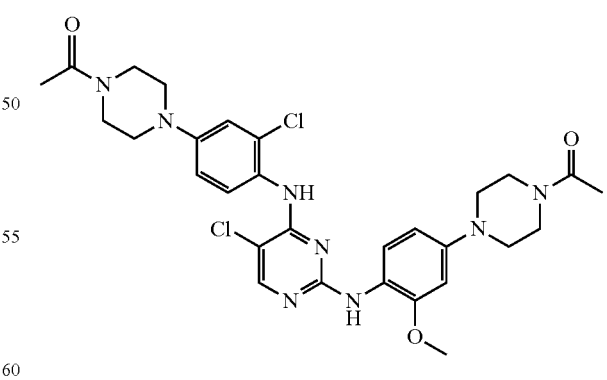

A target compound was obtained in the same manner as in Example 1 except that the compound prepared in Preparation Example 19 was used as a starting material instead of the compound prepared in Preparation Example 15.

¹H NMR (300 MHz, DMSO-d₆) δ 9.78 (br, 1H), 8.20 (s, 1H), 7.32 (d, J=8.9 Hz, 1H), 7.26 (d, J=8.9 Hz, 1H), 7.13 (d, J=2.7 Hz, 1H), 7.00 (dd, J=2.7, 8.9 Hz, 1H), 6.61 (d, J=2.4 Hz, 1H), 6.20 (br, 1H), 3.80 (s, 3H), 3.57 (m, 8H), 3.25 (m, 4H), 3.08 (m, 4H), 2.06 (s, 3H), 2.05 (s, 3H);

Mass (M+H⁺) calcd for $C_{29}H_{34}Cl_2N_8O_3$ 612.21. found 613.13.

Example 75

Preparation of 1,1'-(4,4'-(((5-chloropyrimidin-2,4-diyl)bis(azanediyl))bis(3-chloro-4,1-phenylene))bis(piperazin-4,1-diyl))diethanone

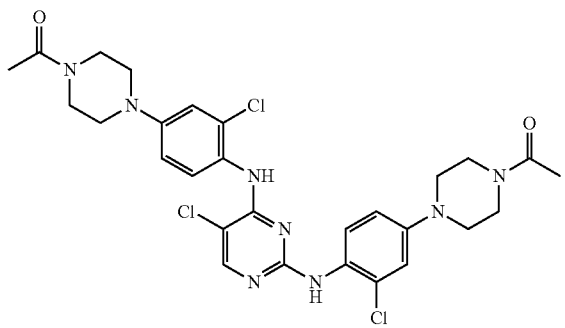 [SMILES: CC(=O)N1CCN(c2ccc(Nc3ncc(Cl)c(Nc4ccc(N5CCN(C(C)=O)CC5)cc4Cl)n3)c(Cl)c2)CC1]

A target compound was obtained in the same manner as in Example 1 except that the compound prepared in Preparation Example 19 was used as a starting material instead of the compound prepared in Preparation Example 15, and the compound prepared in Preparation Example 6 was used instead of the compound prepared in Preparation Example 1.

¹H NMR (300 MHz, DMSO-d₆) δ 9.18 (br, 1H), 8.86 (br, 1H), 8.12 (s, 1H), 7.37 (d, J=4.0 Hz, 1H), 7.34 (d, J=4.0 Hz, 1H), 7.10 (d, J=2.7 Hz, 1H), 7.00 (d, J=2.7 Hz, 1H), 6.92 (d, J=2.7 Hz, 1H), 6.89 (d, J=2.7 Hz, 1H), 6.75 (dd, J=2.6, 9.1 Hz, 1H), 3.57 (m, 8H), 3.14 (m, 8H), 2.05 (s, 3H), 2.04 (s, 3H);

Mass (M+H⁺) calcd for $C_{28}H_{31}Cl_3N_8O_2$ 616.16. found 617.07.

Example 76

Preparation of 1-(4-(4-((2-((4-(4-acetylpiperazin-1-yl)-2-methoxyphenyl)amino)-5-chloropyrimidin-4-yl)amino)-3-phenoxyphenyl)piperazin-1-yl)ethanone

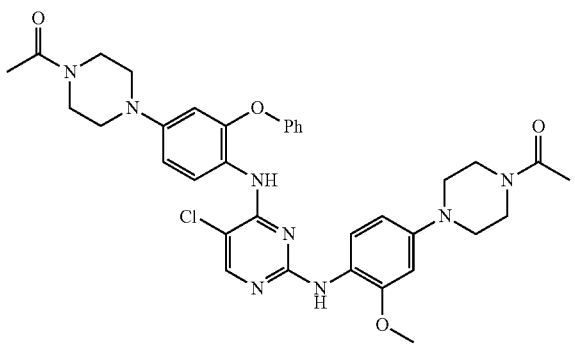 [SMILES: COc1cc(N2CCN(C(C)=O)CC2)ccc1Nc1ncc(Cl)c(Nc2ccc(N3CCN(C(C)=O)CC3)cc2Oc2ccccc2)n1]

A target compound was obtained in the same manner as in Example 1 except that the compound prepared in Preparation Example 20 was used as a starting material instead of the compound prepared in Preparation Example 15.

¹H NMR (300 MHz, DMSO-d₆) δ 9.55 (br, 1H), 8.08 (s, 1H), 7.30 (m, 4H), 7.05 (t, J=7.4 Hz, 1H), 6.89 (br, 1H), 6.86 (br, 1H), 6.82 (dd, J=2.6, 8.9 Hz, 1H), 6.67 (d, J=2.4 Hz, 1H), 6.59 (d, J=2.4 Hz, 1H), 6.29 (br, 1H), 3.79 (s, 3H), 3.56 (m, 8H), 3.11 (m, 8H), 2.05 (s, 3H), 2.03 (s, 3H);

Mass (M+H⁺) calcd for $C_{35}H_{39}ClN_8O_4$ 670.28. found 671.24.

Example 77

Preparation of 5-chloro-N2,N4-bis(2-methoxy-4-(piperazin-1-yl)phenyl)pyrimidin-2,4-diamine

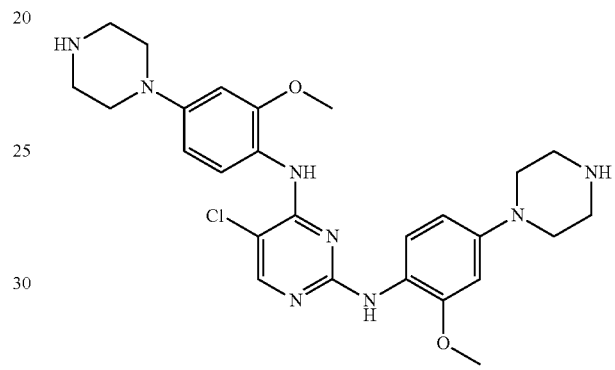

Step 1: Preparation of di-tert-butyl-4,4'-(4,4'0(5-chloropyrimidin-2,4-diyl)bis(azanediyl)bis(3-methoxy-4,1-phenylene))dipiperazin-1-carboxylate The compound (40 mg) prepared in Preparation Example 34 and the compound (60 mg) prepared in Preparation Example 35 were dissolved in 0.08M HCl ethoxyethanol solution (1.2 mg), and stirred at 115° C. overnight. Upon completion of the reaction, the mixture was distilled under reduced pressure to remove the solvent, and diluted with ethyl acetate. The diluted mixture was neutralized a saturated solution of sodium carbonate, and the organic layer was extracted. The extracted organic layer was dried with sodium sulfate. The dried organic layer was distilled under reduced pressure to remove the solvent and purified by column chromatography to obtain a target compound.

Step 2: Preparation of 5-chloro-N2,N4-bis(2-methoxy-4-(piperazin-1-yl)phenyl)pyrimidin-2,4-diamine A target compound was obtained in the same manner as in Step 2 of Example 69 except that the compound prepared in Step 1 above was used as a starting material instead of the compound prepared in Step 1 of Example 69.

¹H NMR (300 MHz, DMSO-d₆) δ 8.84 (br, 4H), 8.52 (br, 1H), 8.07 (s, 1H), 7.65 (d, J=8.6 Hz, 1H), 7.50 (d, J=8.6 Hz, 1H), 6.75 (d, J=2.4 Hz, 1H), 6.67 (d, J=2.4 Hz, 1H), 6.52 (dd, J=2.4, 8.7 Hz, 1H), 6.40 (dd, J=2.0, 8.6 Hz, 1H), 3.82 (s, 3H), 3.79 (s, 3H), 3.33 (m, 16H);

Mass (M+H⁺) calcd for $C_{26}H_{33}ClN_8O_2$ 524.24. found 525.15.

Example 78

Preparation of 4,4'-(((5-chloropyrimidin-2,4-diyl)bis(azanediyl))bis(3-methoxy-4,1-phenylene))bis(N-ethylpiperazin-1-carboxyamide)

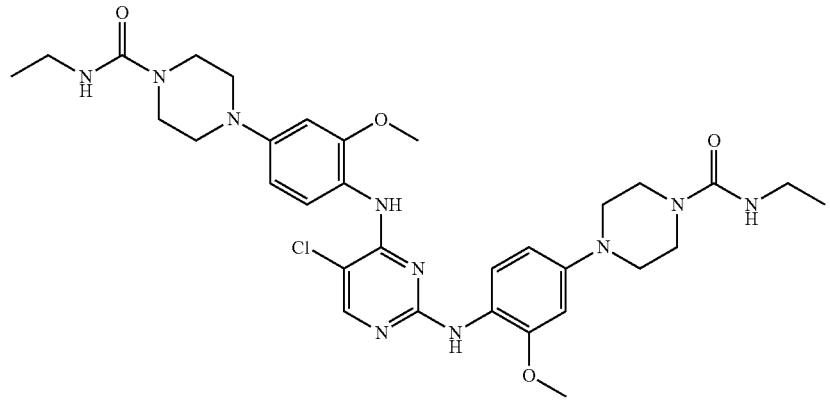 [SMILES: CCNC(=O)N1CCN(c2ccc(Nc3ncc(Cl)c(Nc4ccc(N5CCN(C(=O)NCC)CC5)cc4OC)n3)c(OC)c2)CC1]

A target compound (22 mg) was obtained in the same manner as in Example 13 except that the compound prepared in Example 77 was used as a starting material instead of the compound prepared in Example 12, and ethyl isocyanate was used instead of methane sulfonylchloride.

$^1$H NMR (300 MHz, DMSO-$d_6$) δ 9.17 (br, 1H), 8.12 (s, 1H), 7.36 (d, J=8.6 Hz, 1H), 7.30 (m, 1H), 6.72 (d, J=2.4 Hz, 1H), 6.65 (d, J=2.4 Hz, 1H), 6.55 (m, 2H), 6.51 (dd, J=2.2, 8.8 Hz, 1H), 6.33 (m, 1H), 3.79 (s, 6H), 3.14 (m, 20H), 1.02 (m, 6H);

Mass (M+H$^+$) calcd for $C_{32}H_{43}ClN_{10}O_4$ 666.32. found 667.26.

Example 79

Preparation of 5-chloro-N2,N4-bis(2-methoxy-4-(4-methylsulfonyl)piperazin-1-yl)phenyl)pyrimidin-2,4-diamine

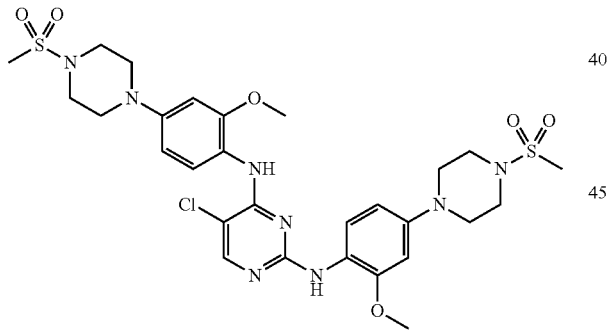

A target compound (8 mg, 23%) was obtained in the same manner as in Example 13 except that the compound prepared in Example 77 was used as a starting material instead of the compound prepared in Example 12.

$^1$H NMR (300 MHz, DMSO-$d_6$) δ 8.11 (s, 1H), 7.42 (d, J=7.9 Hz, 1H), 7.35 (d, J=7.9 Hz, 1H), 6.74 (d, J=2.4 Hz, 1H), 6.65 (d, J=2.4 Hz, 1H), 6.52 (dd, J=2.4, 8.7 Hz, 1H), 6.37 (d, J=8.7 Hz, 1H), 3.795 (s, 3H), 3.789 (s, 3H), 3.3 (m, 16H), 2.94 (s, 3H), 2.93 (s, 3H);

Mass (M+H1 calcd for $C_{28}H_{37}ClN_8O_6S_2$ 680.20. found 681.16.

Example 80

Preparation of 1,1'-(4,4'(((5-chloropyrimidin-2,4-diyl)bis(azanediyl))bis(3-methoxy-4,1-phenylene))bis(piperazin-4,1-diyl))bis(2-hydroxyethanone)

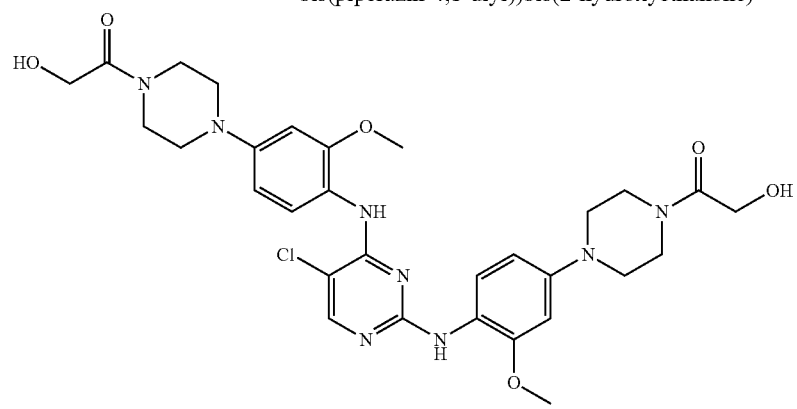

A target compound (19 mg) was obtained in the same manner as in Example 14 except that the compound prepared in Example 77 was used as a starting material instead of the compound prepared in Example 12.

$^1$H NMR (300 MHz, CDCl$_3$) δ 8.30 (d, J=8.6 Hz, 1H), 8.17 (d, J=8.6 Hz, 1H), 8.02 (s, 1H), 7.59 (s, 1H), 6.53 (m, 4H), 4.24 (s, 2H), 4.23 (s, 2H), 3.92 (s, 3H), 3.88 (s, 3H), 3.84 (m, 4H), 3.46 (m, 4H), 3.14 (m, 8H);

Mass (M+H$^+$) calcd for C$_{30}$H$_{37}$ClN$_8$O$_6$ 640.25. found 641.10.

Example 81

Preparation of 1-(4-(4-((5-chloro-4-((2-fluoro-4-(piperazin-1-yl)phenyl)amino)pyrimidin-2-yl)amino)-3-methoxyphenyl)piperazin-1-yl)ethanone

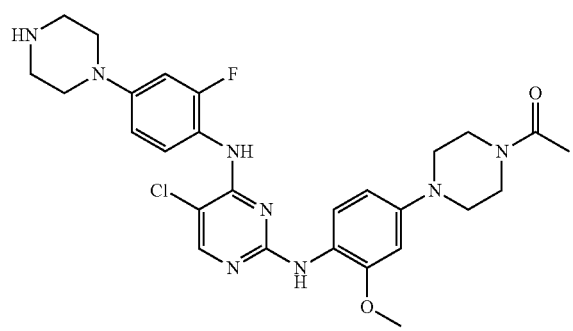 [SMILES: COc1cc(N2CCN(C(C)=O)CC2)ccc1Nc1ncc(Cl)c(Nc2ccc(N3CCNCC3)cc2F)n1]

Step 1: Preparation of tert-butyl-4-(4-(4-(4-(tert-butoxycarbonyl)piperazin-1-yl)-2-fluorophenylamino)-5-chloropyrimidin-2-ylamino)-3-methoxyphenyl)piperazin-1-carboxylate A target compound was obtained in the same manner as in Example 1 except that the compound prepared in Preparation Example 22 was used as a starting material instead of the compound prepared in Preparation Example 15.

Step 2: Preparation of 1-(4-(4-((5-chloro-4-((2-fluoro-4-(piperazin-1-yl)phenyl)amino)pyrimidin-2-yl)amino)-3-methoxyphenyl)piperazin-1-yl)ethanone A target compound was obtained in the same manner as in Step 2 of Example 12 except that the compound prepared in Step 1 above was used as a starting material instead of the compound prepared in Step 1 of Example 12.

$^1$H NMR (300 MHz, DMSO-d$_6$) δ 9.39 (br, 1H), 8.81 (br, 2H), 8.14 (s, 1H), 7.40 (d, J=8.3 Hz, 1H), 7.30 (t, J=8.9 Hz, 1H), 7.02 (dd, J=2.6, 13.6 Hz, 1H), 6.84 (dd, J=2.3, 8.8 Hz, 1H), 6.63 (d, J=2.4 Hz, 1H), 6.29 (d, J=8.6 Hz, 1H), 3.79 (s, 3H), 3.59 (m, 4H), 3.42 (m, 4H), 3.25 (m, 4H), 3.13 (m, 2H), 3.06 (m, 2H), 2.05 (s, 3H);

Mass (M+H$^+$) calcd for C$_{27}$H$_{32}$ClFN$_8$O$_2$ 554.23. found 555.13.

Example 82

Preparation of 1-(4-(4-((4-((4-(4-acetylpiperazin-1-yl)-2-fluorophenyl)amino)-5-chloropyrimidin-2-yl)amino)-3-methoxyphenyl)piperazin-1-yl-ethanone

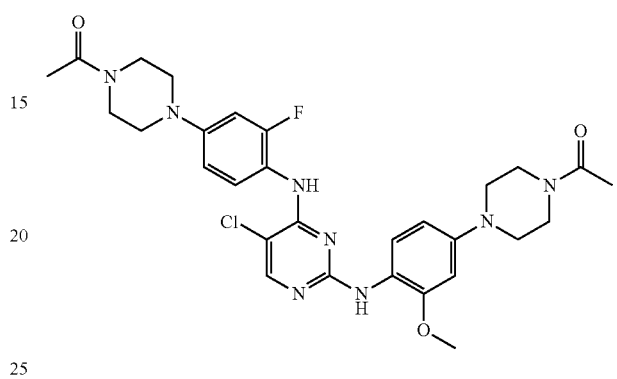

A target compound (23 mg) was obtained in the same manner as in Example 35 except that the compound prepared in Example 81 was used as a starting material instead of the compound prepared in Example 33.

$^1$H NMR (300 MHz, DMSO-d$_6$) δ 9.36 (br, 1H), 8.12 (s, 1H), 7.37 (d, J=7.2 Hz, 1H), 7.24 (t, J=8.9 Hz, 1H), 6.95 (dd, J=2.5, 13.7 Hz, 1H), 6.81 (dd, J=2.1, 8.7 Hz, 1H), 6.62 (d, J=2.3 Hz, 1H), 6.21 (m, 1H), 3.79 (s, 3H), 3.0-3.6 (m, 16H), 2.06 (s, 3H), 2.05 (s, 3H);

Mass (M+H$^+$) calcd for C$_{29}$H$_{34}$ClFN$_8$O$_3$ 596.24. found 597.17.

Example 83

Preparation of 1-(4-(4-((4-((4-(4-acetylpiperazin-1-yl)-2-methoxyphenyl)amino)-5-chloropyrimidin-2-yl)amino)-3-methoxyphenyl)piperazin-1-yl)-2-hydroxyethanone

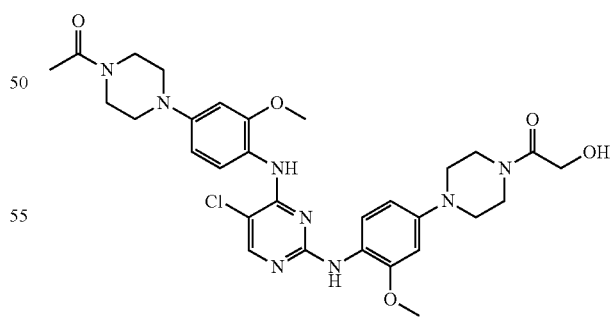

The compound (30 mg) prepared in Example 52 was dissolved in methylenechloride (1 ml), added with trifluoroacetic acid (91 ml), stirred at room temperature for 5 minutes, and dried under reduced pressure. The dried reactants were dissolved in methylenechloride (1 ml) along with glycolic acid (95 mg), EDCI (11 mg) and DMAP (7 mg), and stirred at room temperature overnight. Upon completion of the reaction, the mixture was distilled under reduced pressure to remove the solvent and purified with prep. TLC to obtain a target compound (22 mg).

$^1$H NMR (300 MHz, CDCl$_3$) δ 8.30 (d, J=7.86 Hz, 1H), 8.18 (d, J=10.62 Hz, 1H), 8.02 (s, 1H), 7.57 (s, 1H), 6.58-6.48 (m, 4H), 3.92 (d, J=2.31 Hz, 3H), 3.88 (d, J=2.19 Hz, 3H), 3.87-3.78 (m, 4H), 3.69-3.62 (m, 3H), 3.50-3.44 (m, 2H), 3.20-3.10 (m, 7H), 2.15 (s, 4H);

Mass (M+H$^+$) calcd for C$_{30}$H$_{37}$ClN$_8$O$_5$ 624.26. found 625.11.

Example 84

Preparation of methyl 4-(4-((4-((4-(4-acetylpiperazin-1-yl)-2-methoxyphenyl)amino)-5-chloropyrimidin-2-yl)amino)-3-methoxyphenyl)piperazin-1-carboxylate

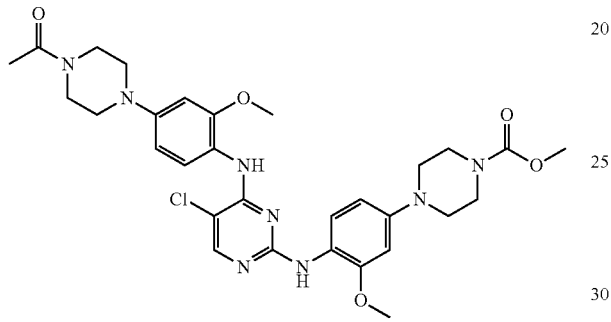

The compound (30 mg) prepared in Example 52 was dissolved in methylenechloride (1 ml), added with trifluoroacetic acid (1 μl), stirred at room temperature for 5 minutes, and dried under reduced pressure. The dried reactants were dissolved in methylenechloride (1 ml), and methyl choroformate (10 μl) and triethylamine (20 μl) were stirred at 0° C. for 30 minutes. Upon completion of the reaction, the mixture was concentrated under reduced pressure and purified with prep. TLC to obtain a target compound (18 mg).

$^1$H NMR (300 MHz, CDCl$_3$) δ 8.29 (d, J=7.35 Hz, 1H), 8.13 (d, J=8.64 Hz, 1H), 8.01 (s, 1H), 7.56 (s, 1H), 6.55-6.47 (m, 4H), 3.94 (s, 3H), 3.91 (s, 3H), 3.83-3.75 (m, 2H), 3.74 (s, 3H), 3.65 (s, 6H), 3.19-3.07 (m, 7H), 2.16 (s, 3H);

Mass (M+H$^+$) calcd for C$_{30}$H$_{37}$ClN$_8$O$_5$ 624.26 found 625.24.

Example 85

Preparation of 1-(4-(4-((5-chloro-2-((4-(4-(2-hydroxyethyl)piperazin-1-yl)-2-methoxyphenyl)amino)pyrimidin-4-yl)amino)-3-methoxyphenyl)piperazin-1-yl)ethanone

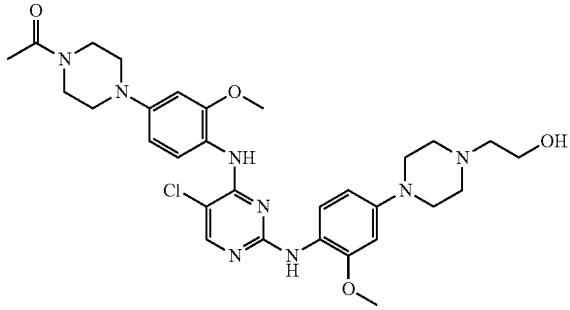 [SMILES: COc1cc(N2CCN(CCO)CC2)ccc1Nc1ncc(Cl)c(Nc2ccc(N3CCN(C(C)=O)CC3)cc2OC)n1]

The compound (30 mg) prepared in Example 52 was dissolved in methylenechloride (1 ml), added with trifluoroacetic acid (1 ml), stirred at room temperature for 5 minutes, and dried under reduced pressure. The dried reactants were dissolved in dimethylformamide (1 ml) along with 2-bromoethanol (5 μl) and potassium carbonate (21 mg), and stirred at 60° C. overnight. Upon completion of the reaction, the resultant was distilled under reduced pressure to remove dimethylformamide and purified with prep. TLC to obtain a target compound (11 mg).

$^1$H NMR (300 MHz, CDCl$_3$) δ 8.26 (d, J=8.64 Hz, 1H), 8.08 (d, J=8.61 Hz, 1H), 7.54 (s, 1H), 7.21 (s, 1H), 6.55-6.47 (m, 4H), 5.59 (s, 1H), 5.00 (s, 1H), 4.22-4.19 (m, 2H), 3.91 (s, 3H), 3.86 (s, 3H), 3.73-3.62 (m, 6H), 3.18-3.12 (m, 8H), 2.74-2.72 (m, 4H), 2.67-2.63 (m, 2H), 2.16 (s, 3H), 2.10 (s, 3H);

Mass (M+H$^+$) calcd for C$_{30}$H$_{39}$ClN$_8$O$_4$ 610.28. found 611.27.

Example 86

Preparation of 4-(4-((4-((4-(4-acetylpiperazin-1-yl)-2-methoxyphenyl)amino)-5-chloropyrimidin-2-yl)amino)-3-methoxyphenyl)piperazin-1-sulfonamide

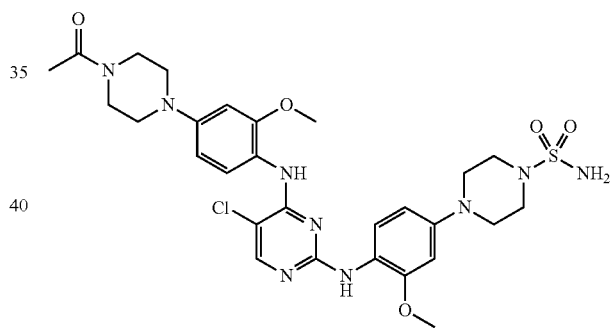

The compound (30 mg) prepared in Example 52 was dissolved in methylenechloride (1 ml), added with trifluoroacetic acid (1 ml), stirred at room temperature for 5 minutes, and dried under reduced pressure. The dried reactants, disulfamide (20 mg) and triethylamine (10 μl) were dissolved in 1,4-dioxane (1 ml), and refluxed for 2 hours. Then, the resultant was distilled under reduced pressure to remove the solvent and purified with HPLC to obtain a target compound as a white solid.

$^1$H NMR (300 MHz, CDCl$_3$) 8.16 (d, J=8.61 Hz, 1H), 8.02 (d, J=10.44 Hz, 2H), 7.48 (s, 1H), 7.16 (s, 1H), 6.55-6.46 (m, 4H), 3.90 (s, 3H), 3.85 (s, 3H), 3.82-3.79 (m, 2H), 3.67-3.65 (m, 2H), 3.35 (d, J=4.23 Hz, 4H), 3.24 (d, J=4.11 Hz, 4H), 3.17-3.15 (m, 4H), 2.17 (d, J=6.99 Hz, 2H), 1.25 (s, 1H));

Mass (M+H$^+$) calcd for C$_{28}$H$_{36}$ClN$_9$O$_5$S 645.22. found 646.16.

Example 87

Preparation of 1-(4-(4-((5-chloro-2-((2-methoxy-4-(4-methylsulfonyl)piperazin-1-yl)phenyl)amino)-3-amino)pyrimidin-4-yl)amino)-3-methoxyphenyl)piperazin-1-yl)ethanone

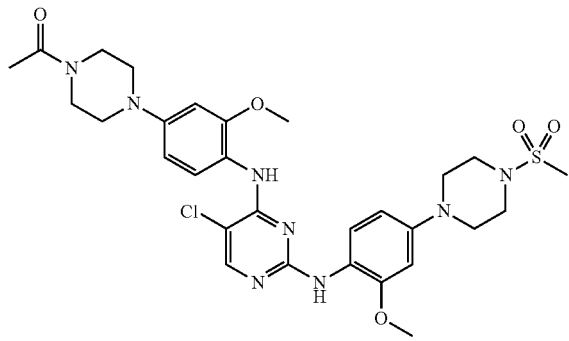 [SMILES: COc1cc(N2CCN(S(C)(=O)=O)CC2)ccc1Nc1ncc(Cl)c(Nc2ccc(N3CCN(C(C)=O)CC3)cc2OC)n1]

A target compound was obtained in the same manner as in Example 84 except that methanesulfonylchloride was used instead of methyl choroformate.

$^1$H NMR (300 MHz, CDCl$_3$) δ 8.29 (d, J=5.22 Hz, 1H), 8.18 (d, J=5.16 Hz, 1H), 8.03 (s, 1H), 7.59 (s, 1H), 6.58-6.52 (m, 5H), 3.90 (s, 3H), 3.67 (s, 2H), 3.43 (d, J=2.82 Hz, 4H), 3.25 (d, J=2.74 Hz, 4H), 3.20-3.16 (m, 5H), 2.86 (s, 3H), 2.18 (s, 3H);

Mass (M+H$^+$) calcd for C$_{29}$H$_{37}$ClN$_8$O$_5$S 644.23. found 645.29.

Example 88

Preparation of 1-(4-(4-((2-((4-(4-acetylpiperazin-1-yl)-2-methoxyphenyl)amino)-5-chloropyrimidin-4-yl)amino)-3-(difluoromethoxy)phenyl)piperazin-1-yl)-2-hydroxyethanone

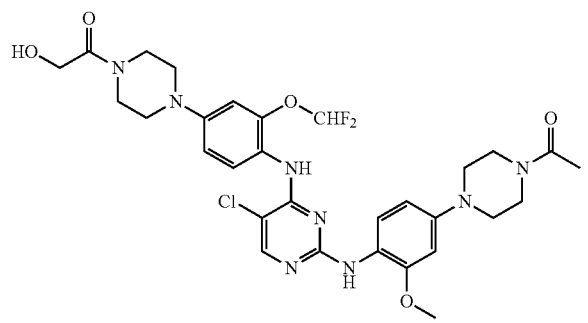 [SMILES: COc1cc(N2CCN(C(C)=O)CC2)ccc1Nc1ncc(Cl)c(Nc2ccc(N3CCN(C(=O)CO)CC3)cc2OC(F)F)n1]

A target compound was obtained in the same manner as in Example 14 except that the compound prepared in Example 33 was used instead of the compound prepared in Example 12.

$^1$H NMR (300 MHz, CDCl$_3$) δ 8.24 (d, J=8.85 Hz, 1H), 8.06 (d, J=9.3 Hz, 2H), 7.31 (s, 1H), 6.82-6.75 (m, 2H), 6.52 (d, J=7.26 Hz, 2H), 6.45 (d, J=8.94 Hz, 1H), 4.23 (s, 2H), 3.87 (s, 5H), 3.78 (t, J=4.26 Hz, 2H), 3.63 (s, 3H), 3.47 (d, J=4.26 Hz, 2H), 3.19 (d, J=3.18 Hz, 4H), 3.12-3.07 (m, 4H), 2.15 (s, 3H);

Mass (M+H$^+$) calcd for C$_{30}$H$_{35}$ClF$_2$N$_8$O$_5$ 660.24. found 661.28.

Example 89

Preparation of 1-(4-(3-(difluoromethoxy)-4-(5-fluoro-2-(2-methoxy-4-(piperazin-1-yl)phenylamino)pyrimidin-4-ylamino)phenyl)piperazin-1-yl)ethanone

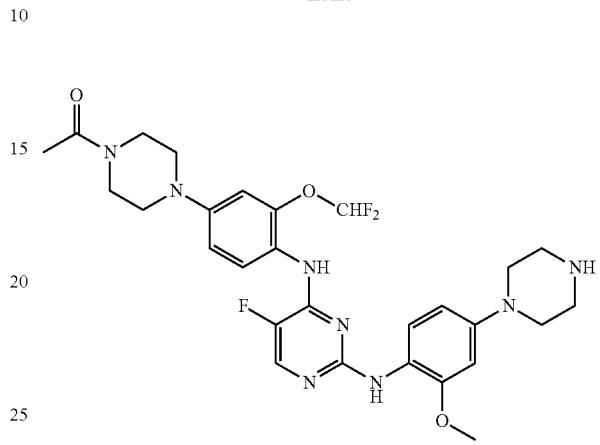

1-(4-(4-(2-chloro-5-fluoropyrimidine-4-ylamino)-3-(difluoromethoxy)phenyl)piperazin-1-yl)ethanone (320 mg) and tert-butyl-4-(4-amino-3-methoxyphenyl)piperazin-1-carboxylate (236 mg) were dissolved in 0.08M HCl ethoxyethanol solution (7.7 ml), and stirred at 115° C. overnight. Upon completion of the reaction, the mixture was distilled under reduced pressure to remove the solvent, and the thus obtained oil was diluted with ethyl acetate. The diluted mixture was neutralized with a saturated aqueous solution of sodium bicarbonate, subjected to layer separation, and the extracted organic layer obtained as a result of layer separation was dried with sodium sulfate. The dried organic layer was distilled under reduced pressure to remove the solvent and purified by column chromatography to obtain a target compound (100 mg, 22%).

$^1$H NMR (500 MHz, CD$_3$OD) δ 7.84 (s, 1H), 7.70 (d, J=8.5 Hz, 1H), 7.53 (d, J=8.5 Hz, 1H), 6.89 (d, J=9.0 Hz, 1H), 6.84 (s, 1H), 6.63 (s, 1H), 6.53 (t, J=96.5 Hz, 1H), 6.29 (d, J=9.0 Hz, 1H), 3.83 (s, 3H), 3.75 (t, J=4.7 Hz, 2H), 3.71 (t, J=4.7 Hz, 2H), 2.16 (s, 3H);

Mass (M+H$^+$) calcd for C$_{28}$H$_{33}$F$_3$N$_8$O$_3$ 586.61. found 586.98.

Experimental Example 1

Evaluation of ALK Inhibitory Activity

In order to measure the inhibitory activity of N2,N4-bis(4-(piperazin-1-yl)phenyl)pyrimidin-2,4-diamine derivatives represented by Chemical Formula 1 according to the present invention against the ALK proliferation at the enzyme level, an experiment was performed as follows.

In order to measure the inhibitory activity against ALK, a Grainer 96-well round type bottom plate was added with the compounds (2 μl) prepared in Examples 1 to 89, and mixed with ALK enzyme (1 ul) and a peptide substrate (2 μl) with biotin attached thereto for 15 minutes and cultured thereafter. Here, ATP solution (5 μl) was added thereto and kinase reaction was performed at room temperature for 30 minutes. XL 665 (5 μl), to which Streptavidin dissolved in ethylenediaminetetraacetic acid solution was attached, anti-phosphotyrosine antibody (5 μl), to which europium ($Eu^{3+}$) was attached, were added to a reaction solution to stop the reaction, cultured for 1 hour, and analyzed using Homogeneous Time-resolved fluorescence (HTRF, Cisbio). The result was read by a Wallac Envision 2103 device at the wavelength range of 615/665 nm. The $IC_{50}$ of the test compounds used in the above experiment was obtained using a prism (version 5.01 graphpad) software.

The $IC_{50}$ of the compounds that reduced the ALK enzyme activity is shown Table 1 below.

TABLE 1

| Ex. | ALK wt. $IC_{50}$ (μM) | ALK L1196M $IC_{50}$ (μM) | Ex. | ALK wt. $IC_{50}$ (μM) | ALK L1196M $IC_{50}$ (μM) |
|---|---|---|---|---|---|
| 1 | 0.025 | 0.0234 | 46 | 0.58 | — |
| 2 | 0.038 | 0.364 | 47 | >1 | — |
| 3 | 0.033 | 0.361 | 48 | 0.76 | — |
| 4 | 0.15 | — | 49 | 1.2 | — |
| 5 | 0.029 | 0.305 | 50 | >1 | — |
| 6 | 0.065 | 0.247 | 51 | >1 | — |
| 7 | 0.012 | 0.075 | 52 | 0.025 | 0.55 |
| 8 | 0.064 | 0.3266 | 53 | 0.99 | — |
| 9 | 0.3 | — | 54 | 4.5 | — |
| 10 | 0.018 | 0.207 | 55 | 0.12 | — |
| 11 | 0.009 | 0.049 | 56 | 0.004 | 0.004 |
| 12 | 0.009 | 0.043 | 57 | 0.003 | 0.002 |
| 13 | 0.025 | 0.113 | 58 | 0.004 | 0.002 |
| 14 | 0.016 | 0.063 | 59 | 0.007 | 0.003 |
| 15 | 0.085 | 0.301 | 60 | 0.01 | 0.003 |
| 16 | 0.014 | 0.056 | 61 | 0.004 | 0.011 |
| 17 | 1.0 | — | 62 | 0.031 | 0.033 |
| 18 | 0.011 | 0.086 | 63 | 0.003 | 0.003 |
| 19 | 0.12 | 0.751 | 64 | 0.006 | 0.008 |
| 20 | 0.13 | 1.101 | 65 | 0.007 | 0.003 |
| 21 | 0.012 | 0.043 | 66 | 0.006 | 0.003 |
| 22 | 0.01 | 0.257 | 67 | 0.014 | 0.039 |
| 23 | 0.023 | 0.183 | 68 | 0.003 | 0.005 |
| 24 | 0.067 | 0.846 | 69 | 0.003 | 0.004 |
| 25 | 0.015 | — | 70 | 0.16 | — |
| 26 | 0.022 | 0.235 | 71 | 0.02 | 0.046 |
| 27 | 0.019 | 0.567 | 72 | 0.003 | 0.005 |
| 28 | 0.011 | 0.169 | 73 | 0.016 | 0.058 |
| 29 | 0.079 | 0.698 | 74 | 0.007 | 0.044 |
| 30 | 0.014 | 0.265 | 75 | 0.04 | 0.26 |
| 31 | 0.031 | 0.394 | 76 | >1 | — |
| 32 | 0.21 | — | 77 | 0.003 | 0.004 |
| 33 | 0.005 | 0.01 | 78 | 0.018 | — |
| 34 | 0.570 | — | 79 | 0.02 | 0.064 |
| 35 | 0.01 | 0.041 | 80 | 0.006 | 0.011 |
| 36 | 0.01 | 0.031 | 81 | 0.017 | 0.13 |
| 37 | 0.012 | 0.049 | 82 | 0.011 | 0.28 |
| 38 | 0.017 | 0.11 | 83 | 0.004 | 0.027 |
| 39 | 0.35 | — | 84 | 0.010 | 0.094 |
| 40 | 0.029 | — | 85 | 0.002 | 0.021 |
| 41 | 0.073 | — | 86 | 0.009 | 0.091 |
| 42 | 0.016 | 0.14 | 87 | 0.010 | 0.053 |
| 43 | 0.032 | — | 88 | 0.004 | 0.027 |
| 44 | 0.008 | 0.036 | 89 | 0.013 | 0.17 |
| 45 | 0.01 | — | Control group | 0.036 | 0.22 |

In Table 1 above, '-' denotes that no experiment was performed.

As shown in Table 1 above, the $IC_{50}$ of the compounds prepared in Examples 1, 3, 5, 7, 10 to 14, 16, 18, 21 to 23, 25 to 28, 30 to 31, 33, 35 to 38, 40, 42 to 45, 52, 56 to 69, 71 to 75, and 77 to 89 according to the present invention was shown to be lower than that when Crizotinib®, a control group, was used. Among them, the $IC_{50}$ of the compounds prepared in Examples 7, 11, 12, 14, 16, 18, 21 to 23, 25 to 28, 30 to 31, 32, 35 to 38, 40, 42 to 45, 52, 56 to 69, 71 to 75, and 77 to was shown to be lower even in L1196M, a cancer cell containing ALK enzyme than that when Orizotinib®, a control group, was used.

This indicates that the N2,N4-bis(4-(piperazin-1-yl)phenyl)pyrimidin-2,4-diamine derivatives according to the present invention have the inhibitory activity against the ALK activity at enzyme level, and in particular, they have superior inhibitory activity to that of Crizotinib® (0.036 μM, a positive control), being used as a therapeutic agent for non-small cell lung cancer, by inhibiting the activity of ALK.

Accordingly, the N2,N4-bis(4-(piperazin-1-yl)phenyl)pyrimidin-2,4-diamine derivative of the present invention has an excellent inhibitory activity against ALK activity, and thus can be used as an effective inhibitor of ALK activity as well as a pharmaceutical composition for preventing or treating cancer such as non-small cell lung cancer, neuroblastoma, inflammatory myelofibroblast tumor, rhabdomyosarcoma, myofibroblastoma, breast cancer, stomach cancer, lung cancer, melanoma, etc.

Experimental Example 2

Evaluation of ACK1 Inhibitory Activity

In order to measure the inhibitory activity of N2,N4-bis(4-(piperazin-1-yl)phenyl)pyrimidin-2,4-diamine derivatives represented by Chemical Formula 1 according to the present invention against the ACK1 proliferation at the enzyme level, an experiment was performed as follows.

In order to measure the inhibitory activity against ACK1, a Grainer 96-well round type bottom plate was added with the compounds prepared in Examples 1 to 14, 10, 21 to 31, 35 to 38, 40 to 45, 56 to 75, 77 to 85, and 88 in the amount of 1 μM and 0.1 μM, respectively. ACK1 enzyme was cultured in 8 mM MOPS, 0.2 mM EDTA and 10 mM magnesium acetate buffer along with 400 μM EFPOYDFLPAKKK peptide. Here, ATP solution (5 μl) was added thereto and kinase reaction was performed at room temperature for 40 minutes. Then, 3% phosphoric acid was added to a reaction solution to stop the reaction. A droplet of 10 μl of the reaction solution was dropped to P30 filtermat, and washed 3 times with 75 mM phosphoric acid for 5 minutes. The washed reaction solution was dried, and counted via scintillation counting, and the result is shown in Table 2 below.

TABLE 2

| Ex. | Ack1 activation rate % (1 μM) | Ack1 activation rate % (0.1 μM) | Ex. | Ack1 activation rate % (1 μM) | Ack1 activation rate % (0.1 μM) |
|---|---|---|---|---|---|
| 1 | 1 | 4 | 44 | 1 | 2 |
| 2 | 2 | 9 | 45 | 0 | 1 |
| 3 | 2 | 2 | 56 | 0 | 1 |
| 4 | 1 | 12 | 57 | 0 | 1 |
| 5 | 0 | 2 | 58 | 1 | 5 |
| 7 | 1 | 2 | 59 | 0 | 2 |
| 8 | 1 | 7 | 60 | 0 | 1 |
| 9 | 1 | 8 | 61 | 0 | 2 |
| 10 | 0 | 2 | 62 | 1 | 19 |
| 11 | 0 | 2 | 63 | 0 | 2 |
| 12 | 0 | 3 | 64 | 2 | 1 |
| 13 | 0 | 0 | 65 | 1 | 2 |
| 14 | 0 | 1 | 66 | 3 | 0 |
| 19 | 0 | 6 | 67 | 0 | 2 |
| 21 | 0 | 0 | 68 | 0 | 1 |
| 22 | 0 | 1 | 69 | 0 | 1 |
| 23 | 0 | 1 | 70 | 0 | 3 |
| 24 | 0 | 2 | 71 | 0 | 3 |
| 25 | 0 | 4 | 72 | 0 | 1 |
| 26 | 1 | 0 | 73 | 0 | 1 |
| 27 | 0 | 1 | 74 | 0 | 0 |
| 28 | 2 | 1 | 75 | 0 | 2 |

TABLE 2-continued

| Ex. | Ack1 activation rate % (1 µM) | Ack1 activation rate % (0.1 µM) | Ex. | Ack1 activation rate % (1 µM) | Ack1 activation rate % (0.1 µM) |
|---|---|---|---|---|---|
| 29 | 2 | 11 | 77 | 0 | 0 |
| 30 | 0 | 2 | 78 | 0 | 1 |
| 31 | 0 | 2 | 79 | 0 | 0 |
| 35 | 0 | 1 | 80 | 0 | 0 |
| 36 | 0 | 2 | 81 | 1 | 3 |
| 37 | 0 | 2 | 82 | 0 | 2 |
| 38 | 0 | 1 | 83 | 0 | 0 |
| 40 | 0 | 2 | 84 | 0 | 1 |
| 41 | 0 | 1 | 85 | 0 | 0 |
| 42 | 0 | 2 | 88 | 0 | 0 |
| 43 | 1 | 1 | | | |

As shown in Table 2 above, the compounds prepared in Example 29 and Example 62 of the present invention were shown to reduce the ACK1 activation rate to 10% or below at a concentration of 0.1 µM, and to 3% or below at a concentration of 1 µM. In particular, in the case of the compounds prepared in Examples 13, 21, 26, 66, 74, 77, 79 and 80, the ACK1 activation rate was significantly reduced to 0%. Accordingly, the N2,N4-bis(4-(piperazin-1-yl)phenyl)pyrimidin-2,4-diamine derivative of the present invention was shown to have an excellent inhibitory activity against ACK1 activity at enzyme level even at a low concentration.

Accordingly, the N2,N4-bis(4-(piperazin-1-yl)phenyl)pyrimidin-2,4-diamine derivative of the present invention has an excellent inhibitory activity against ACK1 activity, and thus can be used as an effective inhibitor of ALK activity as well as a pharmaceutical composition for preventing or treating cancer such as prostate cancer, uterine cancer, stomach cancer, etc.

Experimental Example 3

Evaluation of Inhibitory Activity Against Cancer Cell Proliferation

In order to measure the inhibitory activity of N2,N4-bis(4-(piperazin-1-yl)phenyl)pyrimidin-2,4-diamine derivatives represented by Chemical Formula 1 according to the present invention against the cancer cell proliferation, an experiment was performed as follows.

<3-1> Experimental Materials

Reagents

RPMI 1640 as a cell culture medium, fetal bovine serum (FBS) and trypsin were purchased from Gibco Inc. (Grand Island, N.Y., USA) and sodium bicarbonate, amphotericin B, and gentamicin were purchased from Sigma Chemical Co.

Additionally, the reagents used for cytotoxicity such as sulforhodamine (SRB) B, trisma base, trichloroacetic acid (TCA), etc., were purchased from Sigma Chemical Co. For MTS assay, CellTiter 96R AQueous Non-Radioactive Cell Proliferation Assay products were purchased from Promega Corporation.

Furthermore, T-25 culture container for cell culture, a 96-well plate, and other disposable glassware were purchased from Falcon Transfer (Lincoln Park, N.J.).

Experimental Device

The ELISA microplate reader for measurement of cytotoxicity was E-max or SpectraMax250 of Molecular Devices (Sunnyvale, Calif., USA).

<3-2> Experimental Method

Step 1: Cell Culture

Final concentration of dimethyl sulfoxide was set at 0.5% or below.

The cancer cell lines used in the experiment are all human-originated cancer cell lines, and H3122, H2228, Hs746T, and H1993 were used.

The culture was performed using RPMI 1640 medium containing 10% fetal bovine serum (FBS) in an incubator under the conditions of 37° C. and 5% $CO_2$, and subcultured once in 3 to 4 days.

Step 2: Evaluation of Inhibitory Activity Against Proliferation According to Treatment with Compounds $1\times10^4$ cells were aliquoted into each well of a 96-well flat-bottom microplate, cultured for 24 hours so that cells were attached to the bottom, and the culture medium was removed. The respectively diluted culture medium of the compounds of Examples 1 to 45, Examples 55 to 73, and Examples 77 to 83 was added thereto and cultured for 72 hours. Upon completion of the culture with the compounds, the measurement of cytotoxicity of the compounds was performed using SRB, a staining reagent, or via MTS assay. Upon completion of the culture with the compounds of Examples 1 to 45, Examples 55 to 73, and Examples 77 to 83, the culture medium was removed and each well was treated with a cold TCA solution, and placed it at 4° C. for 1 hour to immobilize the cells. After removing the TCA solution and drying at room temperature, the cells were added with a staining solution, in which 0.4% SRB was dissolved in 1% acetic acid solution, and placed at room temperature for 30 minutes to stain the cells. The extra SRB which were not bound to the cells were removed by washing with an acetic acid solution, and the stained cells were added with 10 mM Tris buffer (Trisma base; unbuffered) at PH 10.3 to 10.5 to elute the SRB. The absorbance in each well was measured at 520 nm by ELISA microplate reader.

From the OD values for the wells (C) not treated with a drug, the wells (T) treated with a drug, and the wells (Tz) at the time of treating with a drug, the cytotoxicity of the drug was calculated:

when $Tz=T$, by the equation of $[(T-Tz)/(C-Tz)]100$, and when $Tz>T$, by the equation of $[(T-Tz)/(Tz)]100$.

The measurement of the inhibition of cancer cell proliferation via MTS assay was performed as follows. Specifically, upon completion of the culture with the compounds of Examples 1 to 45, Examples 55 to 73, and Examples 77 to 83, PMS solution and MTS solution, which constitute the CellTiter 96R AQueous Non-Radioactive Cell Proliferation Assay product of Promega Corporation were mixed and added to each well in the amount of 20 L. After placing in a culture container for 4 hours, the resultant was taken out of the container and left at room temperature for 10 minutes. After measuring the absorbance at 490 nM by SpectraMax250 of Molecular Device Co., Growth Inhibition 50 ($GI_{50}$) was calculated and the results are shown in Table 3 below.

TABLE 3

| Ex. | Hs746TCP $GI_{50}$ (µM) | H1993CP $GI_{50}$ (µM) | H2228CP $GI_{50}$ (µM) | H3122CP $GI_{50}$ (µM) |
|---|---|---|---|---|
| 1 | 3.43 | 6.91 | 1.59 | 0.96 |
| 2 | 2.86 | 7.25 | 1.42 | 0.874 |
| 3 | 2.92 | 5.94 | 1.17 | 0.41 |
| 4 | 1.38 | 3.47 | 0.32 | 0.19 |

TABLE 3-continued

| Ex. | Hs746TCP GI$_{50}$ (μM) | H1993CP GI$_{50}$ (μM) | H2228CP GI$_{50}$ (μM) | H3122CP GI$_{50}$ (μM) |
|---|---|---|---|---|
| 5 | 9.43 | >10 | 4.61 | 0.16 |
| 6 | 0.90 | 0.93 | 0.36 | 0.22 |
| 7 | 3.04 | 3.62 | 1.41 | 0.10 |
| 8 | 2.88 | 9.14 | 2.06 | 0.81 |
| 9 | 1.46 | 2.14 | 1.39 | 0.91 |
| 10 | 1.047 | 0.977 | 0.281 | 0.096 |
| 11 | 1.304 | 1.442 | 0.162 | 0.007 |
| 12 | 2.304 | 1.328 | 0.093 | 0.009 |
| 13 | 3.621 | 2.482 | 0.126 | 0.218 |
| 14 | 3.419 | 7.436 | 0.093 | 0.012 |
| 15 | 3.739 | 8.861 | 0.692 | 0.918 |
| 16 | 3.686 | 6.732 | 0.488 | 0.051 |
| 17 | 3.413 | 9.726 | 2.766 | 1.382 |
| 18 | 3.54 | 1.63 | 0.133 | 0.020 |
| 19 | >10 | >10 | 0.961 | 1.104 |
| 20 | >10 | >10 | 0.93 | 1.261 |
| 21 | 3.37 | 3.44 | 0.098 | 0.012 |
| 22 | 3.42 | 9.91 | 0.174 | 0.126 |
| 23 | 3.92 | 1.87 | 0.446 | 0.237 |
| 24 | 1.86 | 13.07 | 0.932 | 0.734 |
| 25 | >10 | 1.08 | 0.148 | 0.022 |
| 26 | >10 | 3.38 | 0.406 | 0.029 |
| 27 | >10 | 7.93 | 0.364 | 0.185 |
| 28 | >10 | 4.28 | 0.112 | 0.011 |
| 29 | >10 | 9.85 | 0.411 | 0.347 |
| 30 | >10 | 7.81 | 0.224 | 0.017 |
| 31 | >10 | 3.68 | 0.492 | 0.196 |
| 32 | 7.92 | 3.51 | 0.714 | 0.196 |
| 33 | 2.63 | 1.26 | 0.094 | 0.002 |
| 34 | 3.86 | 3.24 | 0.285 | 1.023 |
| 35 | 3.40 | 2.12 | 0.095 | 0.024 |
| 36 | 6.49 | >10 | 1.143 | 0.014 |
| 37 | 9.24 | >10 | 0.331 | 0.009 |
| 38 | 7.84 | >10 | 1.285 | 0.0091 |
| 39 | 5.73 | >10 | 1.297 | 0.844 |
| 40 | 9.56 | >10 | 0.981 | 0.276 |
| 41 | 6.14 | 9.88 | 0.780 | 0.306 |
| 42 | 9.68 | >10 | 0.126 | 0.032 |
| 43 | 6.33 | >10 | 0.963 | 0.187 |
| 44 | 8.04 | >10 | 0.952 | 0.020 |
| 45 | 9.93 | >10 | 0.971 | 0.144 |
| 55 | 2.67 | 9.17 | 1.09 | 0.43 |
| 56 | 2.74 | 2.33 | 0.127 | 0.0010 |
| 57 | 0.33 | 0.98 | 0.037 | 0.0010 |
| 58 | 1.86 | 8.26 | 0.143 | 0.0014 |
| 59 | 2.27 | 9.34 | 0.351 | 0.0009 |
| 60 | 1.59 | 6.27 | 0.338 | 0.0124 |
| 61 | 2.51 | >10 | 0.116 | 0.0011 |
| 62 | 2.19 | 2.46 | 0.72 | 0.22 |
| 63 | 3.13 | 2.38 | 0.132 | 0.0009 |
| 64 | 2.14 | 5.47 | 0.38 | 0.018 |
| 65 | 2.93 | 7.27 | 0.883 | 0.0064 |
| 66 | 3.25 | 5.38 | 0.365 | 0.0007 |
| 67 | 1.73 | >10 | 0.281 | 0.0143 |
| 68 | 2.25 | 3.36 | 0.119 | 0.0003 |
| 69 | 2.44 | 2.96 | 0.47 | 0.82 |
| 70 | 4.08 | >10 | 0.98 | 0.47 |
| 71 | 2.06 | 5.70 | 1.41 | 0.115 |
| 72 | 3.16 | 8.85 | 1.14 | 0.0081 |
| 73 | 0.37 | 7.92 | 8.09 | 0.941 |
| 77 | 1.38 | 1.41 | 0.18 | 0.21 |
| 78 | 5.06 | >10 | 0.93 | 0.43 |
| 79 | 8.11 | >10 | 0.29 | 0.30 |
| 80 | 7.87 | >10 | 0.095 | 0.0011 |
| 81 | 0.96 | 4.02 | 0.37 | 0.17 |
| 82 | 6.92 | >10 | 1.19 | 1.86 |
| 83 | 0.67 | >10 | 0.064 | 0.0008 |
| 대조군 | 0.00012 | 0.083 | 0.851 | 0.277 |

As shown in Table 3, the compounds according to the present invention were shown to inhibit the activities of ALK and ACK1 of Hs746TCP (stomach cancer cells), and H1993CP, H2228CP and H3122CP (lung cancer cells) thereby reducing their proliferation activities. In particular, among the compounds of Examples of the present invention, about 88% of the compounds showed GI$_{50}$ values of from 0.093 to 0.78, and from 0.003 to 0.276 in H2228CP and H3122CP (lung cancer cells), thus confirming their excellent inhibitory activity against cancer cell proliferation compared to that of the control group. Additionally, 84% of the compounds showed significantly higher inhibitory activities in both H2228CP and H3122CP against cancer cell proliferation compared to that of the control group. From the above results, was confirmed that the compounds of the present invention has superior inhibitory activities against the control group, which is currently used as a therapeutic agent for treating non-small cell lung cancer. Conclusively, the N2,N4-bis(4-(piperazin-1-yl)phenyl)pyrimidin-2,4-diamine derivatives represented by Chemical Formula 1 according to the present invention were confirmed to have inhibitory activities against cancer cell proliferation by inhibiting the activities of ALK and ACK1, and in particular, confirmed to have a superior inhibitory activity to that of Crizotinib® (positive control) a conventional therapeutic agent for treating non-small cell lung cancer by inhibiting the activity of ALK.

Accordingly, the N2,N4-bis(4-(piperazin-1-yl)phenyl)pyrimidin-2,4-diamine derivatives according to the present invention have not only an excellent inhibitory activity against the activity of ALK but also an excellent inhibitory activity against the activity of ACK1, thus can be effectively used as a pharmaceutical composition for preventing or treating cancers such as non-small cell lung cancer, neuroblastoma, inflammatory myelofibroblast tumor, rhabdomyosarcoma, myofibroblastoma, breast cancer, stomach cancer, lung cancer, and melanoma, but also can be used as a useful inhibitor of ALK and ACK1.

Experimental Example 4

Evaluation of Inhibitory Activity Against ALK Via Phosphorylation

In order to measure the inhibitory activity of the N2,N4-bis(4-(piperazin-1-yl)phenyl)pyrimidin-2,4-diamine derivatives represented by Chemical Formula 1 according to the present invention against the cell proliferation activity of ALK at an enzyme level, an experiment was performed as follows.

In order to confirm the inhibitory activity of the N2,N4-bis (4-(piperazin-1-yl)phenyl)pyrimidin-2,4-diamine derivatives according to the present invention against ALK by the phosphorylation rate of ALK, the phosphorylation rate of H3122, a lung cancer cell line treated with ALK, was measured. In particular, the phosphorylation rate of ALK was confirmed by treating with the compounds prepared in Examples 7, 11, 12, 14, 16, 21, 33, 35, 57-61, 63-68, 72, 80 and 83 according to the present invention, and untreated group was treated with dimethyl sulfoxide (DMSO) was treated, and control group was treated with CH5424802 (Chugai), Crizotinib® (Pfizer) and NVP-TAE684 (Novartis), and analyzed by comparing with the N2,N4-bis(4-(piperazin-1-yl)phenyl)pyrimidin-2,4-diamine derivatives according to the present invention.

The lung cancer cell line used was H3122, and it was cultured using an RPMI-1640 medium containing 10% fetal bovine serum (FBS) in a culture device at 37° C. with 5% CO$_2$, treated with the compounds at a concentration of 50 nM, and the cells were cultured further in a cell culture device for 6 hours. Then, the cultured cells were collected to obtain cellular proteins, and only ALK protein was obtained therefrom via immunoprecipitation using ALK antibodies. For the proteins obtained above, the phosphorylation rate of ALK was measured via Western Blot, and the result is shown in FIG. 1.

As shown in FIG. 1, the N2,N4-bis(4-piperazin-1-yl)phenyl)pyrimidin-2,4-diamine derivatives according to the present invention were confirmed to have excellent inhibitory activities against ALK. More specifically, when treated with the compounds prepared in Examples 7, 11, 12, 14, 16, 21, 33, 35, 57-61, 63-68, 72, 80 and 83 according to the present invention, ALK was inhibited by the treated compounds thus significantly lowering the concentration of ALK. In contrast, when treated with Akt and Erk, which are related to the proliferation of cancer cells, the effect of inhibition was not significant, and when treated with Tubulin, the tubule-forming protein, there was observed no inhibitory activity against the Tubulin activity thus confirming that they have excellent safety regarding the human blood vessels. Additionally, in the case of Crizotinib®, the conventional known ALK inhibitor, its inhibition rate of ALK was shown to be significantly lower comparing to the N2,N4-bis(4-piperazin-1-yl)phenyl)pyrimidin-2,4-diamine derivatives according to the present invention, and in the case of CH5424802, the inhibition rate was shown to be significantly lower. From the above, the N2,N4-bis(4-piperazin-1-yl)phenyl)pyrimidin-2,4-diamine derivatives according to the present invention were shown to have significantly improved inhibitory activities against ALK compared to the conventional ALK inhibitors, and also due to the lack of inhibitory activity against microtubules, they were shown to be safe to the humans.

Accordingly, the N2,N4-bis(4-piperazin-1-yl)phenyl)pyrimidin-2,4-diamine derivatives according to the present invention were shown to have excellent inhibitory activity against ALK activity, and thus can be used as a pharmaceutical composition for preventing or treating cancers such as non-small cell lung cancer, neuroblastoma, inflammatory myelofibroblast tumor, rhabdomyosarcoma, myofibroblastoma, breast cancer, stomach cancer, lung cancer, and melanoma, but also can be used as a useful inhibitor of ALK activity.

Experimental Example 5

Evaluation of Inhibitory Activity Against ACK1 Via Phosphorylation

In order to measure the inhibitory activity of the N2,N4-bis(4-(piperazin-1-yl)phenyl)pyrimidin-2,4-diamine derivatives represented by Chemical Formula 1 according to the present invention against the cell proliferation activity of ACK1 at an enzyme level, an experiment was performed as follows.

In order to confirm the inhibitory activity of the N2,N4-bis (4-(piperazin-1-yl)phenyl)pyrimidin-2,4-diamine derivatives according to the present invention against ACK1 by the phosphorylation rate of ACK1, the phosphorylation rate of LNCaP, a prostate cancer cell line treated with ACK1, was measured. In particular, after treating with the compounds prepared in Examples 1, 5, 7 and 11 according to the present invention, the phosphorylation rate of ACK1 was confirmed, as an untreated group dimethyl sulfoxide (DMSO) was treated, and as a control group CH5424802 (Chugai), Dasatinib® (Bristol-Myers Squibb) and immunoglobulin G(Ig G) were treated, and analyzed by comparing with those of the N2,N4-bis(4-(piperazin-1-yl)phenyl)pyrimidin-2,4-diamine derivative according to the present invention.

The prostate cancer cell line used was LNCaP, and it was cultured using an RPMI-1640 medium containing 10% fetal bovine serum (FBS) in a culture device at 37° C. with 5% $CO_2$, treated with the compounds at a concentration of 500 nM, and the cells were cultured further in a cell culture device for 3 hours. Then, the cultured cells were collected to obtain cellular proteins, and only ACK1 protein was obtained therefrom via immunoprecipitation using ACK1 antibodies. For the proteins obtained above, the phosphorylation rate of ACK1 was measured via Western Blot, and the result is shown in FIG. 2.

Figure 2:
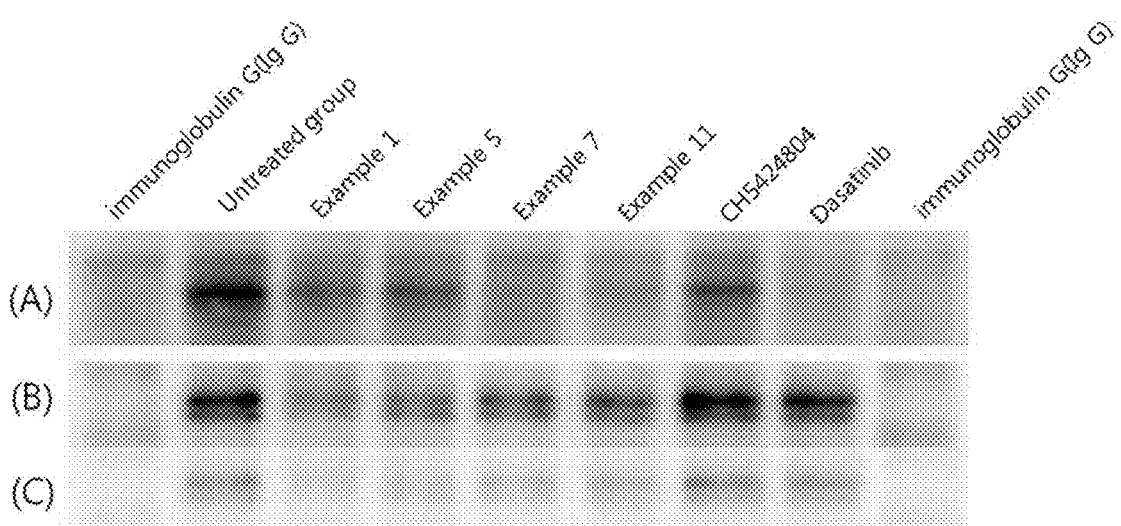
FIG. 2 is a picture showing the phosphorylation inhibitory effect by activated Cdc42-associated kinase (ACK1) (A: pY284 protein, B: Ack1 (long term exposure), C: Ack1 (short term exposure))

As shown in FIG. 2, the N2,N4-bis(4-piperazin-1-yl)phenyl)pyrimidin-2,4-diamine derivatives according to the present invention were confirmed to have excellent inhibitory activities against ACK1. More specifically, when treated with the compounds prepared in Examples 1, 5, 7 and 11 according to the present invention, ACK1 was inhibited by the treated compounds thus significantly lowering the concentration of ACK1. In contrast, in the case of Dasatinib®, which is known as a conventional tyrosine kinase inhibitor, the effect of inhibition was significantly lower than those of the N2,N4-bis(4-piperazin-1-yl)phenyl)pyrimidin-2,4-diamine derivatives according to the present invention, and in the case of CH5424802, the inhibition rate was significantly lower. From the above, the N2,N4-bis(4-piperazin-1-yl)phenyl)pyrimidin-2,4-diamine derivatives according to the present invention were shown to have significantly improved inhibitory activities against ACK1 compared to the conventional ACK1 inhibitors.

Accordingly, the N2,N4-bis(4-piperazin-1-yl)phenyl)pyrimidin-2,4-diamine derivatives according to the present invention were shown to have excellent inhibitory activity against ACK1 activity, and thus can be used as a pharmaceutical composition for preventing or treating cancers such as prostate cancer, uterine cancer, and stomach cancer, but also can be used as a useful inhibitor of ACK1 activity.

Experimental Example 6

Evaluation of Inhibitory Activity Against Tumor Cell Proliferation Via Animal Model In order to evaluate the inhibitory activity of the N2,N4-bis(4-(piperazin-1-yl)phenyl)pyrimidin-2,4-diamine derivatives represented by Chemical Formula 1 according to the present invention against the cancer cell proliferation, an experiment was performed as follows.

Figure 3:
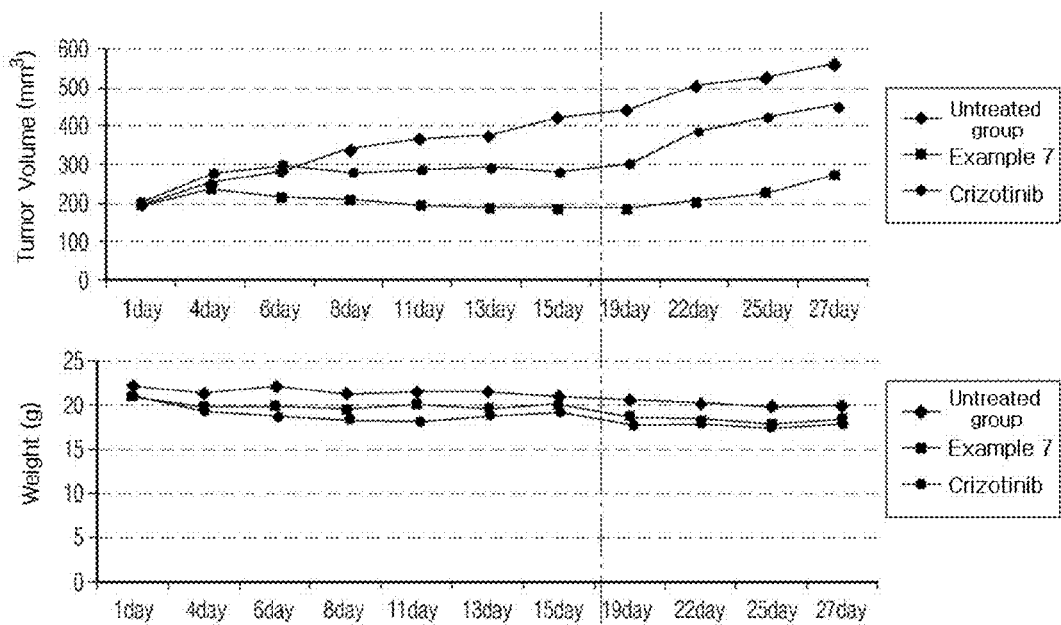
FIG. 3 is a graph showing changes in tumor volume and body weight of a xenografted mouse with a lung cancer cell line H3122 NSCLC administered with the compound of Example 7 and Crizotinib® over administration time.

An about 6 week old mouse was xenografted with H3122NSCLC, a lung cancer cell line, administered with the N2,N4-bis(4-(piperazin-1-yl)phenyl)pyrimidin-2,4-diamine derivatives according to the present invention, and the activation rate of inhibiting proliferation of lung cancer cells. First, the experimental animals were obtained according to the experimental animal guidelines, habituated, and progressed according to the approved animal experiment protocol. All experiments were progressed using mice xenografted with H3122NSCLC cell line. The experimental conditions were set at a temperature of 21±2° C., with a humidity of 50±5%, and the dark/light cycle was set at 12 hours (7 am-7 pm). During the experiment, the animals were given ad libitum access to food and water. The xenogratfted mouse was transplanted with the H3122 NSCLC cell line around 6 weeks of age, and administered with the compound of Example 7 according to the present invention, and was treated with Crizotinib® as a control group. In particular, the administration period was 14 days, and in the case of the compounds according to the present invention, the sample dissolved in a mixed solution of 20% polyethylene glycol 400 and 3% Tween 80 was administered once daily via intraperitoneal injection. In the case of Crizotinib®, it was administered orally once daily. Additionally, the number of the animals assigned per each group was eight, and as an untreated group, an excipient-treated group was used. For the mice treated with the samples, the volume of their tumors and their body weight were measured, and the results are shown in FIG. 3.

The N2,N4-bis(4-(piperazin-1-yl)phenyl)pyrimidin-2,4-diamine derivatives according to the present invention not only have excellent effect of inhibiting cancer cell proliferation but are also safe in the body. More specifically, when treated with the compound prepared in Example 7 according to the present invention, the volume of the xenografted tumor was 190 mm³-280 mm³ thus confirmed not showing a significant difference from the tumor volume in the first day of the experiment. In contrast, in the case of the untreated group, after 27 days of lapse, the volume of the tumor was about 560 mm³, about 2.8 fold increase compared to that of the first day. In the control group treated with Crizotinib®, after 27 days of lapse, the volume of the tumor was increased about 2.3 fold compared to that of the first day. Additionally, when treated with the compound prepared in Example 7 according to the present invention, the change in the body weight of the mice xenografted with a lung cancer cell line was negligible.

From the above, it was confirmed that the N2,N4-bis(4-(piperazin-1-yl)phenyl)pyrimidin-2,4-diamine derivatives according to the present invention have excellent inhibitory effect against cancer cell proliferation compared to those of the convential anticancer agents, and also that they lack of cytotoxicity and thus can be safely used in the body.

Accordingly, the N2,N4-bis(4-(piperazin-1-yl)phenyl)pyrimidin-2,4-diamine derivatives according to the present invention have excellent in vivo tumor inhibitory effect, and thus can be effectively used as a pharmaceutical composition for preventing or treating prostate cancer, uterine cancer, stomach cancer, etc.

Meanwhile, the N2,N4-bis(4-(piperazin-1-yl)phenyl)pyrimidin-2,4-diamine derivative of Chemical Formula 1 above according to the present invention may be formulated in various forms. Provide below are a few exemplary embodiments of formulation methods containing the N2,N4-bis(4-(piperazin-1-yl)phenyl)pyrimidin-2,4-diamine derivative represented by Chemical Formula 1 above, and the present invention is not limited thereto.

Formulation Example 1

Preparation of Pharmaceutical Formulation 1-1. Preparation of Powders

| | |
|---|---|
| compound of Chemical Formula 1 | 500 mg |
| lactose | 100 mg |
| talc | 10 mg |

The above components are mixed and filled into a sealed pouch to prepare powders.

1-2. Preparation of Tablets

| | |
|---|---|
| compound of Chemical Formula 1 | 500 mg |
| corn starch | 100 mg |
| lactose | 100 mg |
| magnesium stearate | 2 mg |

The above components are mixed and tableted to prepare tablets.

1-3. Preparation of Capsules

| | |
|---|---|
| compound of Chemical Formula 1 | 500 mg |
| corn starch | 100 mg |
| lactose | 100 mg |
| magnesium stearate | 2 mg |

According to a conventional method of preparing capsules, the above components are mixed and filled into capsules to prepare capsule formulations.

1-4. Preparation of Injections

| | |
|---|---|
| compound of Chemical Formula 1 | 500 mg |
| sterile distilled water for injection | adequate |
| pH adjuster | adequate |

According to a conventional method of preparing injections, the above components are contained per each ampoule (2 mL).

1-5. Preparation of Liquids

| | |
|---|---|
| compound of Chemical Formula 1 | 100 mg |
| isomerose | 10 g |
| mannitol | 5 g |
| distilled water | adequate |

According to the conventional method of preparing liquids, each component is respectively dissolved by adding with distilled water, added with an adequate amount of a lemon flavor. Then, the above components are mixed, added with distilled water to a final volume of 100 mL, filled into a brown bottle, and sterilized to prepare liquid formulations.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An N2,N4-bis(4-(piperazin-1-yl)phenyl)pyrimidin-2,4-diamine derivative represented by Chemical Formula 1 below or a pharmaceutically acceptable salt thereof:

[Chemical Formula 1]

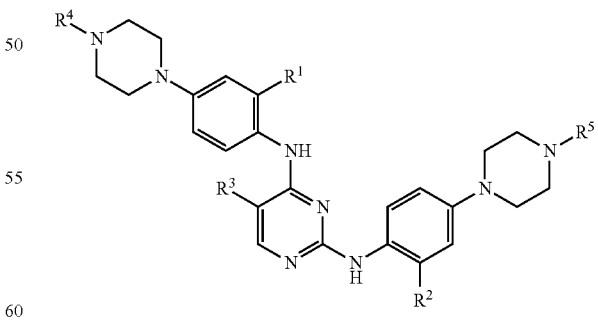

(in Chemical Formula 1,
$R^1$ and $R^2$ are independently H, halogen, —$OR^6$ or —$NR^7R^8$,
where $R^6$ is $C_1$-$C_4$ linear or branched alkyl unsubstituted, or substituted with at least one selected from the group consisting of halogen and $C_5$-$C_6$ aryl, $R^7$ and $R^8$ are independently H, $C_1$-$C_4$ linear or branched alkyl, $C_1$-$C_4$ linear or branched alkylcarbonyl or $C_5$-$C_6$ aryl;

$R^4$ and $R^5$ are independently H; $C_1$-$C_4$ linear or branched alkyl unsubstituted or substituted with hydroxy group; —C(=O)$R^9$ or —$SO_2$—$R^{10}$, where $R^9$ is $C_1$-$C_4$ linear or branched alkyl unsubstituted or substituted with hydroxy group; $C_1$-$C_4$ linear or branched alkyloxy; amino unsubstituted or substituted with $C_1$-$C_4$ linear or branched alkyl, and $R^{10}$ is $C_1$-$C_4$ linear or branched alkyl; amino unsubstituted or substituted with $C_1$-$C_4$ linear or branched alkyl, and $R^3$ is halogen; or $C_1$-$C_4$ linear or branched alkyl substituted with at least one halogen).

2. The N2,N4-bis(4-(piperazin-1-yl)phenyl)pyrimidin-2,4-diamine derivative or a pharmaceutically acceptable salt thereof of claim 1, wherein $R^1$ and $R^2$ are independently H, —$OR^6$ or —$NR^7R^8$, where $R^6$ is methyl, ethyl, propyl, isopropyl, butyl, isobutyl or t-butyl unsubstituted or substituted with at least one selected from the group consisting of chloro, bromo, fluoro, iodine, and phenyl, $R^7$ and $R^8$ are independently H; methyl; ethyl; propyl; isopropyl; butyl; isobutyl; t-butyl; methylcarbonyl; ethylcarbonyl; propylcarbonyl; isopropylcarbonyl; butylcarbonyl; isobutylcarbonyl or phenyl;

$R^4$ and $R^5$ are independently H; methyl, ethyl, propyl, isopropyl, butyl, isobutyl, t-butyl, —C(=O)$R^9$ or —$SO_2$—$R^{10}$ unsubstituted or substituted with hydroxyl, wherein $R^9$ is methyl, ethyl, propyl, isopropyl, butyl, isobutyl, t-butyl, methyloxy, ethyloxy, propyloxy, isopropyloxy, butyloxy, isobutyloxy, t-butyloxy, hydroxymethyl, hydroxyethyl, hydroxypropyl, hydroxyisopropyl, hydroxybutyl, hydroxyisobutyl, amino, methylamino, ethylamino, propylamino, isopropylamino, butylamino or isobutylamino, $R^{10}$ is methyl, ethyl, propyl, isopropyl, butyl, isobutyl, t-butyl, or amino; and $R^3$ is chloro; bromo; fluoro; iodine; or methyl, ethyl, propyl, isopropyl, butyl, isobutyl or t-butyl substituted from at least one selected from the group consisting of chloro, bromo, fluoro, and iodine.

3. The N2,N4-bis(4-(piperazin-1-yl)phenyl)pyrimidin-2,4-diamine derivative or a pharmaceutically acceptable salt thereof of claim 1, wherein $R^1$ is H, chloro, bromo, fluoro, methoxy, ethoxy, propoxy, isopropoxy, benzyloxy, difluoromethyloxy, dimethylamino, t-butylamino, phenylamino, ethylcarbonylmethylamino or propylcarbonylmethylamino;

$R^2$ is H or methoxy;

$R^3$ is chloro, fluoro, bromo or trifluoromethyl; and $R^4$ and $R^5$ are independently H, methyl, hydroxyethyl, methylcarbonyl, ethylcarbonyl, t-butylcarbonyl, hydroxymethylcarbonyl, ethylaminocarbonyl, methyloxycarbonyl, t-butyloxycarbonyl, methylsulfonyl or aminosulfonyl.

4. The N2,N4-bis(4-(piperazin-1-yl)phenyl)pyrimidin-2,4-diamine derivative or a pharmaceutically acceptable salt thereof of claim 1, wherein the derivative of Chemical Formula 1 is any one selected from the group consisting of:

(1) 1-(4-(4-(4-(4-(4-acetylpiperazin-1-yl)-2-ethoxyphenylamino)-5-chloropyrimidin-2-ylamino)-3-methoxyphenyl)piperazin-1-yl)ethanone;

(2) 1-(4-(4-(2-(4-(4-acetylpiperazin-1-yl)-2-methoxyphenylamino)-5-chloropyrimidin-4-ylamino)-3-propoxyphenyl)piperazin-1-yl)ethanone;

(3) 1-(4-(4-(4-(4-(4-acetylpiperazin-1-yl)-2-isopropoxyphenylamino)-5-chloropyrimidin-2-ylamino)-3-methoxyphenyl)piperazin-1-yl)ethanone;

(4) 1-(4-(4-(4-(4-(4-acetylpiperazin-1-yl)-2-propoxyphenylamino)-5-chloropyrimidin-2-ylamino)phenyl)piperazin-1-yl)ethanone;

(5) 1,1'-(4,4'-(4,4'-(5-fluoropyrimidin-2,4-diyl)bis(azanediyl)bis(3-methoxy-4,1-phenylene))bis(piperazin-4,1-diyl))diethanone;

(6) 1-(4-(4-(4-(4-(4-acetylpiperazin-1-yl)-2-ethoxyphenylamino)-5-chloropyrimidin-2-ylamino)phenyl)piperazin-1-yl)ethanone;

(7) 1,1'-(4,4'-(4,4'-(5-chloropyrimidin-2,4-diyl)bis(azanediyl)bis(3-methoxy-4,1-phenylene))bis(piperazin-4,1-diyl))diethanone;

(8) 1-(4-(4-(2-(4-(4-acetylpiperazin-1-yl)-2-methoxyphenylamino)-5-chloropyrimidin-4-ylamino)phenyl)piperazin-1-yl)ethanone;

(9) 1,1'-(4,4'-(4,4'-(5-chloropyrimidin-2,4-diyl)bis(azanediyl)bis(4,1-phenylene))bis(piperazin-4,1-diyl))diethanone;

(10) 1-(4-(4-(4-(4-(4-acetylpiperazin-1-yl)-2-methoxyphenylamino)-5-chloropyrimidin-2-ylamino)phenyl)piperazin-1-yl)ethanone;

(11) 1,1'-(4,4'-(4,4'-(5-(trifluoromethyl)pyrimidin-2,4-diyl)bis(azanediyl)bis(3-methoxy-4,1-phenylene))bis(piperazin-4,1-diyl))diethanone;

(12) 1-(4-(4-(5-chloro-4-(2-methoxy-4-(piperazin-1-yl)phenylamino)pyrimidin-2-ylamino)-3-methoxyphenyl)piperazin-1-yl)ethanone;

(13) 1-(4-(4-(5-chloro-4-(2-methoxy-4-(4-(methylsulfonyl)piperazin-1-yl)phenylamino)pyrimidin-2-ylamino)-3-methoxyphenyl)piperazin-1-yl)ethanone;

(14) 1-(4-(4-(2-(4-(4-acetylpiperazin-1-yl)-2-methoxyphenylamino)-5-chloropyrimidin-4-ylamino)-3-methoxyphenyl)piperazin-1-yl)-2-hydroxyethanone;

(15) tert-butyl 4-(4-(2-(4-(4-acetylpiperazin-1-yl)-2-methoxyphenylamino)-5-chloropyrimidin-4-ylamino)-3-methoxyphenyl)piperazin-1-carboxylate;

(16) 1-(4-(4-(5-chloro-4-(4-(4-(2-hydroxyethyl)piperazin-1-yl)-2-methoxyphenylamino)pyrimidin-2-ylamino)-3-methoxyphenyl)piperazin-1-yl)ethanone;

(17) 1-(4-(4-(4-(4-(4-acetylpiperazin-1-yl)-2-(benzyloxy)phenylamino)-5-chloropyrimidin-2-ylamino)-3-methoxyphenyl)piperazin-1-yl)ethanone;

(18) 1,1'-(4,4'-(4,4'-(5-bromopyrimidin-2,4-diyl)bis(azanediyl)bis(3-methoxy-4,1-phenylene))bis(piperazin-4,1-diyl))diethanone;

(19) 1,1'-(4,4'-(4,4'-(pyrimidin-2,4-diylbis(azanediyl))bis(3-methoxy-4,1-phenylene))bis(piperazin-4,1-diyl))diethanone;

(20) methyl 4-(4-(2-(4-(4-acetylpiperazin-1-yl)-2-methoxyphenylamino)-5-chloropyrimidin-4-ylamino)-3-methoxyphenyl)piperazin-1-carboxylate;

(21) 4-(4-(2-(4-(4-acetylpiperazin-1-yl)-2-methoxyphenylamino)-5-chloropyrimidin-4-ylamino)-3-methoxyphenyl)piperazin-1-sulfonamide;

(22) 1-(4-(4-(2-(4-(4-acetylpiperazin-1-yl)-2-methoxyphenylamino)-5-chloropyrimidin-4-ylamino)-3-methoxyphenyl)piperazin-1-yl)propan-1-one;

(23) 1-(4-(4-(2-(4-(4-acetylpiperazin-1-yl)-2-methoxyphenylamino)-5-chloropyrimidin-4-ylamino)-3-methoxyphenyl)piperazin-1-yl)-2,2-dimethylpropan-1-one;

(24) 1-(4-(4-(4-(4-(4-acetylpiperazin-1-yl)-2-methoxyphenylamino)-5-fluoropyrimidin-2-ylamino)phenyl)piperazin-1-yl)ethanone;

(25) tert-butyl 4-(4-(2-(4-(4-acetylpiperazin-1-yl)-2-methoxyphenylamino)-5-fluoropyrimidin-4-ylamino)-3-methoxyphenyl)piperazin-1-carboxylate;

(26) 1-(4-(4-(5-fluoro-4-(2-methoxy-4-(4-(methylsulfonyl)piperazin-1-yl)phenylamino)pyrimidin-2-ylamino)-3-methoxyphenyl)piperazin-1-yl)ethanone;

(27) methyl 4-(4-(2-(4-(4-acetylpiperazin-1-yl)-2-methoxyphenylamino)-5-fluoropyrimidin-4-ylamino)-3-methoxyphenyl)piperazin-1-carboxylate;

(28) 1-(4-(4-(5-fluoro-4-(4-(4-(2-hydroxyethyl)piperazin-1-yl)-2-methoxyphenylamino)pyrimidin-2-ylamino)-3-methoxyphenyl)piperazin-1-yl)ethanone;

(29) 1-(4-(4-(4-(4-acetylpiperazin-1-yl)-2-ethoxyphenylamino)-5-fluoropyrimidin-2-ylamino)-3-methoxyphenyl)piperazin-1-yl)ethanone;

(30) 1-(4-(4-(5-fluoro-4-(2-methoxy-4-(4-methylpiperazin-1-yl)phenylamino)pyrimidin-2-ylamino)-3-methoxyphenyl)piperazin-1-yl)ethanone;

(31) 4-(4-(2-(4-(4-acetylpiperazin-1-yl)-2-methoxyphenylamino)-5-fluoropyrimidin-4-ylamino)-3-methoxyphenyl)-N-ethylpiperazin-1-carboxyamide;

(32) 1-(4-(4-(5-fluoro-4-(2-methoxy-4-(piperazin-1-yl)phenylamino)pyrimidin-2-ylamino)-3-methoxyphenyl)piperazin-1-yl)ethanone;

(33) tert-butyl 4-(4-(2-(4-(4-acetylpiperazin-1-yl)-2-methoxyphenylamino)-5-chloropyrimidin-4-ylamino)-3-(difluoromethoxy)phenyl)piperazin-1-carboxylate;

(34) 1-(4-(4-(5-chloro-4-(2-(difluoromethoxy)-4-(piperazin-1-yl)phenylamino)pyrimidin-2-ylamino)-3-methoxyphenyl)piperazin-1-yl)ethanone;

(35) 1-(4-(4-(4-(4-(4-acetylpiperazin-1-yl)-2-(difluoromethoxy)phenylamino)-5-chloropyrimidin-2-ylamino)-3-methoxyphenyl)piperazin-1-yl)ethanone;

(36) 1-(4-(4-(2-(4-(4-acetylpiperazin-1-yl)-2-methoxyphenylamino)-5-fluoropyrimidin-4-ylamino)-3-methoxyphenyl)piperazin-1-yl)-2-hydroxyethanone;

(37) 1-(4-(4-(4-(2-(difluoromethoxy)-4-(piperazin-1-yl)phenylamino)-5-fluoropyrimidin-2-ylamino)-3-methoxyphenyl)piperazin-1-yl)ethanone;

(38) 1-(4-(4-(4-(2-(difluoromethoxy)-4-(4-methylpiperazin-1-yl)phenylamino)-5-fluoropyrimidin-2-ylamino)-3-methoxyphenyl)piperazin-1-yl)ethanone;

(39) tert-butyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate;

(40) 1-(4-(4-(4-(2-(difluoromethoxy)-4-(4-(methylsulfonyl)piperazin-1-yl)phenylamino)-5-fluoropyrimidin-2-ylamino)-3-methoxyphenyl)piperazin-1-yl)ethanone;

(41) methyl 4-(4-(2-(4-(4-acetylpiperazin-1-yl)-2-methoxyphenylamino)-5-fluoropyrimidin-4-ylamino)-3-(difluoromethoxy)phenyl)piperazin-1-carboxylate;

(42) 1-(4-(4-(4-(2-(difluoromethoxy)-4-(4-(2-hydroxyethyl)piperazin-1-yl)phenylamino)-5-fluoropyrimidin-2-ylamino)-3-methoxyphenyl)piperazin-1-yl)ethanone;

(43) 4-(4-(2-(4-(4-acetylpiperazin-1-yl)-2-methoxyphenylamino)-5-fluoropyrimidin-4-ylamino)-3-(difluoromethoxy)phenyl)-N-ethylpiperazin-1-carboxyamide;

(44) 1-(4-(4-(2-(4-(4-acetylpiperazin-1-yl)-2-methoxyphenylamino)-5-fluoropyrimidin-4-ylamino)-3-(difluoromethoxy)phenyl)piperazin-1-yl)-2-hydroxyethanone;

(45) 1-(4-(4-(2-(4-(4-acetylpiperazin-1-yl)-2-methoxyphenylamino)-5-fluoropyrimidin-4-ylamino)-3-(difluoromethoxy)phenyl)piperazin-1-yl)ethanone;

(46) 1-(4-(4-(4-(4-(4-acetylpiperazin-1-yl)-2-(tert-butylamino)phenylamino)-5chloropyrimidin-2-ylamino)-3-methoxyphenyl)piperazin-1-yl)ethanone;

(47) 1-(4-(4-(4-(4-(4-acetylpiperazin-1-yl)-2-(phenylamino)phenylamino)-5-chloropyrimidin-2-ylamino)-3-methoxyphenyl)piperazin-1-yl)ethanone;

(48) tert-butyl 4-(4-(2-(4-(4-acetylpiperazin-1-yl)-2-methoxyphenylamino)-5-chloropyrimidin-4-ylamino)-3-(N-methylpropionamido)phenyl)piperazin-1-carboxylate;

(49) tert-butyl 4-(4-(2-(4-(4-acetylpiperazin-1-yl)-2-methoxyphenylamino)-5-chloropyrimidin-4-ylamino)-3-(N-methylbutylamido)phenyl)piperazin-1-carboxylate;

(50) N-(2-(2-(4-(4-acetylpiperazin-1-yl)-2-methoxyphenylamino)-5-chloropyrimidin-4-ylamino)-5-(piperazin-1-yl)phenyl)-N-methylpropionamide;

(51) N-(2-(2-(4-(4-acetylpiperazin-1-yl)-2-methoxyphenylamino)-5-chloropyrimidin-4-ylamino)-5-(piperazin-1-yl)phenyl)-N-methylbutylamide;

(52) tert-butyl 4-(4-(4-(4-(4-acetylpiperazin-1-yl)-2-methoxyphenylamino)-5-chloropyrimidin-2-ylamino)-3-methoxyphenyl)piperazin-1-carboxylate;

(53) N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylpropionamide;

(54) N-(5-(4-acetylpiperazin-1-yl)-2-(2-(4-(4-acetylpiperazin-1-yl)-2-methoxyphenylamino)-5-chloropyrimidin-4-ylamino)phenyl)-N-methylbutylamide;

(55) tert-butyl4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-carboxylate;

(56) 1-(4-(3-methoxy-4-((4-((2-methoxy-4-(piperazin-1-yl)phenyl)amino)-5-(trifluoromethyl)pyrimidin-2-yl)amino)phenyl)piperazin-1-yl)ethanone;

(57) 4-(4-((2-((4-(4-acetylpiperazin-1-yl)-2-methoxyphenyl)amino)-5-(trifluoromethyl)pyrimidin-4-yl)amino)-3-methoxyphenyl)-N-ethylpiperazin-1-carboxyamide;

(58) 1-(4-(4-((2-((4-(4-acetylpiperazin-1-yl)-2-methoxyphenyl)amino)-5-(trifluoromethyl)pyrimidin-4-yl)amino)-3-methoxyphenyl)piperazin-1-yl)-2-hydroxyethanone;

(59) 1-(4-(3-methoxy-4-((4-((2-methoxy-4-(4-methoxypiperazin-1-yl)phenyl)amino)-5-(trifluoromethyl)pyrimidin-2-yl)amino)phenyl)piperazin-1-yl)ethanone;

(60) N-(4-(3-methoxy-4-((4-((2-methoxy-4-(4-(methylsulfonyl)piperazin-1-yl)phenyl)amino)-5-(trifluoromethyl)pyrimidin-2-yl)amino)phenyl)piperazin-1-yl)ethanone;

(61) 1-(4-(4-((4-((4-(4-(2-hydroxyethyl)piperazin-1-yl)-2-methoxyphenyl)amino)-5-(trifluoromethyl)pyrimidin-2-yl)amino)-3-methoxyphenyl)piperazin-1-yl)ethanone;

(62) tert-butyl4-(4-((4-((4-(4-acetylpiperazin-1-yl)-2-methoxyphenyl)amino)-5-(trifluoromethyl)pyrimidin-2-yl)amino)-3-methoxyphenyl)piperazin-1-carboxylate;

(63) 1-(4-(3-methoxy-4-((2-((2-methoxy-4-(piperazin-1-yl)phenyl)amino)-5-(trifluoromethyl)pyrimidin-4-yl)amino)phenyl)piperazin-1-yl)ethanone;

(64) 4-(4-((4-((4-(4-acetylpiperazin-1-yl)-2-methoxyphenyl)amino)-5-(trifluoromethyl)pyrimidin-2-yl)amino)-3-methoxyphenyl)-N-ethylpiperazin-1-carboxylate;

(65) 1-(4-(4-((4-((4-(4-acetylpiperazin-1-yl)-2-methoxyphenyl)amino)-5-(trifluoromethyl)pyrimidin-2-yl)amino)-3-methoxyphenyl)piperazin-1-yl)-2-hydroxyethanone;

(66) 1-(4-(3-methyl-4-((2-((-methoxy-4-(4-methylpiperazin-1-yl)phenyl)amino)-5-(trifluoromethyl)pyrimidin-4-yl)amino)phenyl)piperazin-1-yl)ethanone;

(67) 1-(4-(3-methoxy-4-((2-((2-methoxy-4(4-(methylsulfonyl)piperazin-1-yl-phenyl)amino)-5-(trifluoromethyl)pyrimidin-4-yl)amino)phenyl)piperazin-1-yl)ethanone;

(68) 1-(4-(4-((2-((4-(4-(2-hydroxyethyl)piperazin-1-yl)-2-methoxyphenyl)amino)-5-(trifluoromethyl)pyrimidin-4-yl)amino)-3-methoxyphenyl)piperazin-1-yl)ethanone;

(69) N2,N4-bis(2-methoxy-4-(piperazin-1-yl)phenyl)-5-(trifluoromethyl)pyrimidin-2,4-diamine;

(70) 4,4'-(((5-trifluoromethyl)pyrimidin-2,4-diyl)bis(azanediyl))bis(3-methoxy-4,1-phenylene))bis(piperazin-1-carboxylate);

(71) 4,4'-(((5-trifluoromethyl)pyrimidin-2,4-diyl)bis(azanediyl))bis(3-methoxy-4,1-phenylene))bis(N-ethylpiperazin-1-carboxyamide);

(72) 4,4'-(((5-(trifluoromethyl)pyrimidin-2,4-diyl)bis(azanediyl))bis(3-methoxy-4,1-phenylene))bis(N-ethylpiperazin-1-carboxyamide);

(73) 1,1'-(4,4'-(((5-(trifluoromethyl)pyrimidin-2,4-diyl)bis(azanediyl))bis(3-difluoromethoxy)-4,1-phenylene))bis(piperazin-4,1-diyl))diethanone;

(74) 1-(4-(4-((4-(4-acetylpiperazin-1-yl)-2-chlorophenyl)amino)-5-chloropyrimidin-2-yl)amino)-3-methoxyphenyl)piperazin-1-yl)ethanone;

(75) 1,1'-(4,4'-(((5-chloropyrimidin-2,4-diyl)bis(azanediyl))bis(3-chloro-4,1-phenylene))bis(piperazin-4,1-diyl)diethanone;

(76) 1-(4-(4-((2-((4-(4-acetylpiperazin-1-yl)-2-methoxyphenyl)amino)-5-chloropyrimidin-4-yl)amino)-3-phenoxyphenyl)piperazin-1-yl)ethanone;

(77) 5-chloro-N2-N4-bis(2-methoxy-4-(piperazin-1-yl)phenyl)pyrimidine-2,4-diamine;

(78) 4,4'-(((5-chloropyrimidin-2,4-diyl)bis(azanediyl))bis(3-methoxy-4,1-phenylene))bis(N-ethylpiperazin-1-carboxyamide);

(79) 5-chloro-N2,N4-bis(2-methoxy-4-(4-(methylsulfonyl)piperazin-1-yl)phenyl)pyrimidin-2,4-diamine;

(80) 1,1'-(4,4'-(((5-chloropyrimidin-2,4-diyl)bis(azanediyl))bis(3-methoxy-4,1-phenylene)bis(piperazin-4,1-diyl))bis(2-hydroxyethanone);

(81) 1-(4-(4-((5-chloro-4-((2-fluoro-4-(piperazin-1-yl)phenyl)amino)pyrimidin-2-yl)amino)-3-methoxyphenyl)piperazin-1-yl)ethanone;

(82) 1-(4-(4-((4-((4-acetylpiperazin-1-yl)-2-fluorophenyl)amino)-5-chloropyrimidin-2-yl)amino)-3-methoxyphenyl)piperazin-1-yl)ethanone;

(83) 1-(4-(4-((4-((4-(4-acetylpiperazin-1-yl)-2-methoxyphenyl)amino)-5-chloropyrimidin-2-yl)amino)-3-methoxyphenyl)piperazin-1-yl)-2-hydroxyethanone;

(84) methyl4-(4-((4-((4-(4-acetylpiperazin-1-yl)-2-methoxyphenyl)amino)-5-chloropyrimidin-2-yl)amino)-3-methoxyphenyl)piperazin-1-carboxylate;

(85) 1-(4-(4-((5-chloro-2-((4-(4-(2-hydroxyethyl)piperazin-1-yl)-2-methoxyphenyl)amino)pyrimidin-4-yl)amino)-3-methoxyphenyl)piperazin-1-yl)ethanone;

(86) 4-(4-((4-((4-(4-acetylpiperazin-1-yl)-2-methoxyphenyl)amino)-5-chloropyrimidin-2-yl)amino)-3-methoxyphenyl)piperazin-1-sulfonamide;

(87) 1-(4-(4-((5-chloro-2-((2-methoxy-4-(4-(methylsulfonyl)piperazin-1-yl)phenyl)amino)pyrimidin-4-yl)amino)-3-methoxyphenyl)piperazin-1-yl)ethanone;

(88) 1-(4-(4-((2-((4-(4-acetylpiperazin-1-yl)-2-methoxyphenyl)amino)-5-chloropyrimidin-4-yl)amino)-3-(difluoromethoxy)phenyl)piperazin-1-yl)-2-hydroxyethanone; and

(89) 1-(4-(3-(difluoromethoxy)-4-(5-fluoro-2-(2-methoxy-4-(piperazin-1-yl)phenylamino)pyrimidin-4-ylamino)phenyl)piperazin-1-yl)ethanone.

5. A method of manufacturing the N2,N4-bis(4-(piperazin-1-yl)phenyl)pyrimidin-2,4-diamine derivative or a pharmaceutically acceptable salt thereof of claim 1, comprising, as shown in Reaction Scheme 1 below:

preparing a compound of Chemical Formula 4 by reacting the chloro group at position 4 of the compound represented by Chemical Formula 2 with the amino group of the compound represented by Chemical Formula 3 (Step 1); and preparing a compound of Chemical Formula 1 by reacting the chloro group at position 2 of pyrimidine of the compound represented by Chemical Formula 4 obtained in Step 1 with the compound represented by Chemical Formula 5 (Step 2),

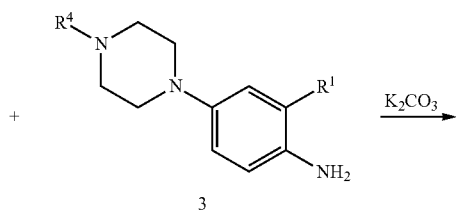

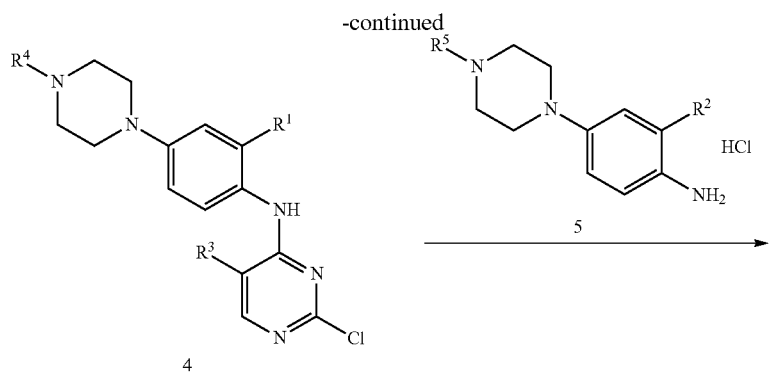

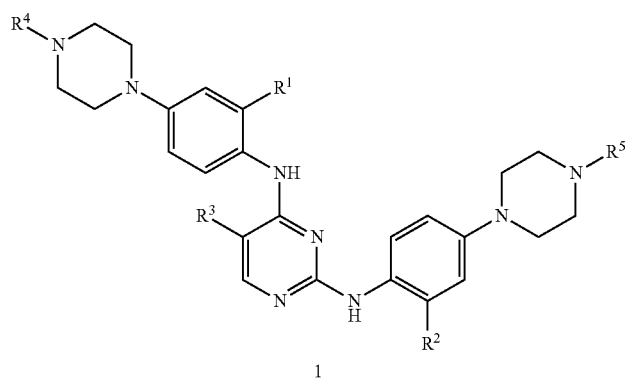

(in Reaction Scheme 1, $R^1$ to $R^5$ are the same as defined in Chemical Formula 1 in claim 1).

6. A method of manufacturing the N2,N4-bis(4-(piperazin-1-yl)phenyl)pyrimidin-2,4-diamine derivative or the pharmaceutically acceptable salt thereof of claim 1, as shown in Reaction Scheme 2, for manufacturing a compound represented by Chemical Formula 1a by reacting the chloro group of the compound represented by Chemical Formula 2 with at least 2 equivalents of the amino group of the compound represented by Chemical Formula 3:

[Reaction Scheme 2]

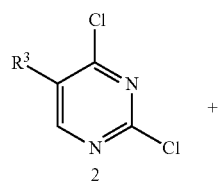

+

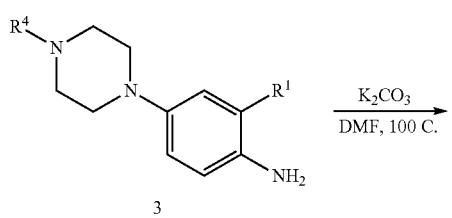

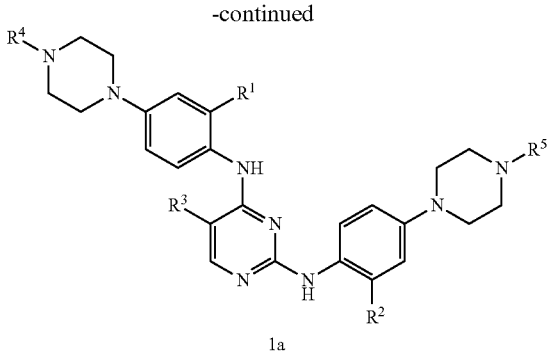

(in Reaction Scheme 2, $R^1$, $R^3$ and $R^4$ are the same as defined in Chemical Formula 1 of claim 1; and
the compound of Chemical Formula 1a is the compound of Chemical Formula 1).

7. A pharmaceutical composition for the treatment of cancers, wherein the cancers are non-small cell lung cancer, neuroblastoma, inflammatory myelofibroblast tumor, rhabdomyosarcoma, myofibroblastoma, breast cancer, stomach cancer, lung cancer, melanoma, large B-cell lymphoma, systemic histiocytosis, inflammatory myofibroblastic tumor or esophageal squamous cell carcinoma comprising the N2,N4-bis(4-(piperazin-1-yl)phenyl)pyrimidin-2,4-diamine derivative represented by Chemical Formula 1 or a pharmaceutically acceptable salt thereof of claim 1 as an active ingredient.

8. The pharmaceutical composition for the treatment of cancers of claim 7, wherein the activity of anaplastic lymphoma kinase (ALK) is inhibited to thereby inhibit the expression and growth of cancer cells.

9. The pharmaceutical composition for the treatment of cancers of claim 7, wherein the activity of activated Cdc42- associated kinase (ACK1) is inhibited to thereby inhibit the expression and growth of cancer cells.

10. An inhibitor of anaplastic lymphoma kinase (ALK) comprising the N2,N4-bis(4-(piperazin-1-yl)phenyl)pyrimidin-2,4-diamine derivative or the pharmaceutically acceptable salt thereof of claim 1 as an active ingredient.

11. An inhibitor of activated cdc42-associated kinase (ACK1) comprising the N2,N4-bis(4-(piperazin-1-yl)phenyl)pyrimidin-2,4-diamine derivative or the pharmaceutically acceptable salt thereof of claim 1 as an active ingredient.

* * * * *